(12) United States Patent
Allen et al.

(10) Patent No.: US 11,090,057 B2
(45) Date of Patent: Aug. 17, 2021

(54) EMBOLISATION SYSTEMS

(71) Applicant: Embo Medical Limited, Enniscorthy (IE)

(72) Inventors: Wayne Allen, County Galway (IE); Colin Forde, County Galway (IE); Paul Gilson, County Galway (IE); Liam Mullins, County Westmeath (IE); William Sheridan, County Cavan (IE)

(73) Assignee: EMBO MEDICAL LIMITED, Enniscorthy (IE)

( * ) Notice: Subject to any disclaimer, the term of this patent is extended or adjusted under 35 U.S.C. 154(b) by 255 days.

(21) Appl. No.: 14/777,226

(22) PCT Filed: Mar. 14, 2014

(86) PCT No.: PCT/EP2014/055186
§ 371 (c)(1),
(2) Date: Feb. 23, 2016

(87) PCT Pub. No.: WO2014/140325
PCT Pub. Date: Sep. 18, 2014

(65) Prior Publication Data
US 2016/0030047 A1    Feb. 4, 2016

Related U.S. Application Data

(60) Provisional application No. 61/885,868, filed on Oct. 2, 2013, provisional application No. 61/787,223, filed on Mar. 15, 2013.

(51) Int. Cl.
*A61B 17/12* (2006.01)
*A61B 17/00* (2006.01)
(Continued)

(52) U.S. Cl.
CPC ...... *A61B 17/1214* (2013.01); *A61B 17/0057* (2013.01); *A61B 17/1215* (2013.01);
(Continued)

(58) Field of Classification Search
CPC .......... A61B 17/0057; A61B 17/12022; A61B 17/12113; A61B 17/1214;
(Continued)

(56) References Cited

U.S. PATENT DOCUMENTS

| 5,256,146 A | 10/1993 | Ensminger et al. |
| 5,573,547 A | 11/1996 | LeVeen et al. |

(Continued)

FOREIGN PATENT DOCUMENTS

| CA | 2842238 A1 | 2/2013 |
| DE | 19607451 A1 | 9/1997 |

(Continued)

OTHER PUBLICATIONS

International Search Report and Written Opinion for PCT/EP2015/071097 dated Apr. 15, 2016.
(Continued)

*Primary Examiner* — Katrina M Stransky
*Assistant Examiner* — Mikail A Mannan
(74) *Attorney, Agent, or Firm* — Dinsmore & Shohl LLP

(57) ABSTRACT

A bristle device (8) for delivery into a body lumen comprises a longitudinally extending stem and a plurality of bristles extending generally outwardly from the stem for anchoring the device in a body lumen. There may beat least two bristle segments (96) and there are flexible sections (95) between the segments (96). The flexible sections (95) articulate to enable the device to pass through a catheter placed in a tortuous anatomy or to be deployed in a curved vessel, or
(Continued)

across a bifurcation. In some cases at least some of the bristle segments (96) are spaced-apart to accommodate bending of the bristles.

23 Claims, 97 Drawing Sheets

(51) Int. Cl.
 *A61F 2/01* (2006.01)
 *A61F 2/82* (2013.01)
(52) U.S. Cl.
 CPC .... *A61B 17/1219* (2013.01); *A61B 17/12031* (2013.01); *A61B 17/12109* (2013.01); *A61B 17/12113* (2013.01); *A61B 17/12163* (2013.01); *A61B 2017/00575* (2013.01); *A61B 2017/00623* (2013.01); *A61B 2017/1205* (2013.01); *A61B 2017/12054* (2013.01); *A61B 2017/12095* (2013.01); *A61F 2/01* (2013.01); *A61F 2/013* (2013.01); *A61F 2002/016* (2013.01); *A61F 2002/823* (2013.01); *A61F 2230/0069* (2013.01)
(58) Field of Classification Search
 CPC .......... A61B 17/12145; A61B 17/1215; A61B 17/12163; A61B 17/12109; A61F 2/01; A61F 2/013
 See application file for complete search history.

(56) References Cited

U.S. PATENT DOCUMENTS

| | | | |
|---|---|---|---|
| 5,630,844 | A | 5/1997 | Aydin et al. |
| 5,683,411 | A * | 11/1997 | Kavteladze ........ A61B 17/0057 606/200 |
| 5,693,067 | A | 12/1997 | Purdy |
| 5,702,421 | A | 12/1997 | Schneidt |
| 5,855,578 | A | 1/1999 | Guglielmi |
| 5,911,717 | A | 6/1999 | Jacobsen et al. |
| 6,159,206 | A | 12/2000 | Ogawa |
| 6,511,468 | B1 * | 1/2003 | Cragg ............... A61B 17/12022 128/898 |
| 7,901,704 | B2 | 3/2011 | Richard |
| 8,545,532 | B2 * | 10/2013 | Brandeis .......... A61B 17/12022 606/127 |
| 8,876,852 | B2 | 11/2014 | Shirley et al. |
| 2002/0161390 | A1 | 10/2002 | Mouw |
| 2003/0015203 | A1 | 1/2003 | Makower et al. |
| 2004/0034366 | A1 | 2/2004 | Van Der Burg |
| 2005/0004598 | A1 | 1/2005 | White et al. |
| 2005/0043755 | A1 | 2/2005 | Wilson et al. |
| 2005/0085847 | A1 | 4/2005 | Galdonik et al. |
| 2005/0209679 | A1 | 9/2005 | Melsheimer |
| 2006/0116713 | A1 | 6/2006 | Sepetka et al. |
| 2006/0167489 | A1 | 7/2006 | Satake et al. |
| 2006/0184194 | A1 | 8/2006 | Pal et al. |
| 2006/0229668 | A1 | 10/2006 | Prestezog et al. |
| 2006/0287667 | A1 | 12/2006 | Abela |
| 2007/0135826 | A1 | 6/2007 | Zaver et al. |
| 2007/0142859 | A1 | 6/2007 | Buiser et al. |
| 2007/0142893 | A1 | 6/2007 | Buiser et al. |
| 2007/0227544 | A1 * | 10/2007 | Swann ............... A61B 17/12022 128/831 |
| 2007/0270905 | A1 | 11/2007 | Osborne |
| 2007/0293928 | A1 | 12/2007 | Tomlin |
| 2008/0097374 | A1 | 4/2008 | Korleski et al. |
| 2009/0062838 | A1 | 3/2009 | Brumleve |
| 2010/0094335 | A1 | 4/2010 | Gerberding et al. |
| 2010/0179583 | A1 | 7/2010 | Carpenter et al. |
| 2010/0211087 | A1 | 8/2010 | Osborne |
| 2010/0312321 | A1 | 12/2010 | Kiyosue et al. |
| 2011/0008529 | A1 | 1/2011 | Hossainy et al. |
| 2011/0230810 | A1 | 9/2011 | Raman et al. |
| 2013/0204234 | A1 * | 8/2013 | Cully ............... A61B 17/12109 606/1 |
| 2014/0058498 | A1 | 2/2014 | Hannes et al. |
| 2014/0277346 | A1 | 9/2014 | Kanjickal et al. |
| 2015/0005807 | A1 | 1/2015 | Lagodzki et al. |
| 2016/0166257 | A1 | 6/2016 | Allen et al. |

FOREIGN PATENT DOCUMENTS

| | | |
|---|---|---|
| EP | 743047 A2 | 11/1996 |
| EP | 0778006 A1 | 6/1997 |
| EP | 882428 A2 | 12/1998 |
| EP | 0948935 A1 | 10/1999 |
| EP | 1035808 B1 | 9/2000 |
| EP | 1051116 B1 | 11/2000 |
| EP | 1584298 A1 | 10/2005 |
| EP | 1761178 B1 | 3/2007 |
| EP | 2316355 A1 | 5/2011 |
| EP | 2340785 A1 | 7/2011 |
| EP | 2987464 A1 | 2/2016 |
| EP | 3085310 A1 | 10/2016 |
| JP | 2001079011 A | 3/2001 |
| JP | 2007000572 A | 1/2007 |
| WO | 9306884 A1 | 4/1993 |
| WO | 9409706 A1 | 5/1994 |
| WO | 2001015608 | 3/2001 |
| WO | 0166167 A2 | 9/2001 |
| WO | 2002041753 | 5/2002 |
| WO | 0249536 A2 | 6/2002 |
| WO | 2004069059 A2 | 8/2004 |
| WO | 2005113035 A2 | 12/2005 |
| WO | 2008112435 A2 | 9/2008 |
| WO | 2010098804 A1 | 9/2010 |
| WO | 2010116074 A1 | 10/2010 |
| WO | 2013025493 A1 | 2/2013 |
| WO | 2014145012 A2 | 9/2014 |

OTHER PUBLICATIONS

Abstract of DE 19607451A published Sep. 4, 1997.
Official Communication dated Feb. 9, 2018 regarding U.S. Appl. No. 14/710,288, filed Apr. 7, 2017.
Examination Report dated Apr. 28, 2017 filed in New Zealand Patent Application No. 713123.
Official Communication dated Jul. 4, 2017 in German Patent Application No. 14710288.3-1664.
International Preliminary Report on Patentability for PCT/EP2014/055186 dated Sep. 15, 2015.
Examination Report dated Aug. 12, 2019 for NZ Patent Application No. 751704.
Azur, The Technology of Expansion. Terumo Interventional Systems. Downloaded on Feb. 21, 2013 from http://www.terumois.com/products/embolics/AZUR.aspx.
Ekeh et al., Complications arising from splenic artery embolisation: a review of an 11-year experience. The American Journal of Surgery, 205, 250-254, 2013.
Ryer et al. 2013, Comparison of outcomes with coils versus vascular plug embolisation of the internal iliac artery for endovascular aortoiliac aneurysm repair. Journal of Vascular Surgery, vol. 56, Issue 5, Nov. 2012, pp. 1239-1245.
Rastogi et al., Unintended coil migration into the right ventricle during the right ovarian vein coil embolisation. Vascular and Endovascular Surgery, Oct. 2011;45(7).
Marsh et al., Coil Protruding into the Common Femoral Vein Following Pelvic Venous Embolisation. Cardiovascular Interventional Radiology (2008) 31 :435-438.
Beddy et al., Testicular varicoceles. Clinical Radiology (2005) 60, 1248-1255.
Beecroft et al., Percutaneous varicocele embolisation. Canadian Urological Association Journal. Sep. 2007, vol. 1, Issue 3.
Kessel et al., Transcatheter Embolisation and Therapy. Springer ISBN 978-1-84800-896-0. Published 2010.
Balian et al. Pelviperineal venous insufficiency and varicose veins of the lower limbs. Phlebolymphology. 2008;15(1):17-26.

(56) References Cited

OTHER PUBLICATIONS

Messé et al., Atrial septal abnormalities (PFO, ASD, and ASA) and risk of cerebral emboli in adults. Downloaded on Feb. 22, 2013 from www.uptodate.com.
St. John Sutton et al., Devices for percutaneous closure of a secundum atrial septal defect. Downloaded on Feb. 22, 2013 from www.uptodate.com.
Letourneau-Guillon et al., Embolisation of Pulmonary Arteriovenous Malformations with Amplatzer Vascular Plugs: Safety and Midterm Effectiveness. Journal of Vascular and Interventional Radiology, vol. 21, Issue 5, pp. 649-656, May 2010.
Wang et al., The Amplatzer Vascular Plug: A Review of the Device and its Clinical Applications, CardioVascular and Interventional Radiology, Aug. 2012, vol. 35, Issue 4, pp. 725-740.
Yoo et al., Preoperative portal vein embolisation using an amplatzer vascular plug. European Radiology (2009) 19: 1054-1061.
Pelage et al. What is Azur Hydrocoil and How Does it Work? Presented at Society of Interventional Radiology, 2011.
Van Der Vleuten et al., Embolisation to treat pelvic congestion syndrome and vulval varicose veins. International Journal of Gynecology and Obstetrics 118 (2012) 227-230.
Bleday et al., Treatment of haemorrhoids, Sep. 24, 2012. Downloaded on Feb. 22, 2013 from www.uptodate.com.
Nyström et al., Randomized clinical trial of symptom control after stapled anopexy or diathermy excision for haemorrhoid prolapse. Br J Surg. 2010;97(2):167.
A M Gardner, Inferior vena caval interruption in the prevention of fatal pulmonary embolism, American Heart Journal (impact factor: 4.65). Jul. 1978; 95(6):679-82.
Hollier, MD, Shaggy aorta syndrome and disseminated atheromatous embolisation. In: Bergan JJ, Yao JST, editors Aortic surgery Philadelphia: WB Saunders; 1989. p. 189-94.
Chung EM, Hague JP, Evans DH., Revealing the mechanisms underlying embolic stroke using computational modelling, Phys Med Biol. Dec. 7, 2007;52(23):7153-66. Epub Nov. 19, 2007.
Pyung et al., Successful percutaneous endovascular retrieval of a coil in the left ventricle which migrated during embolisation for pulmonary arteriovenous malformation. International Journal of Cardiology 163 (2013) e33-e35.
Office Action pertaining to Canadian Patent Application No. 2,906,996, dated Jan. 30, 2020.
Office Action pertaining to Brazilian Patent Application No. BR112015022634-5, dated Dec. 30, 2019.
Office Action pertaining to Australian Patent Application No. 2019201270, dated Feb. 18, 2020.
Notice of Reexamination pertaining to corresponding Chinese Patent Application No. 201480028175.1, dated Apr. 28, 2020.

\* cited by examiner

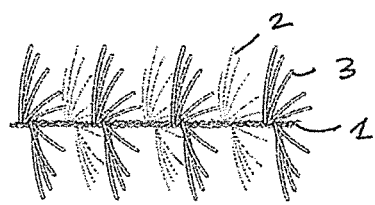
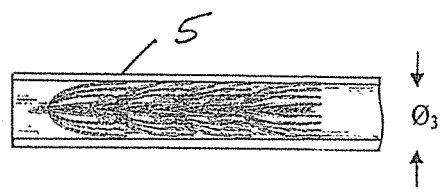
Fig. 1  Fig. 2
Fig. 3
Fig. 4
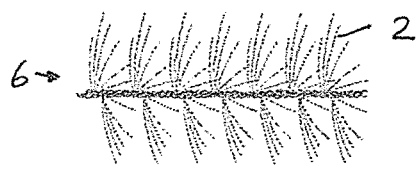
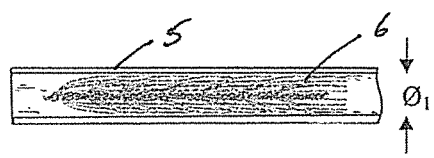
Fig. 5  Fig. 6
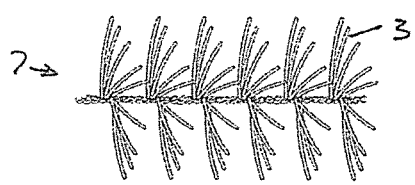
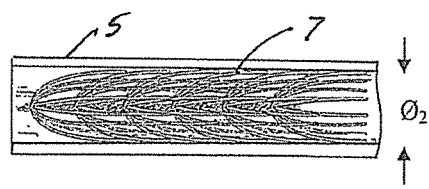
Fig. 7  Fig. 8

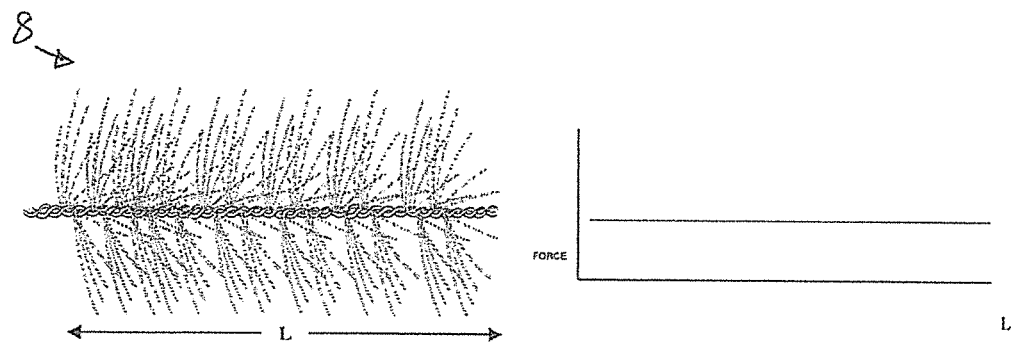
Fig. 9          Fig. 10
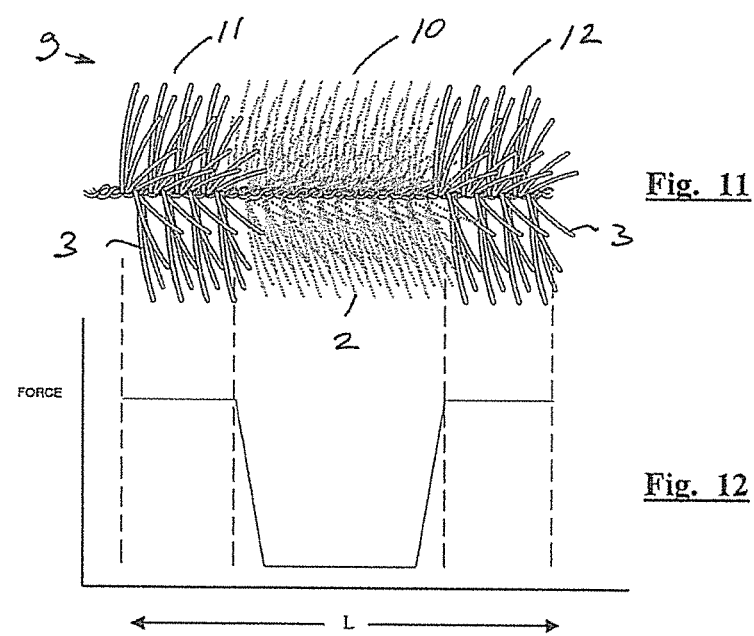
Fig. 11
Fig. 12

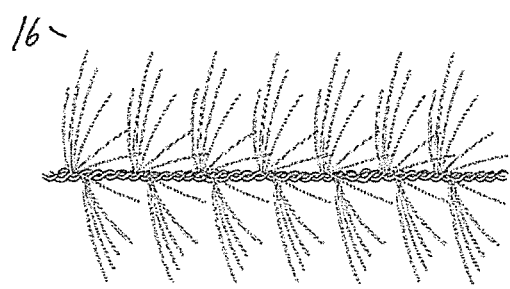
5 minutes   Fig. 17a
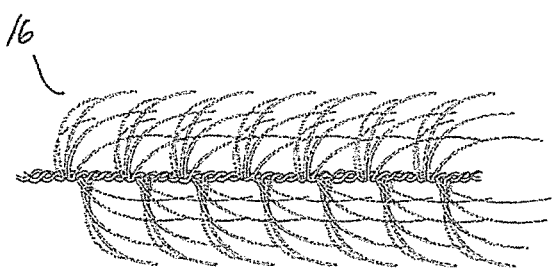
20 minutes   Fig. 17b
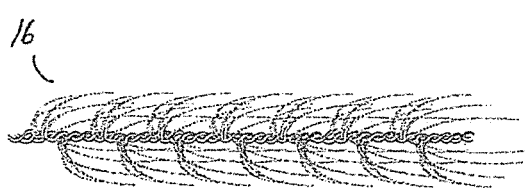
5 days   Fig. 17c (vi)

(vii)

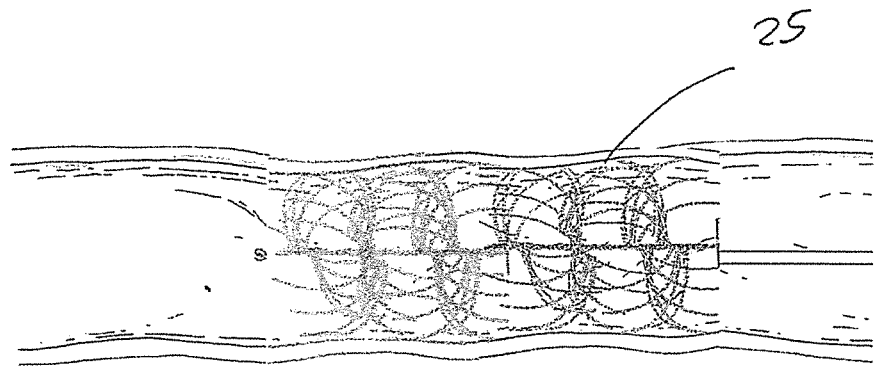
Fig. 34
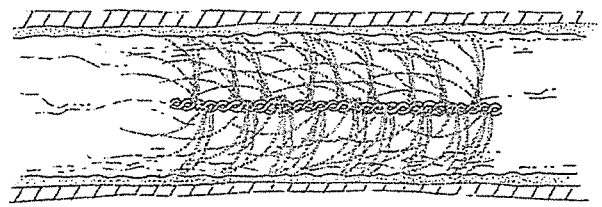
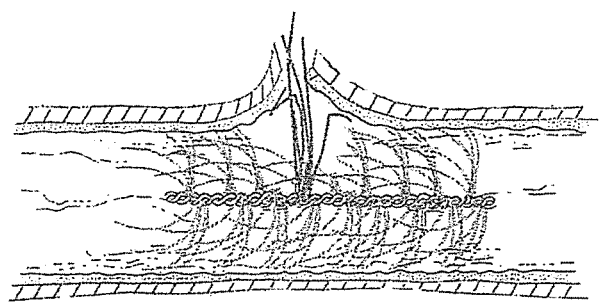
Fig. 35

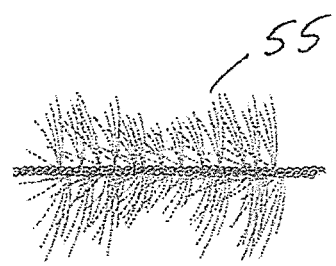
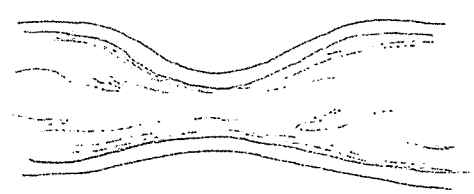
Fig. 37
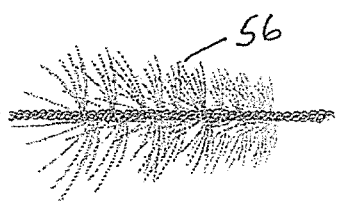
Fig. 38
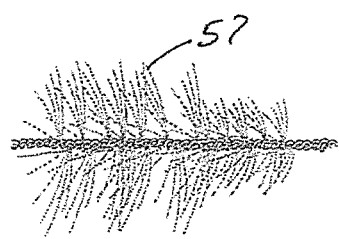
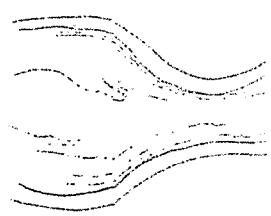
Fig. 39
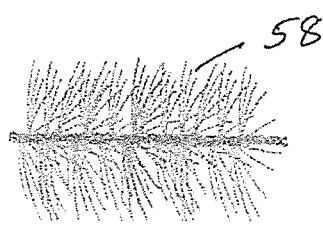
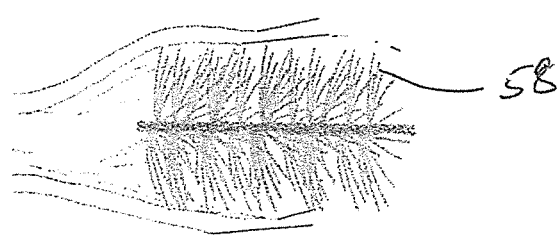
Fig. 40

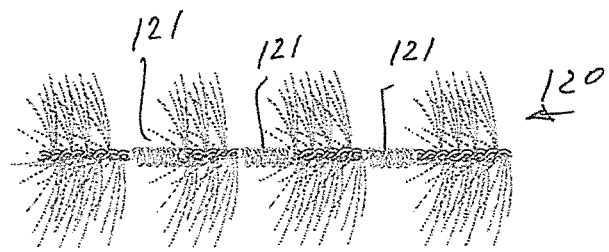
Fig. 86
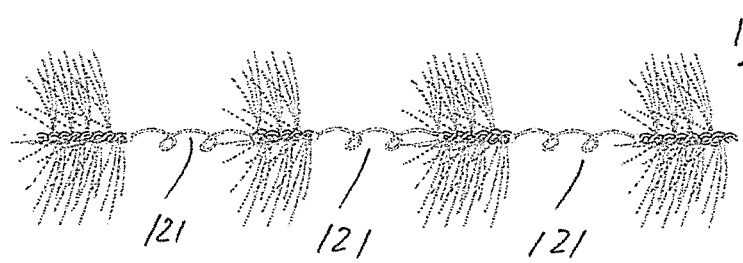
Fig. 87
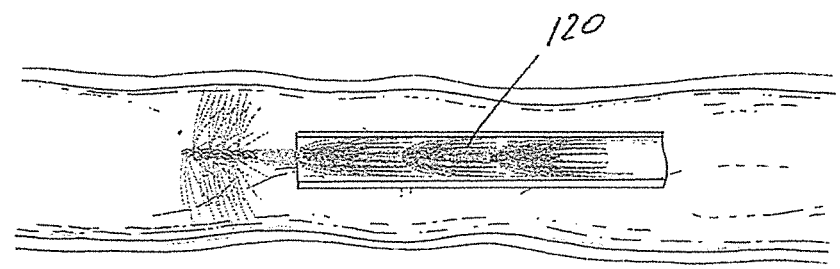
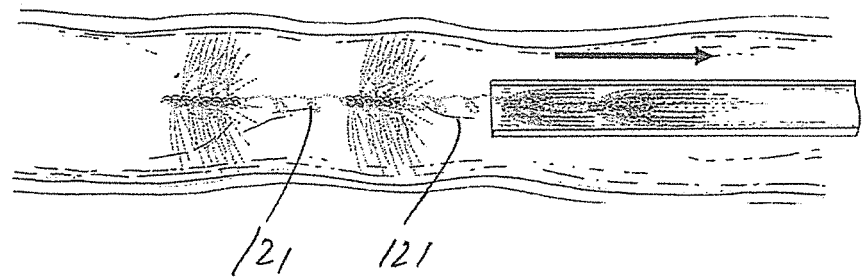
Fig. 88

Embolus travelling distally towards pedal arteries

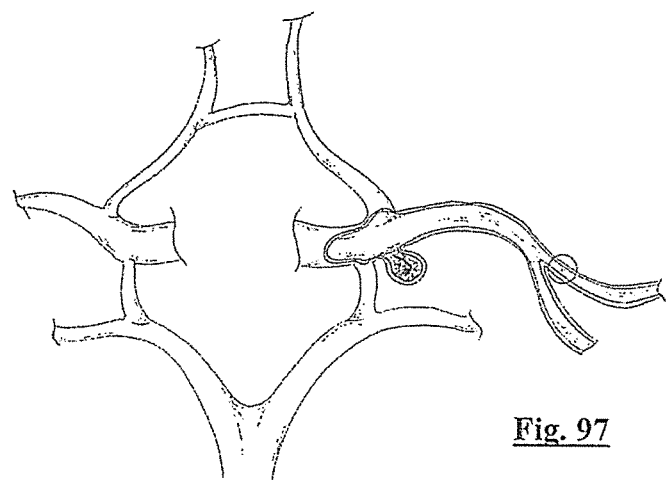
Fig. 97
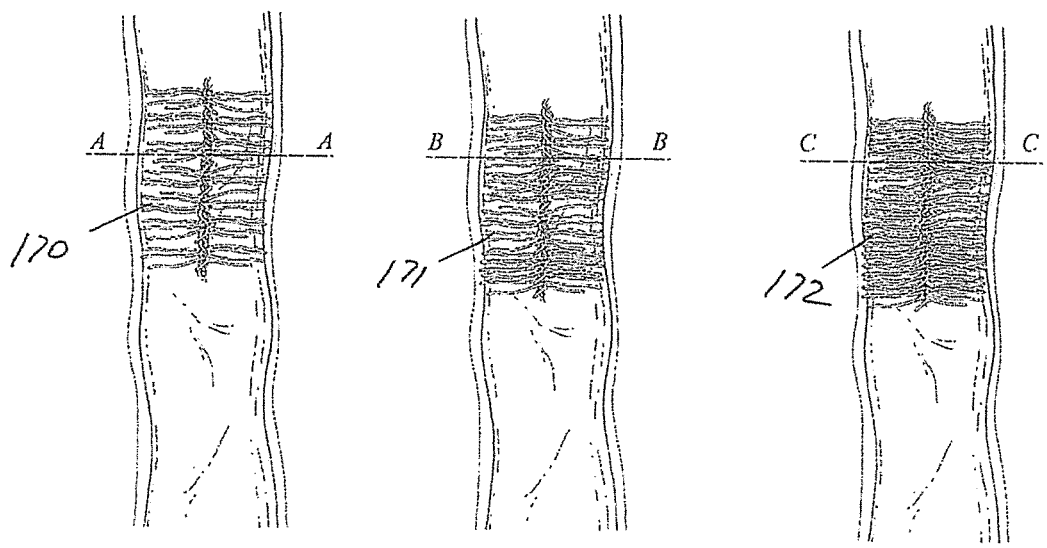
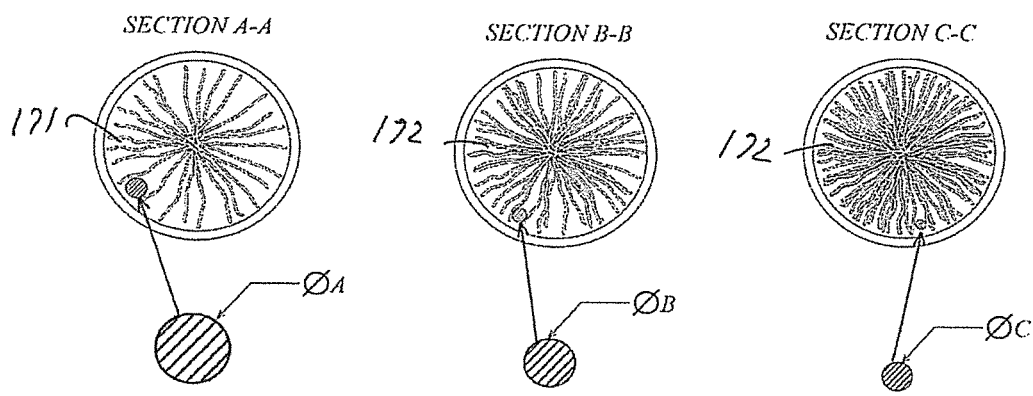
Fig. 98  Fig. 99  Fig. 100

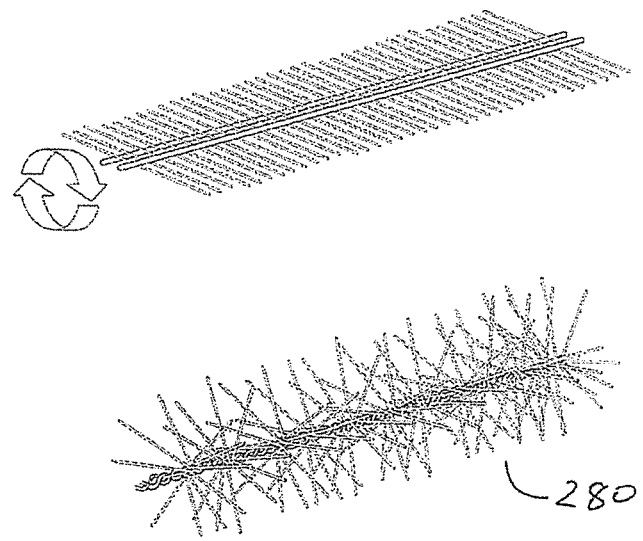
Fig. 113
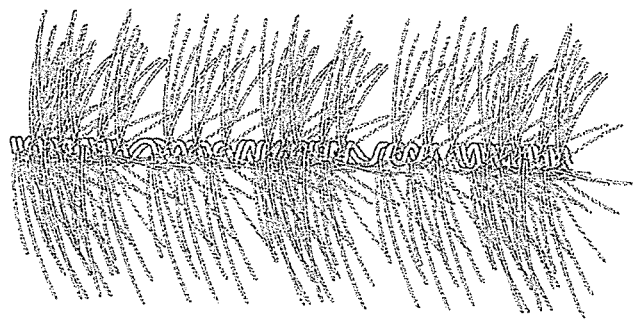
Fig. 114

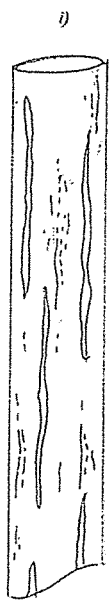
Fig. 121
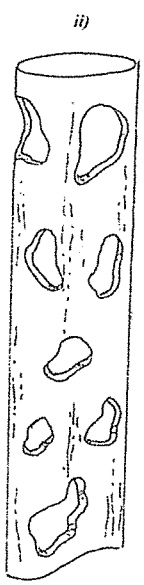
Fig. 122
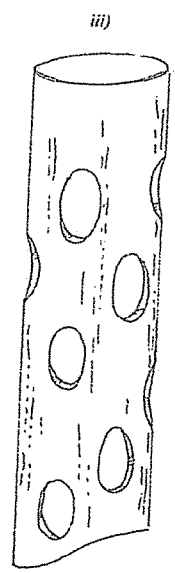
Fig. 123
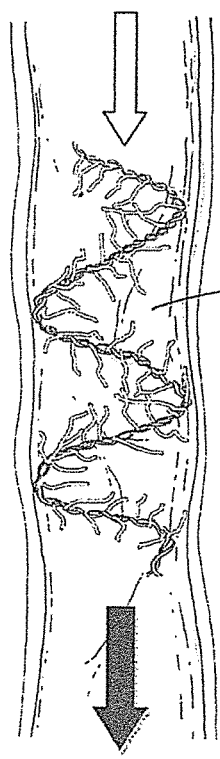
Blood Flow
Blood Flow + Therapeutic
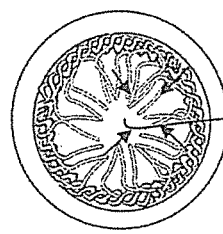
view from above
Fig. 124

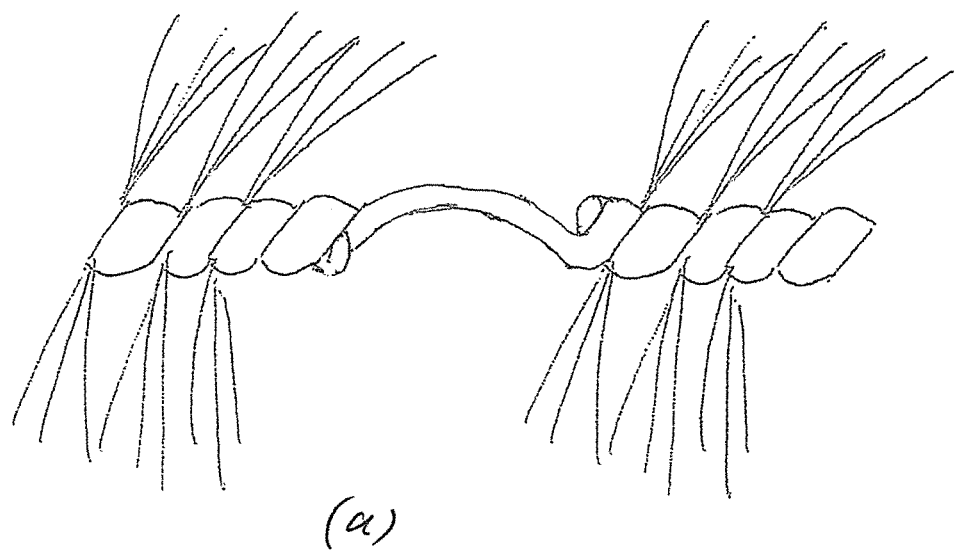
(a)
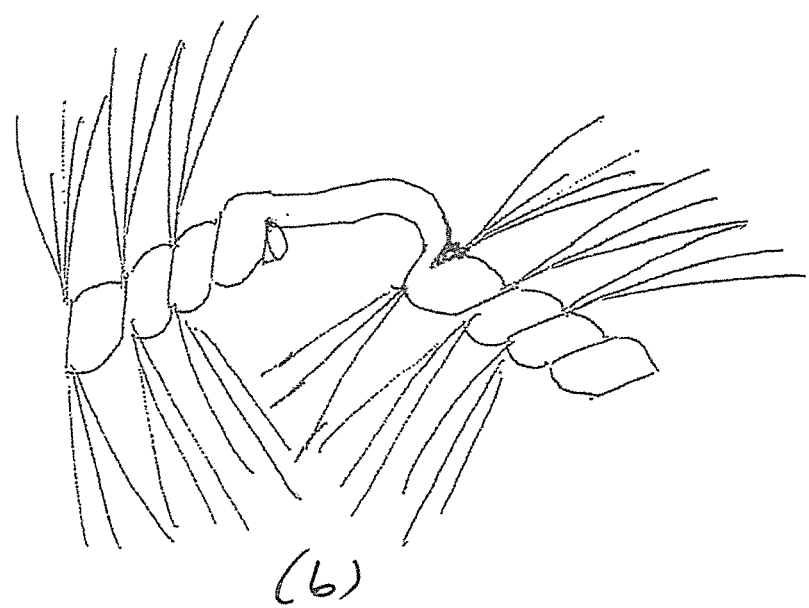
(b)
Fig. 131

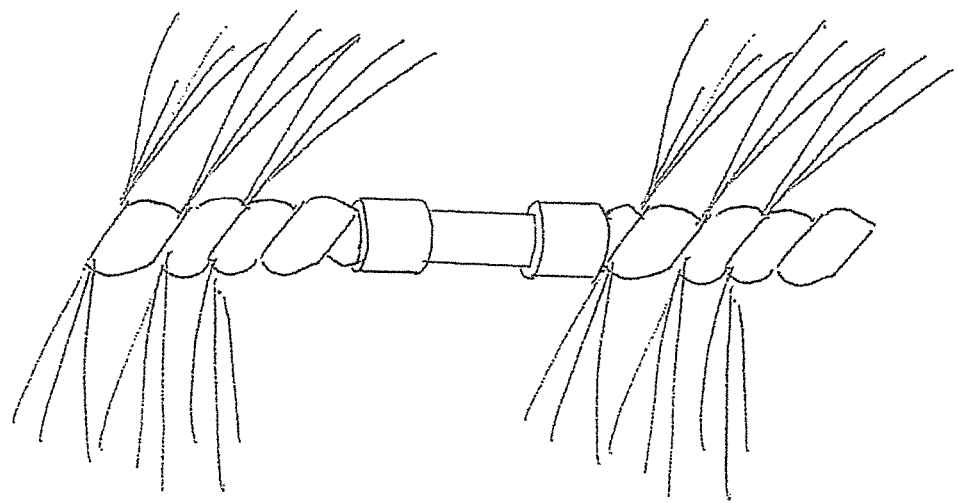
(a)
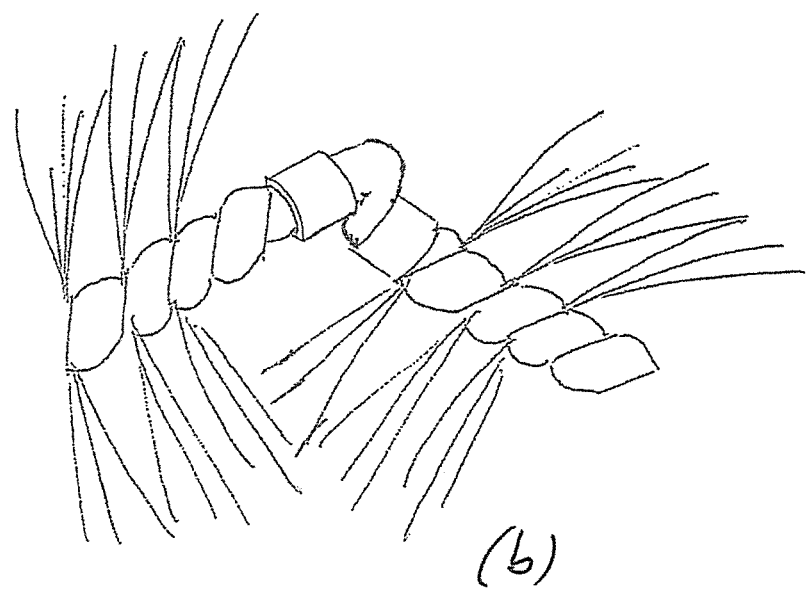
(b)
Fig. 132

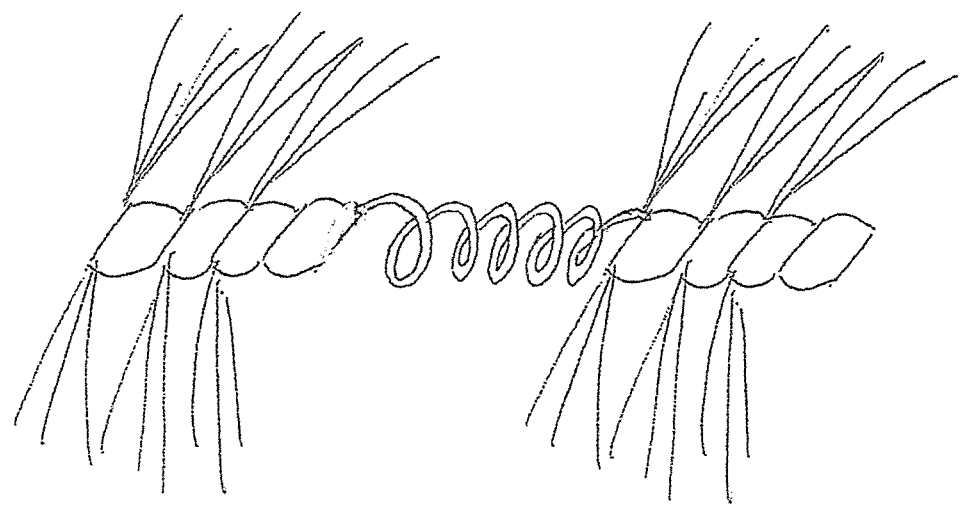
(a)
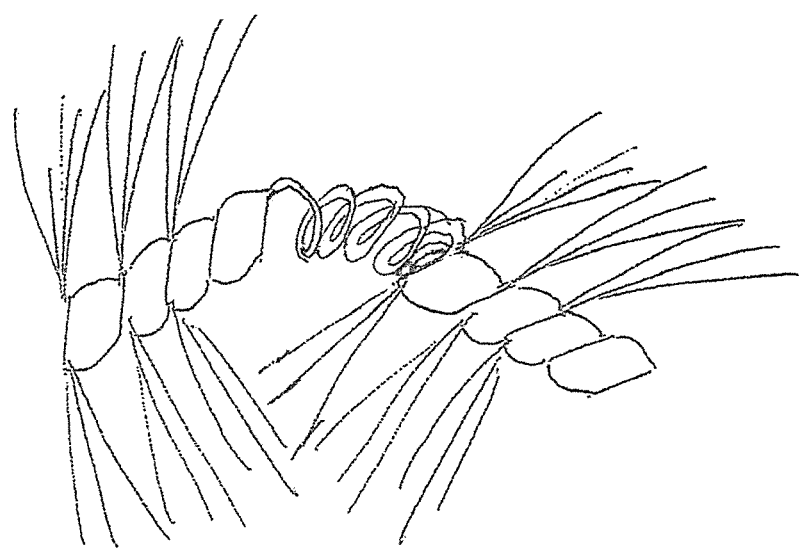
(b)
Fig. 133

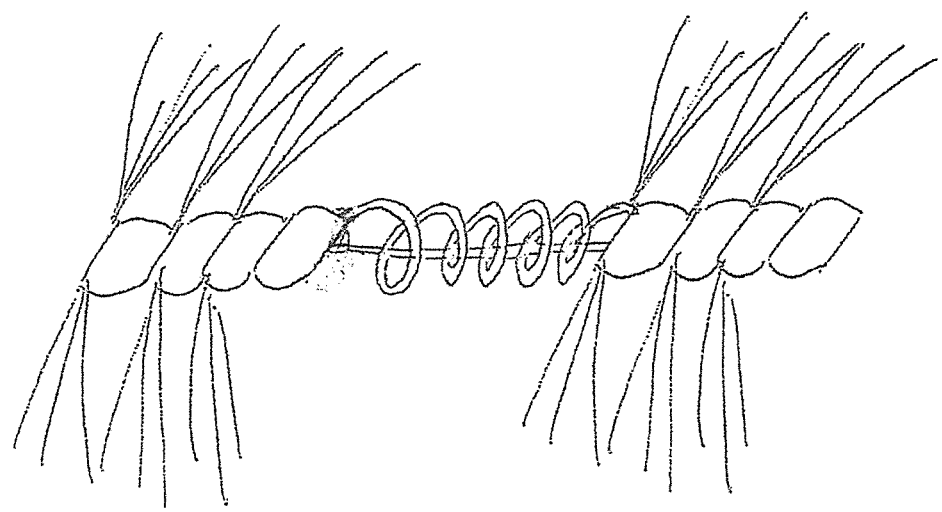
(a)
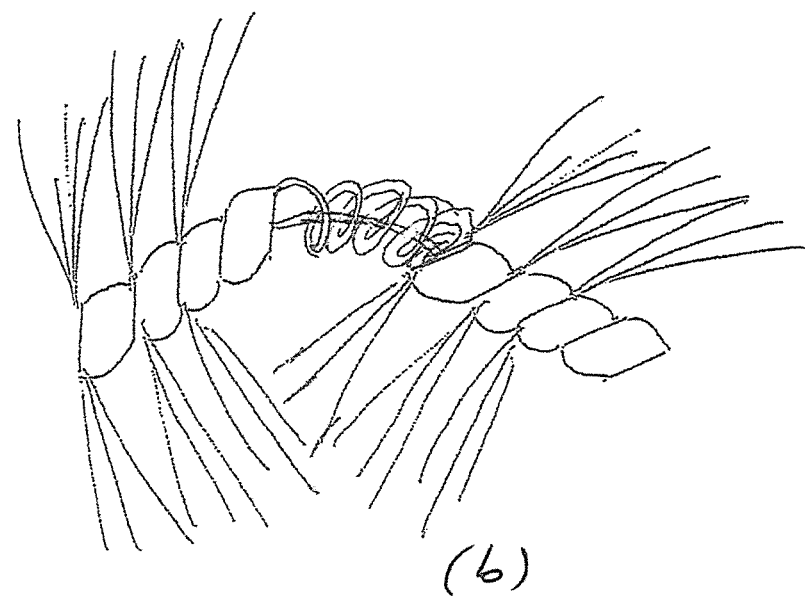
(b)
Fig. 134

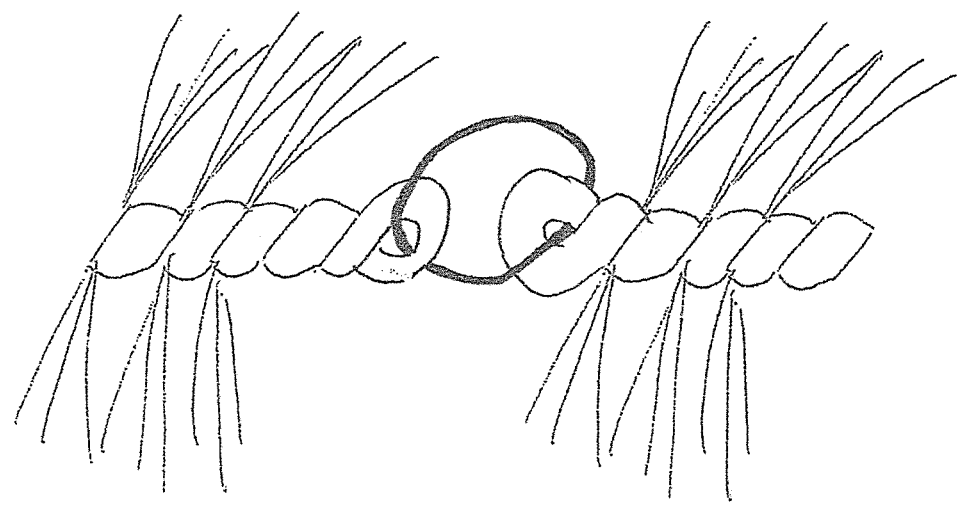
(a)
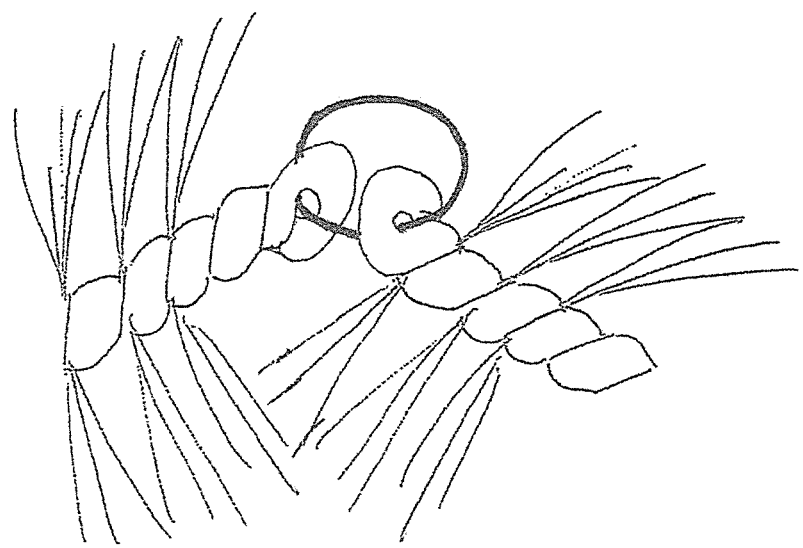
(b)
Fig. 135

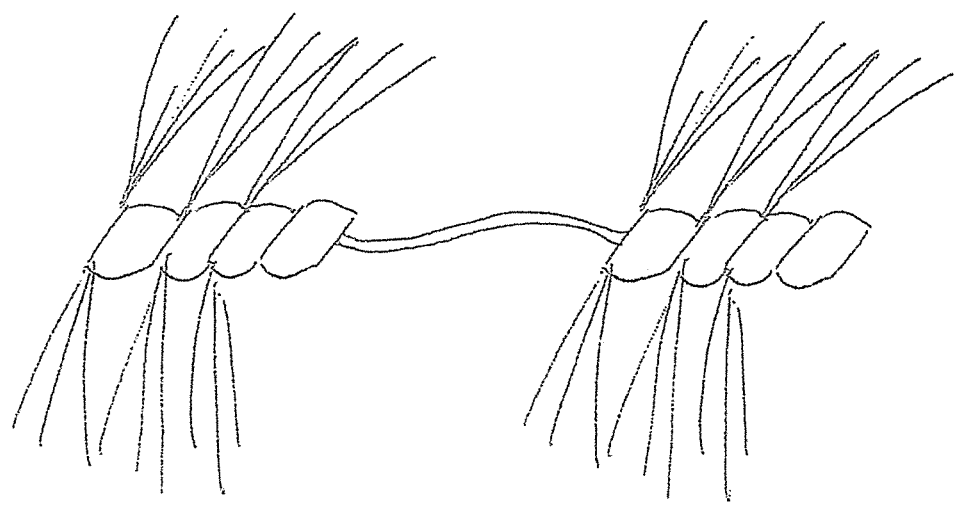
(a)
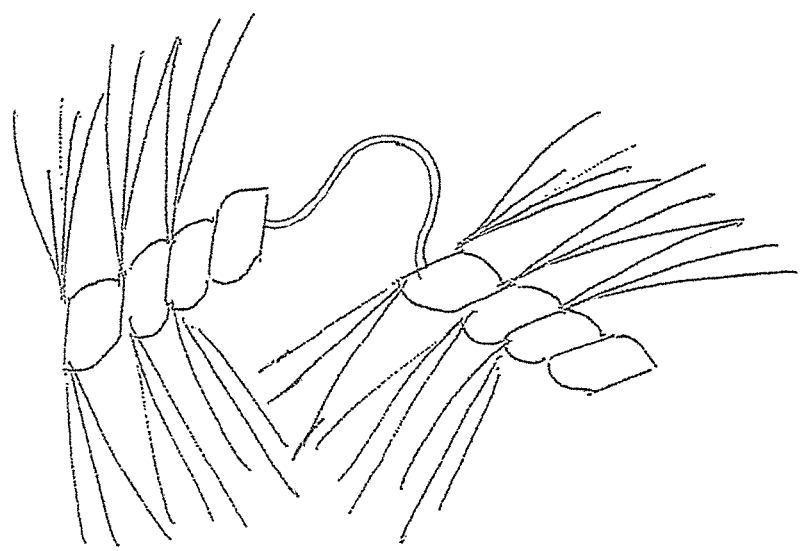
(b)
Fig. 136

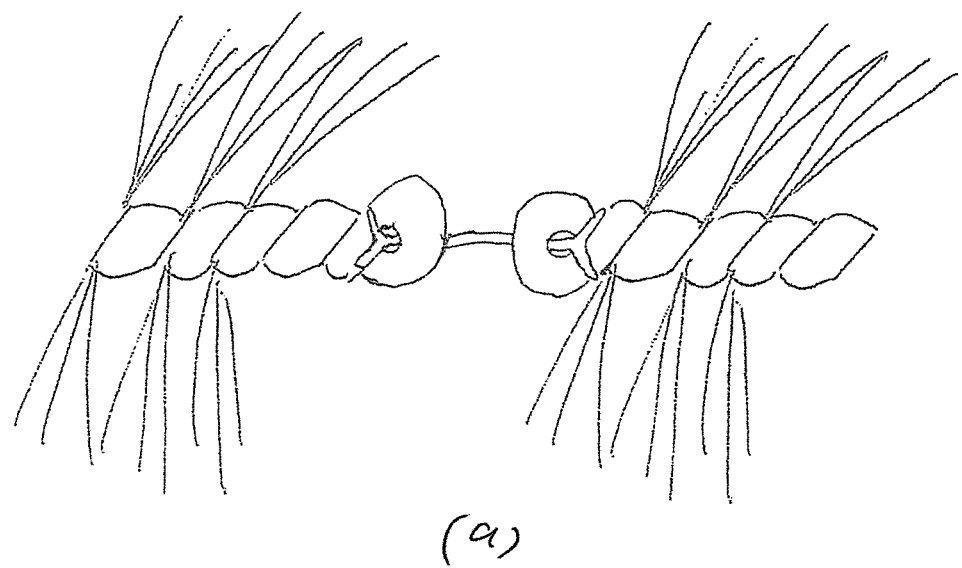
(a)
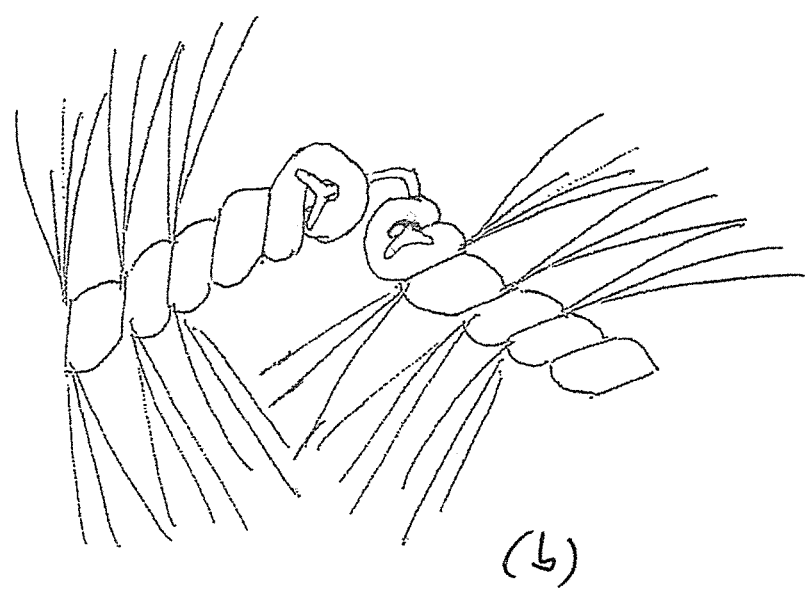
(b)
Fig. 137

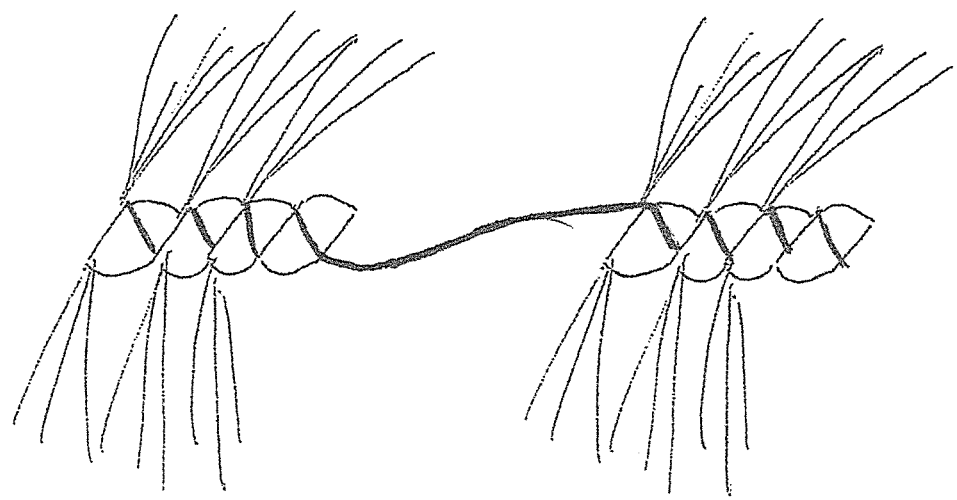
(a)
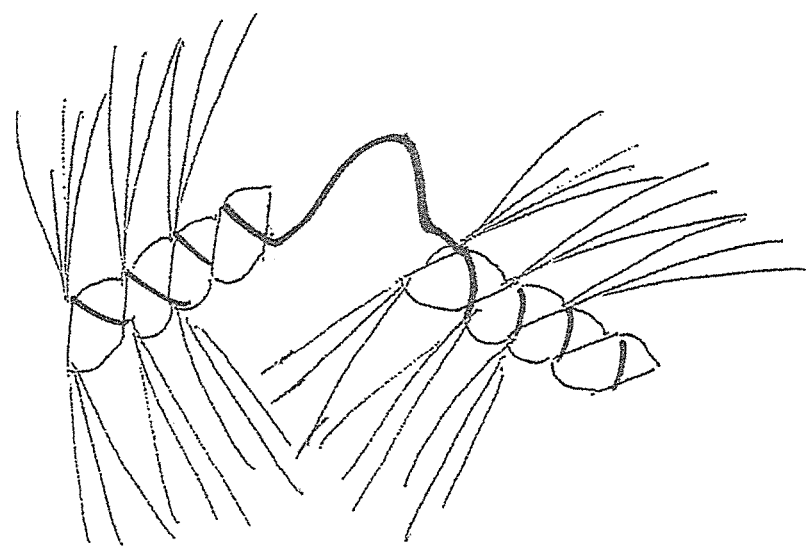
(b)
Fig. 138

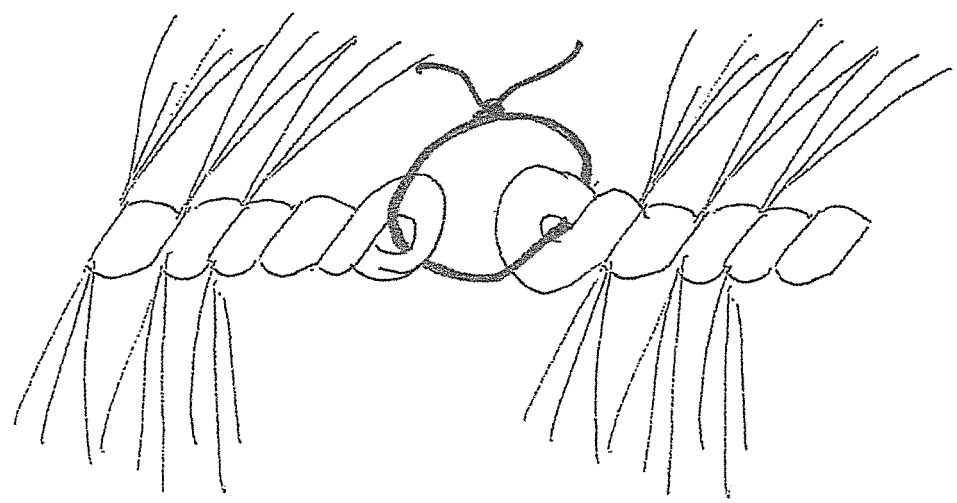
(a)
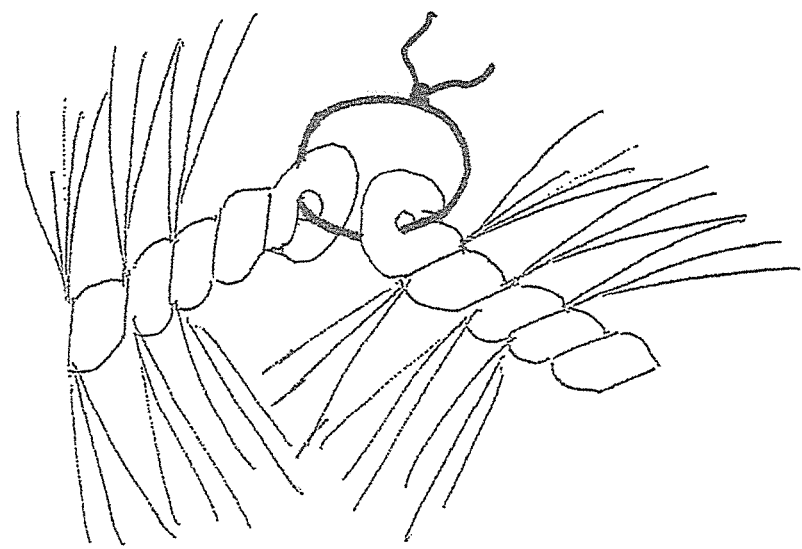
(b)
Fig. 139

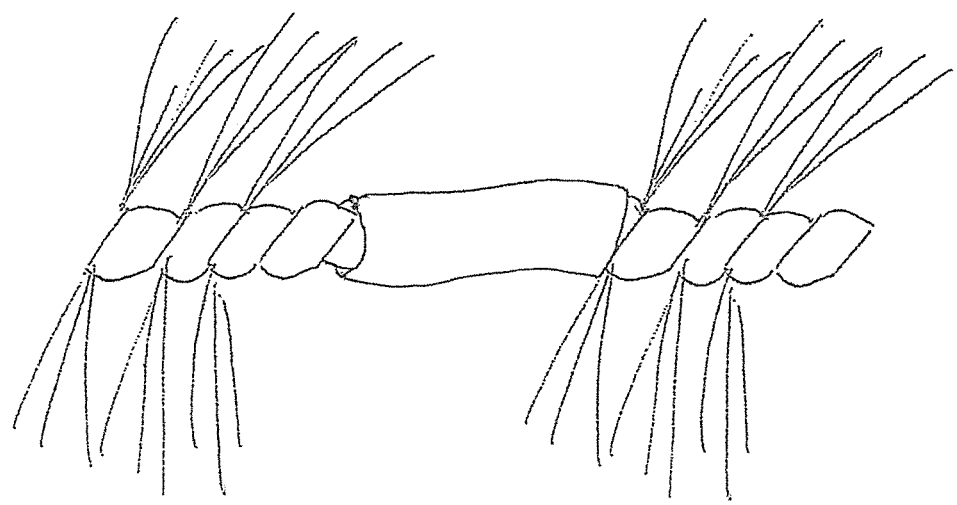
(a)
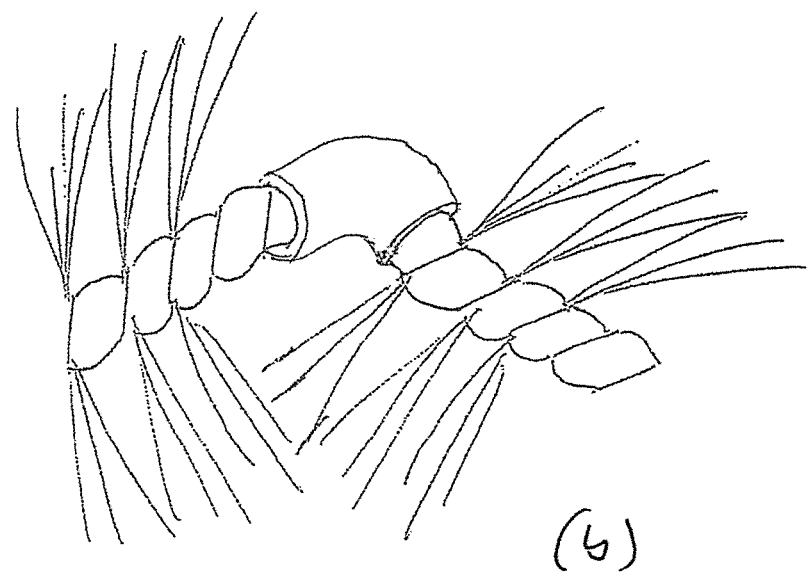
(b)
Fig. 140

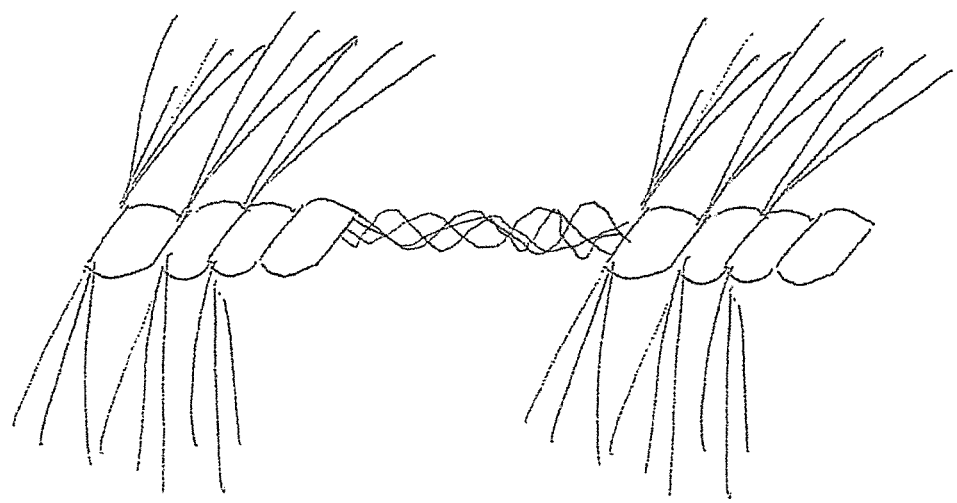
(a)
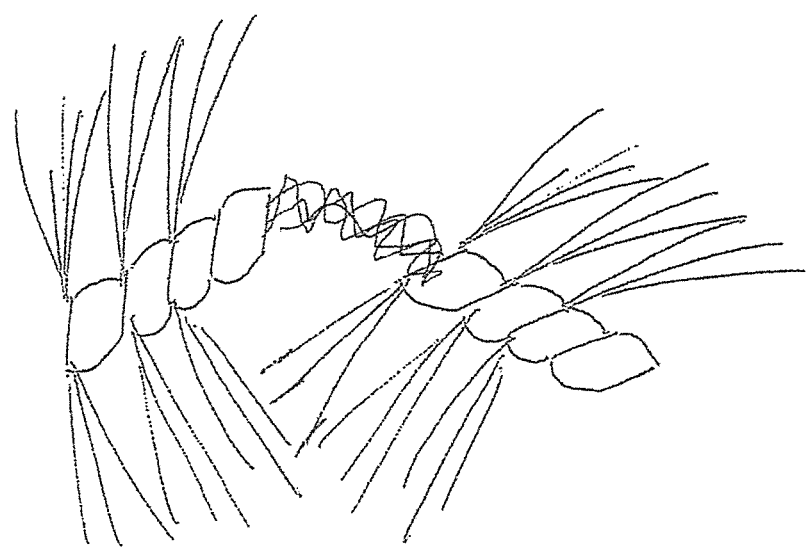
(b)
Fig. 141

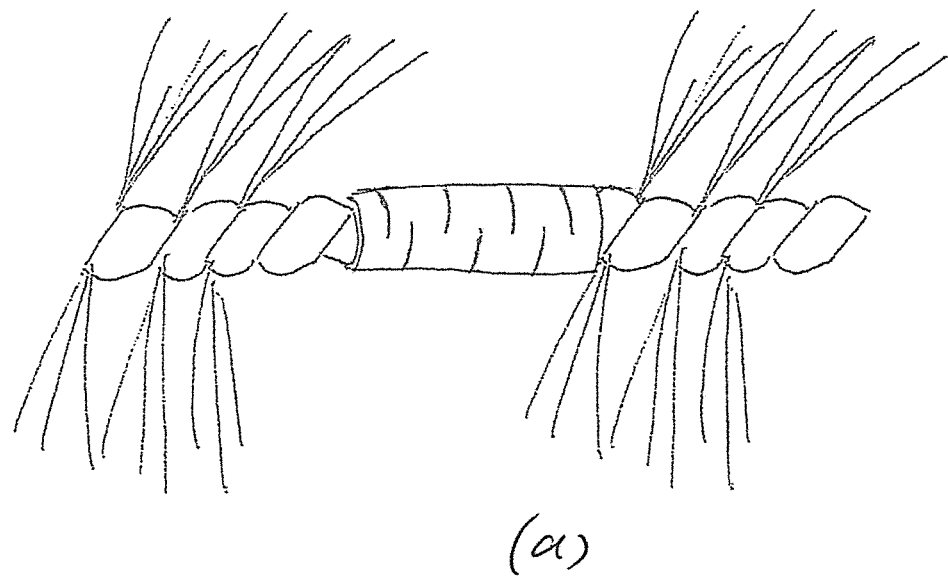
(a)
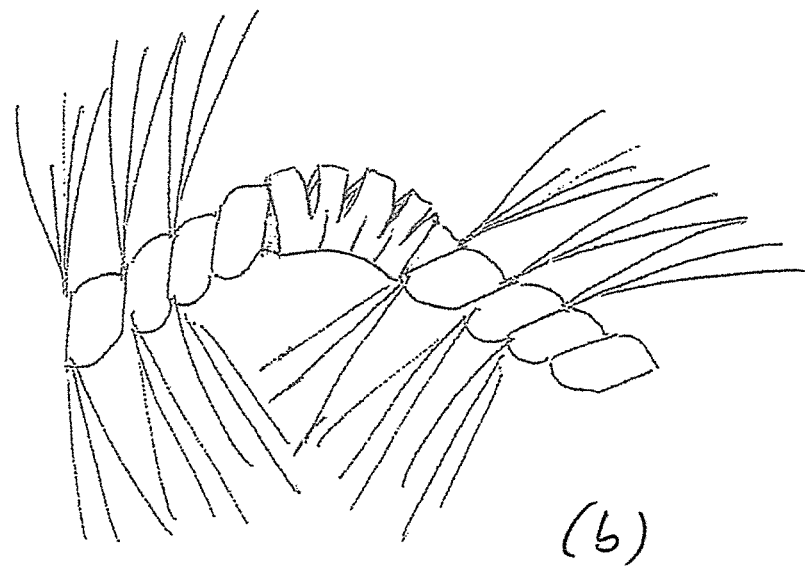
(b)
Fig. 142

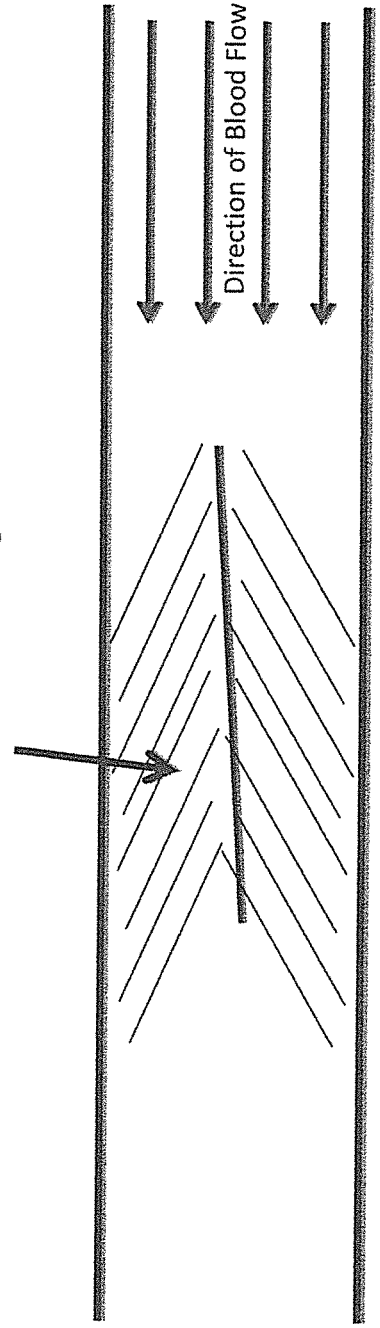
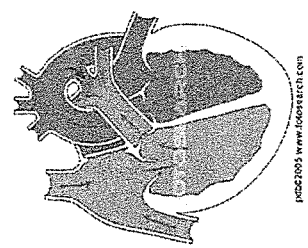
Fig. 143

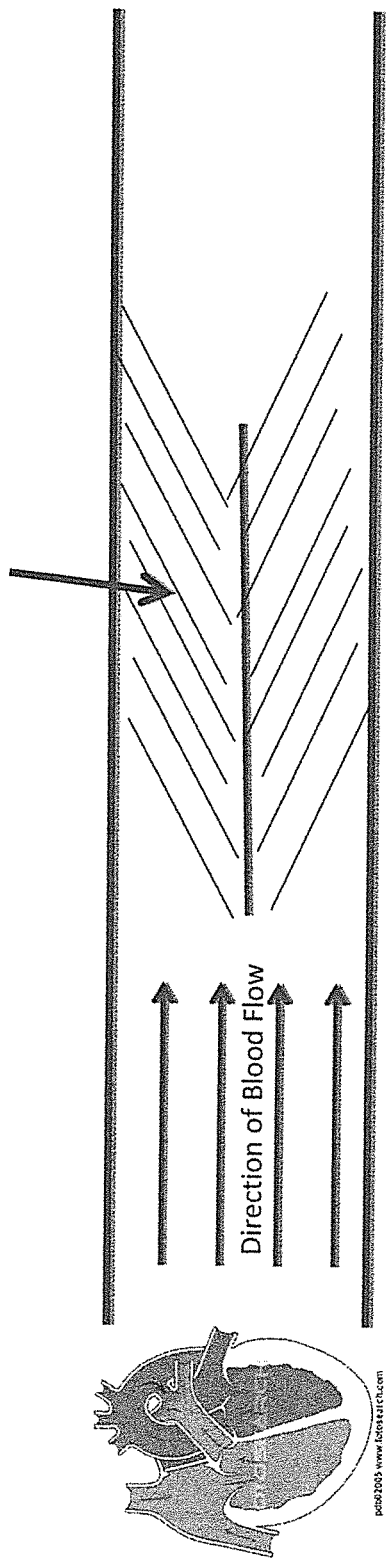

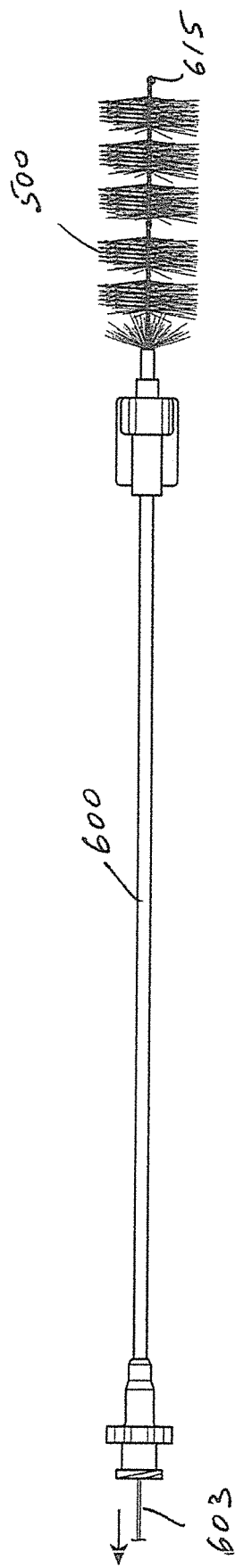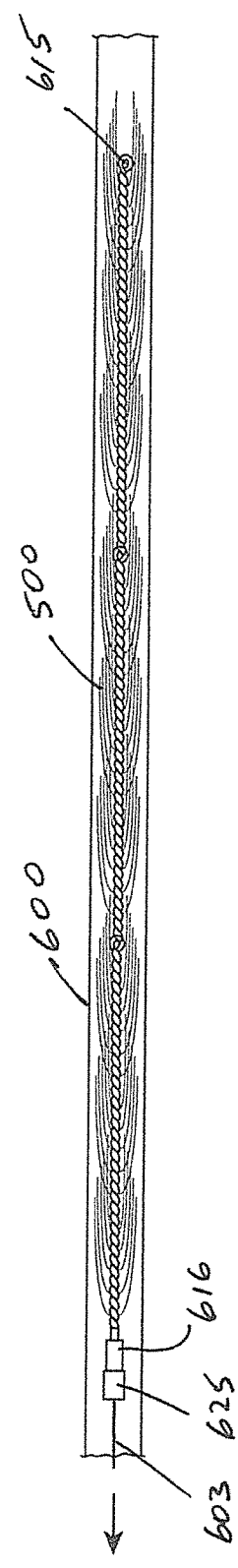
Fig. 149
Fig. 150

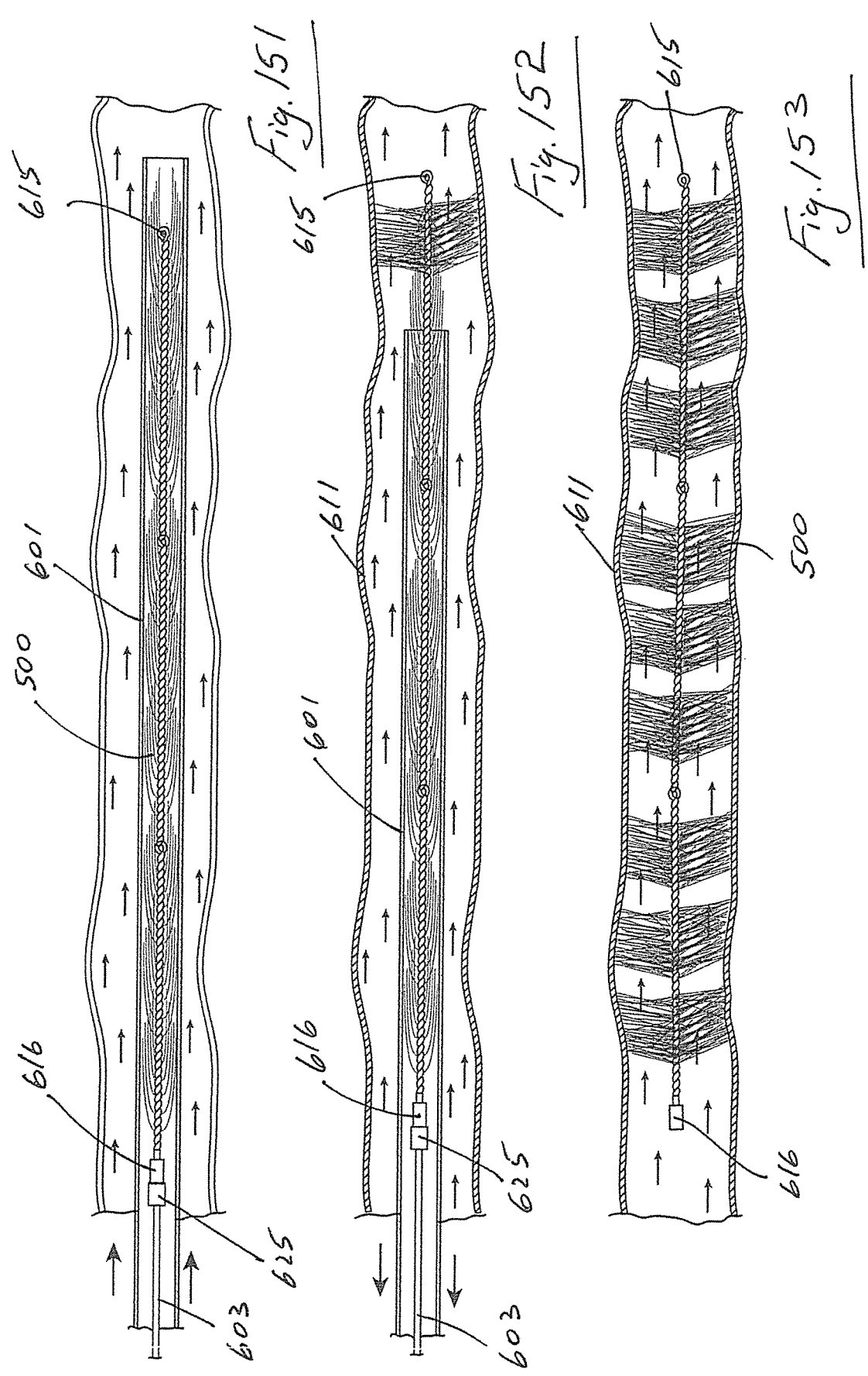

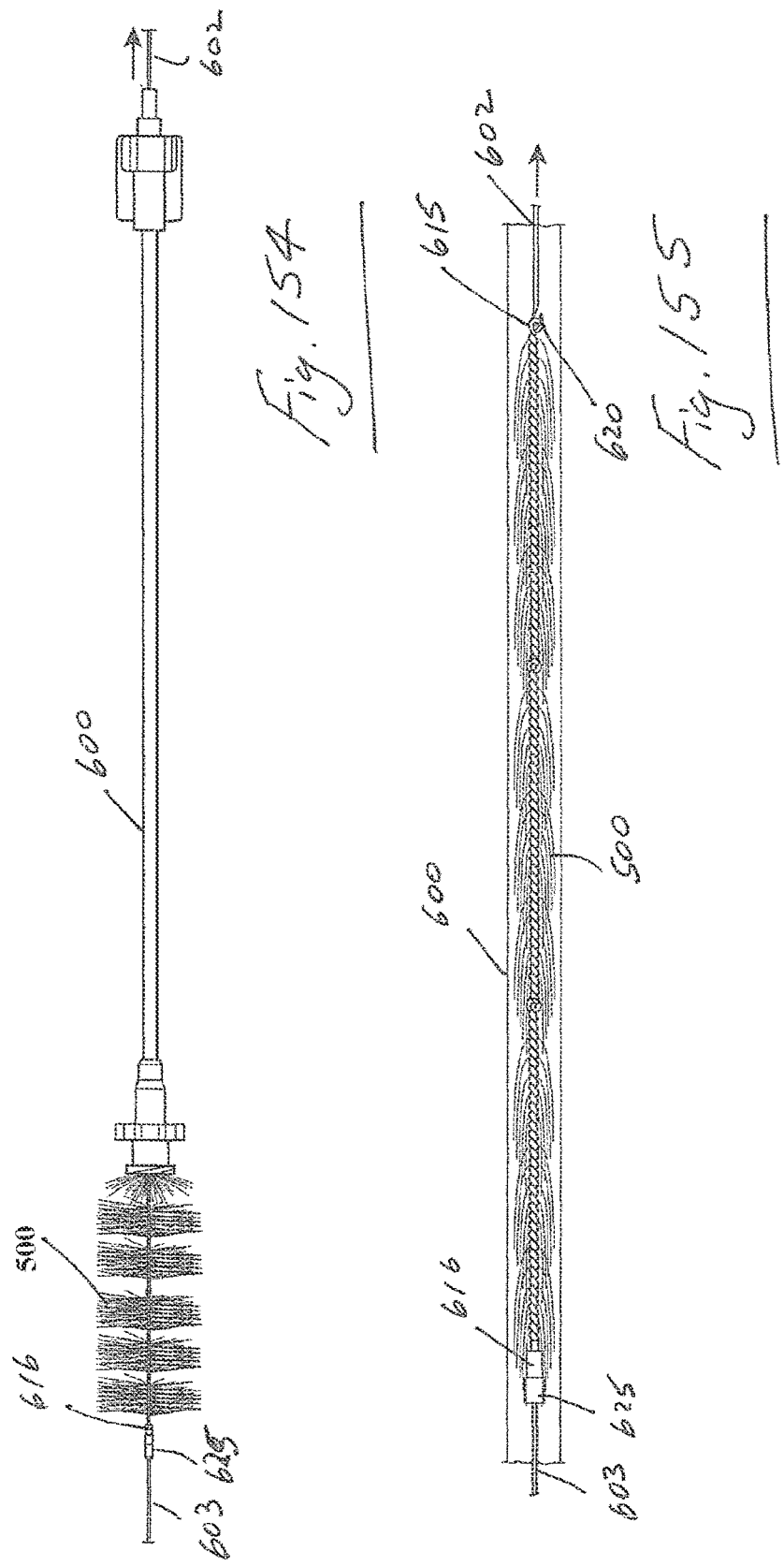

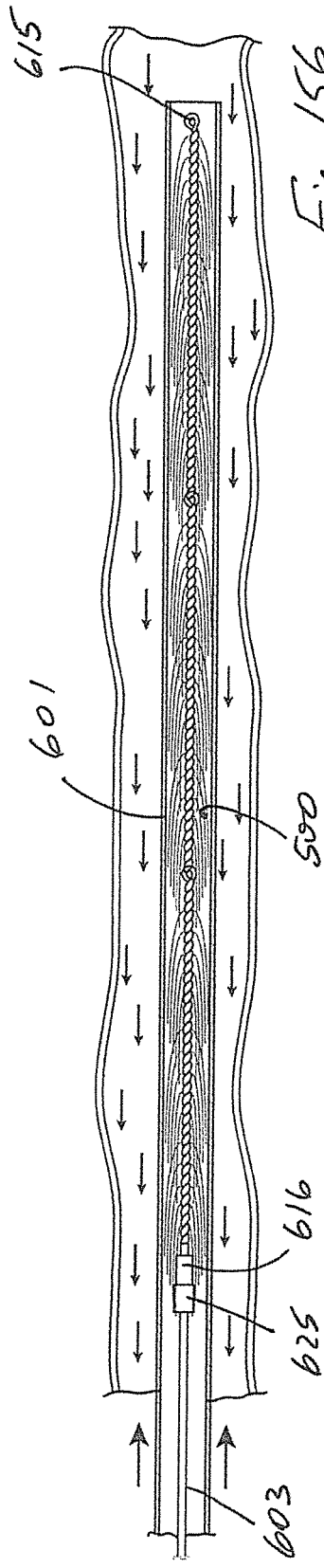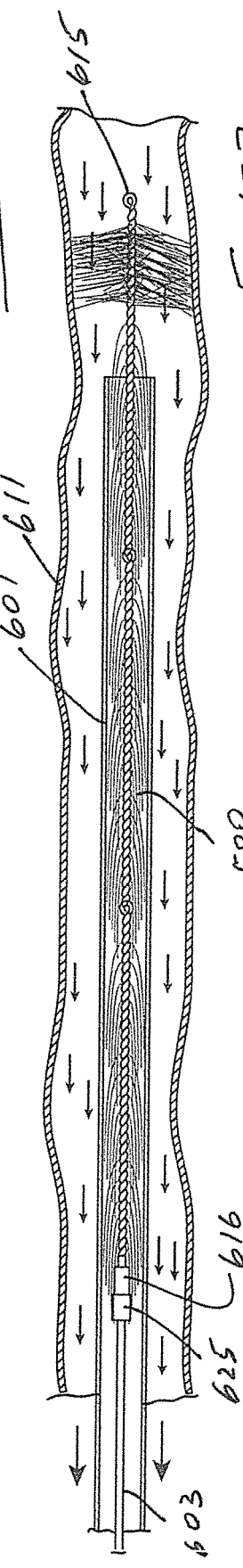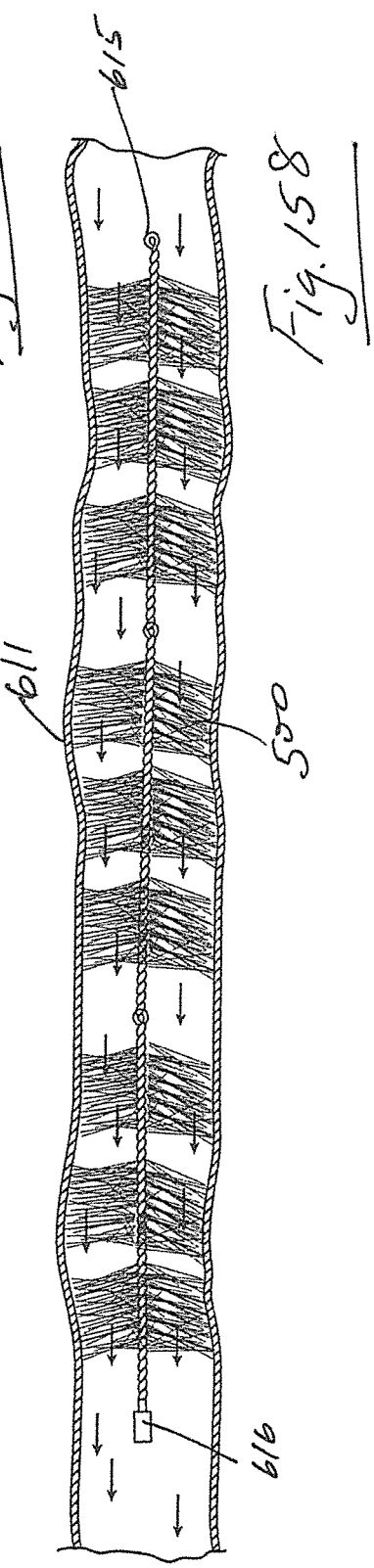

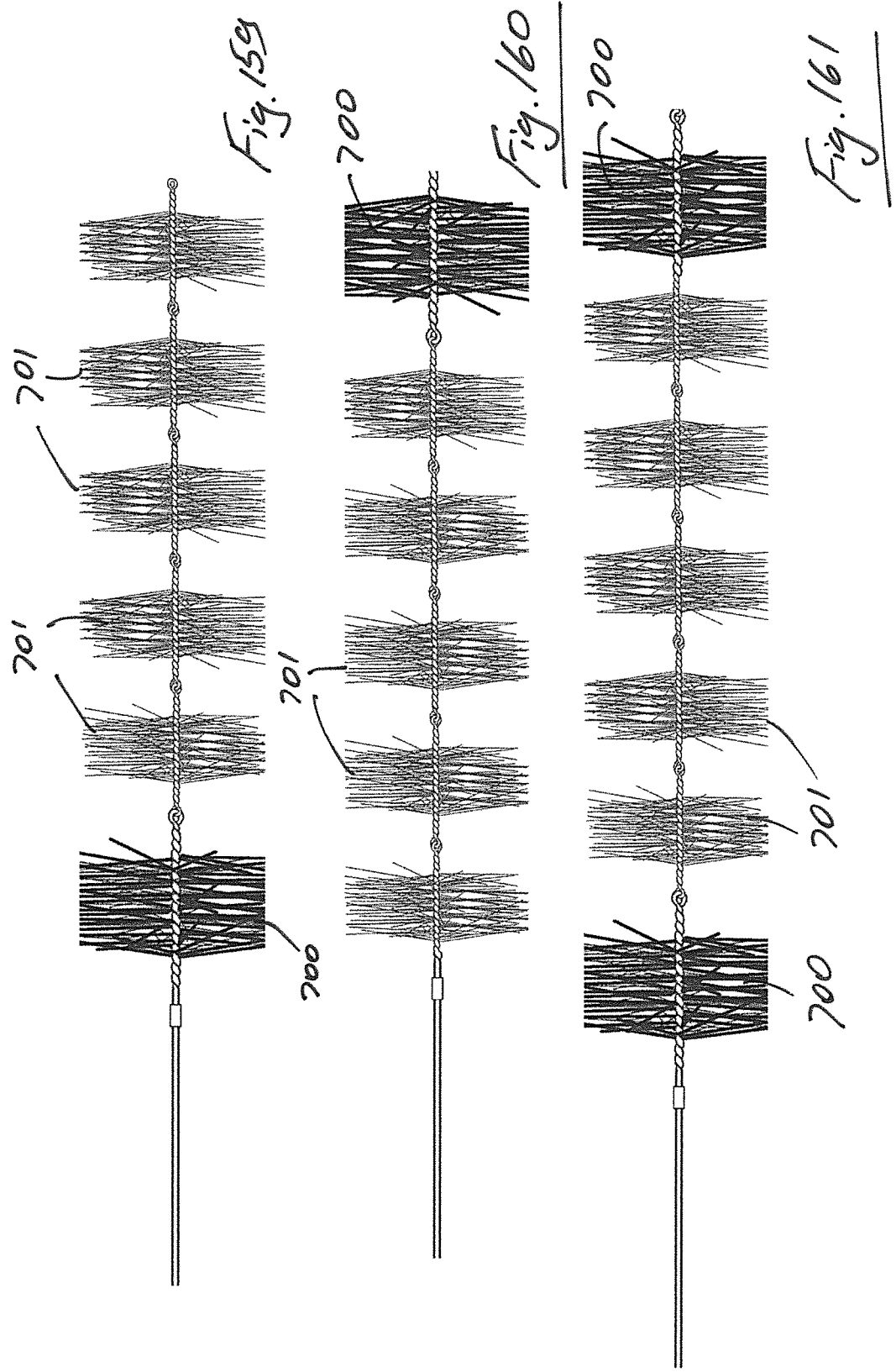

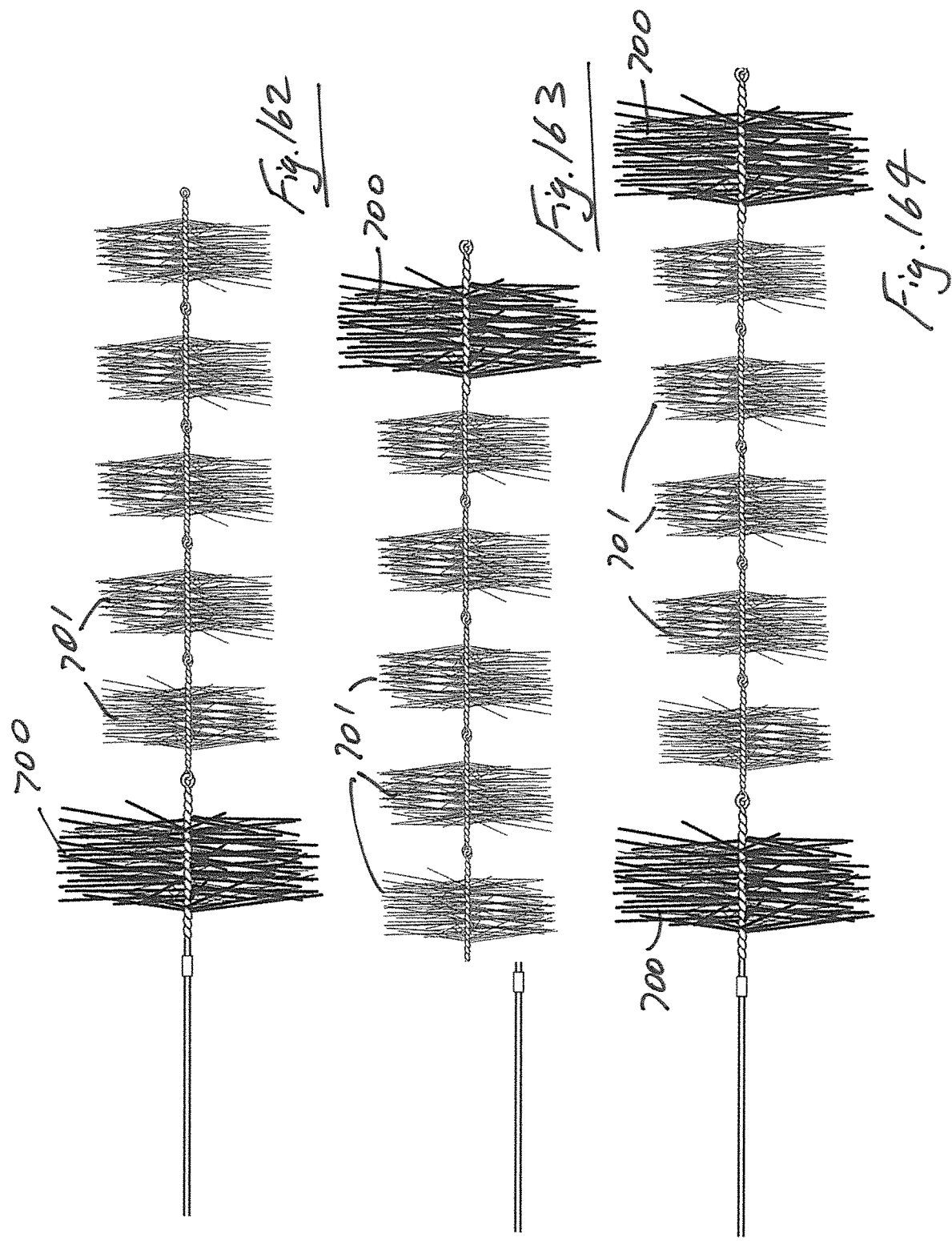

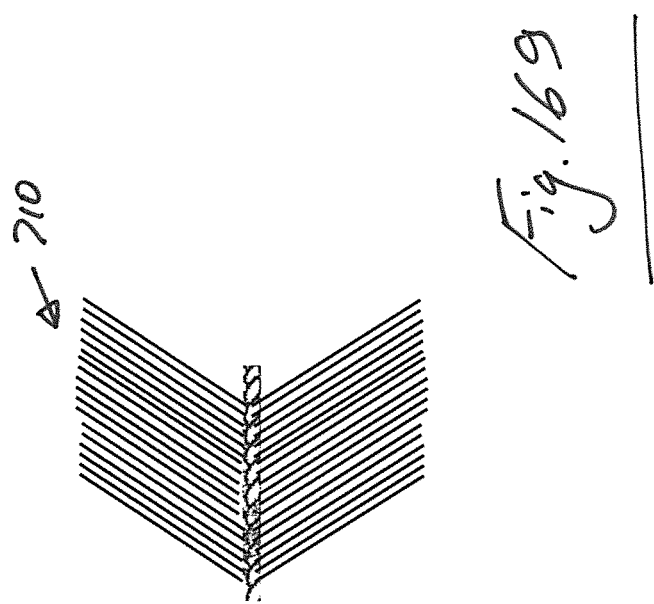

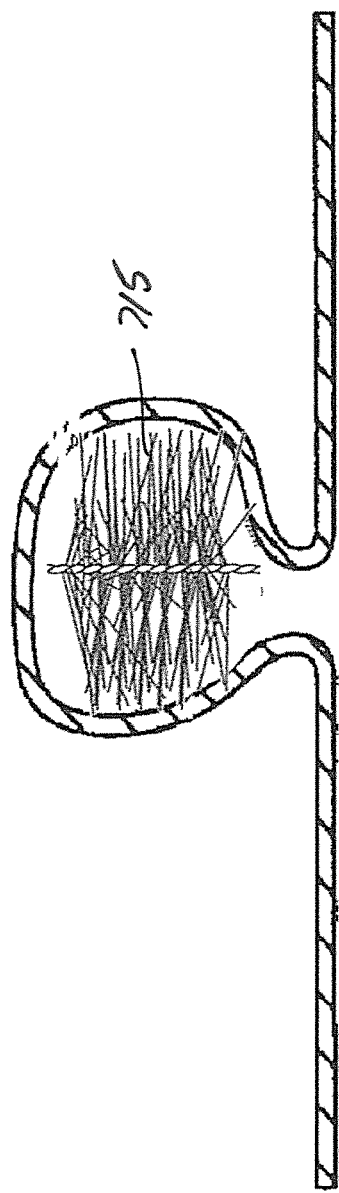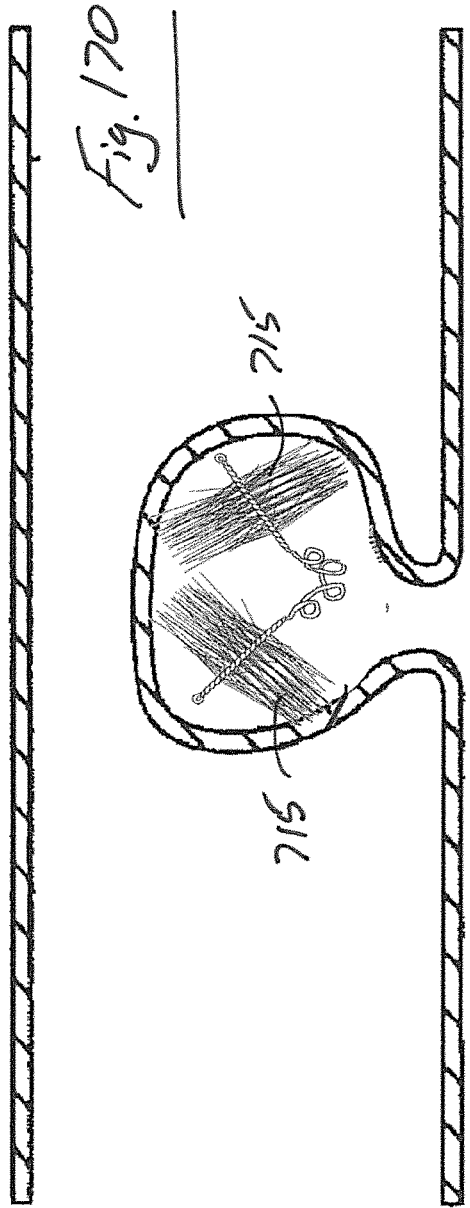

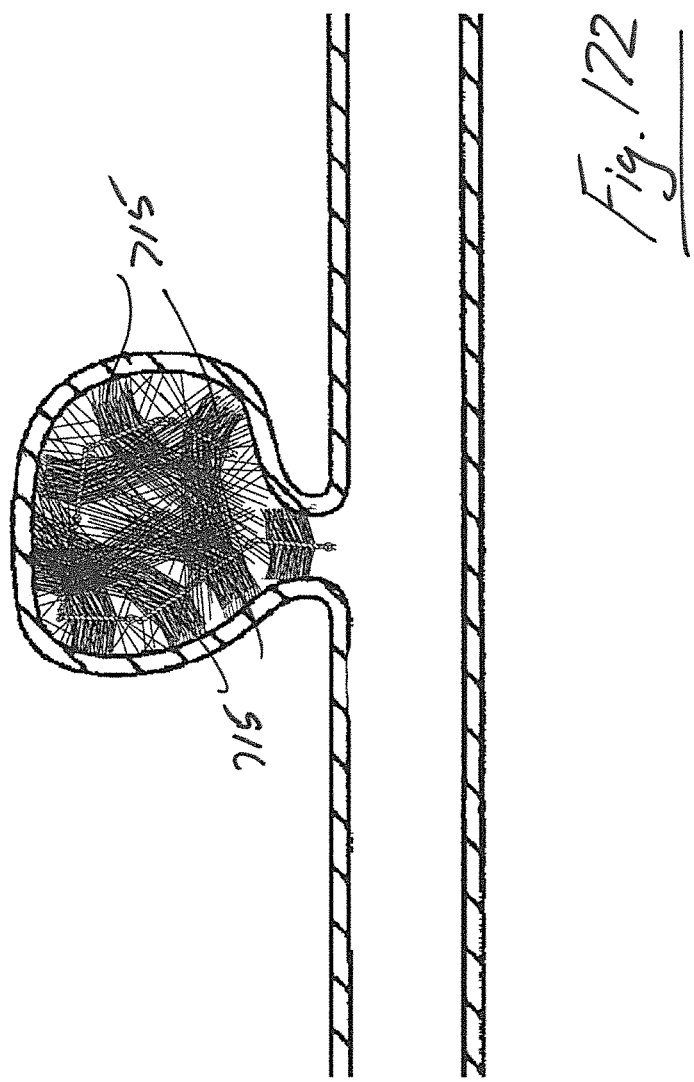

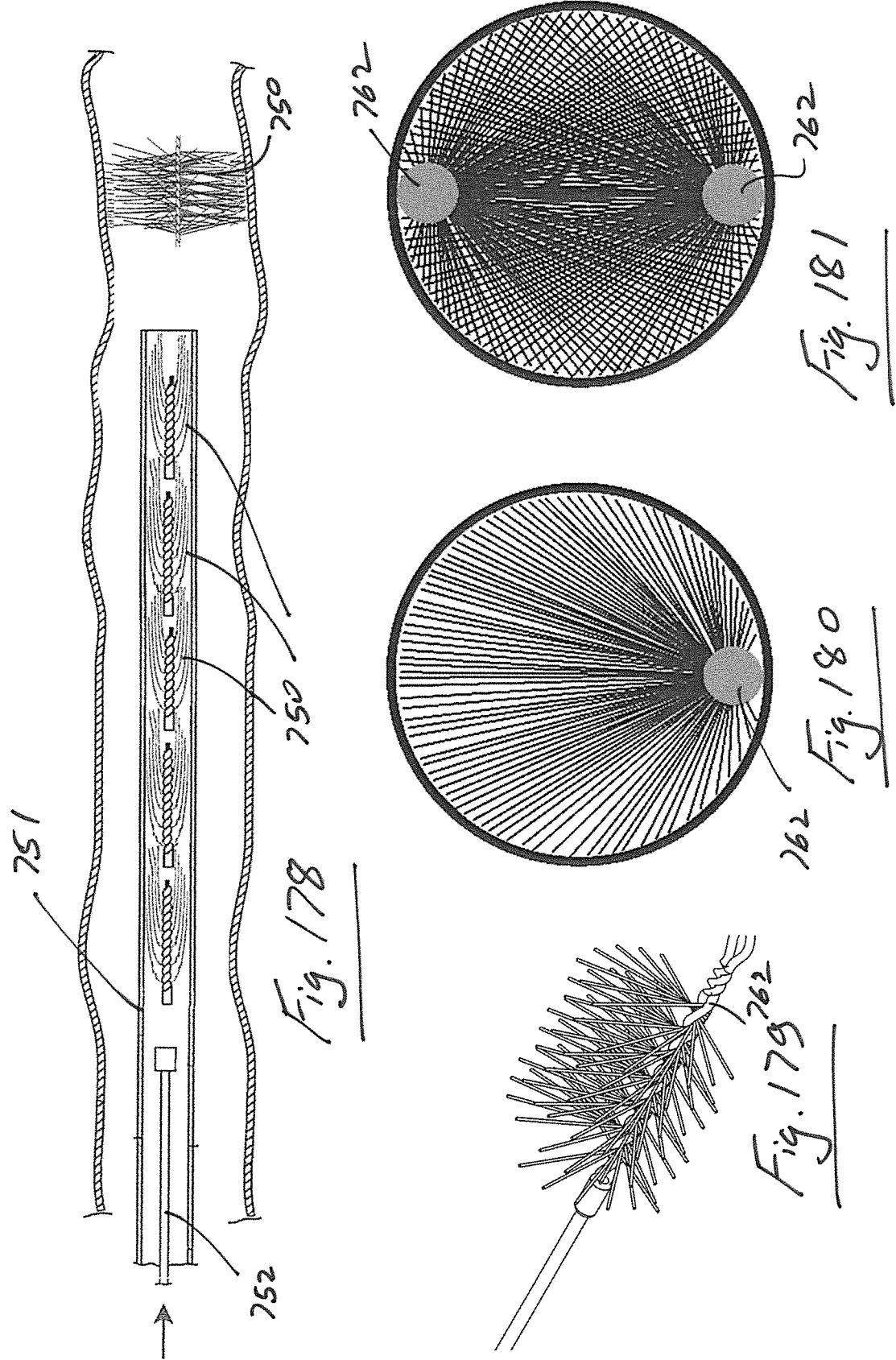

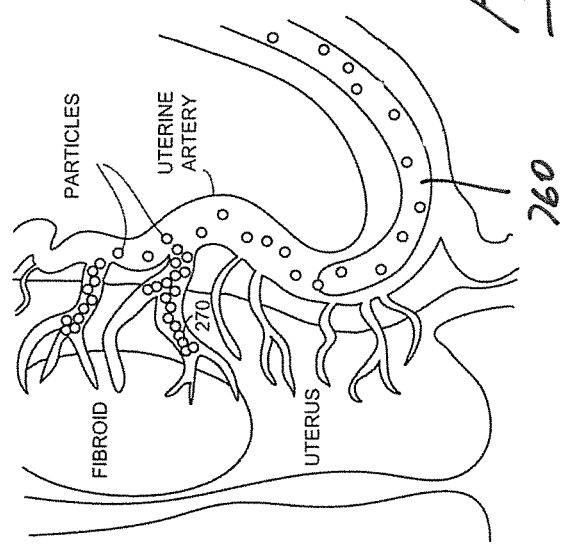
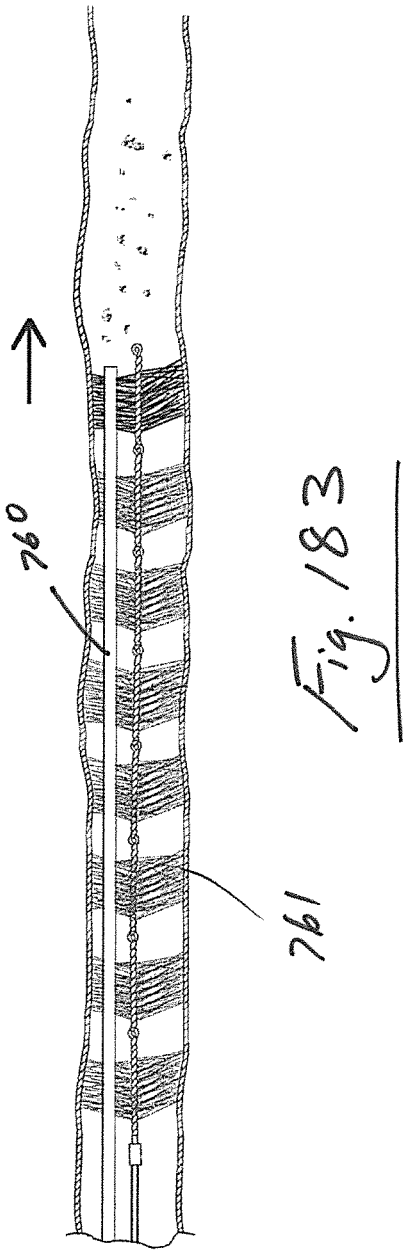
Fig. 182
Fig. 183

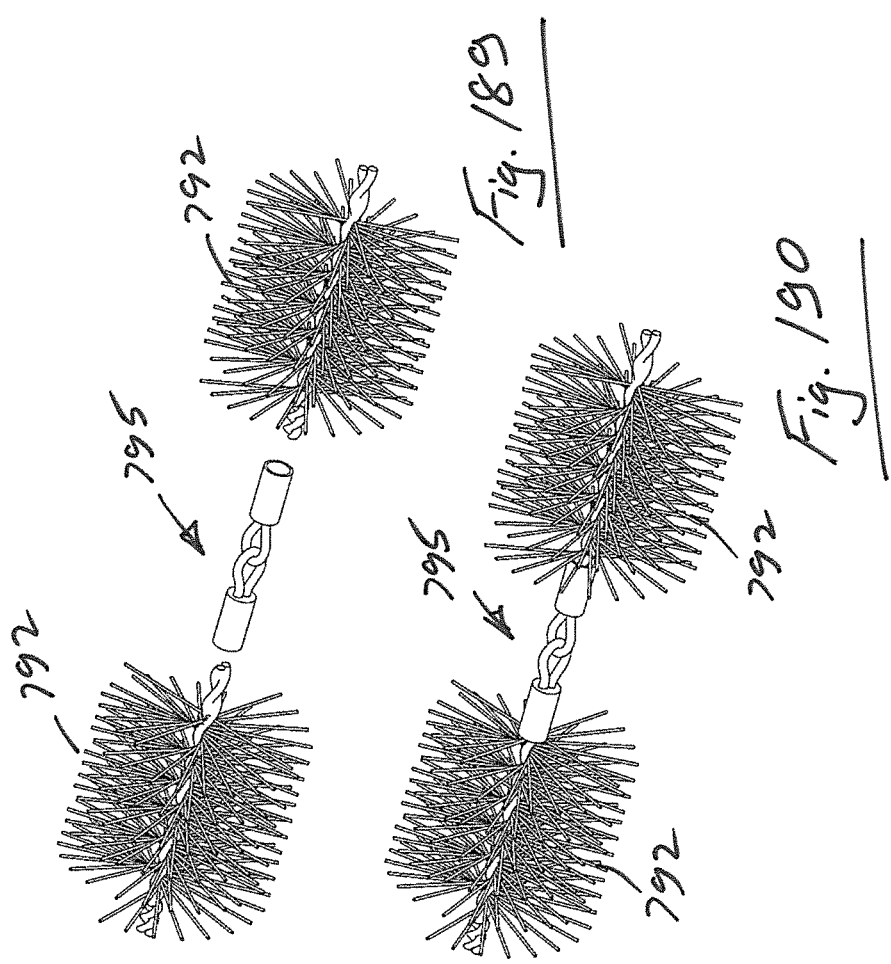

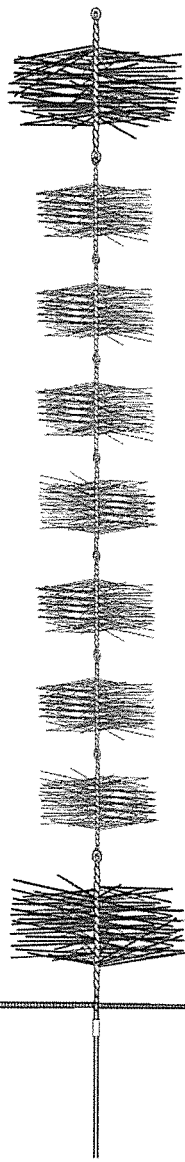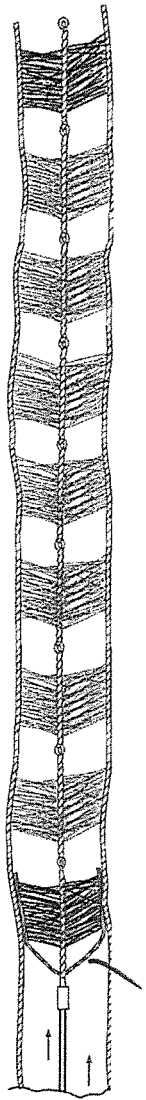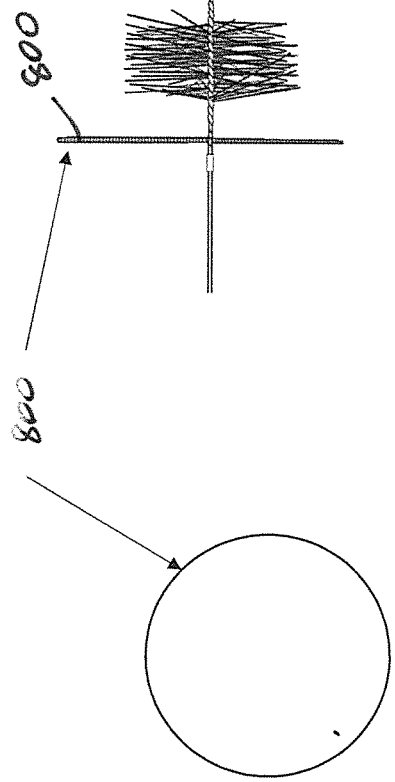
Fig. 191
Fig. 192
Fig. 193

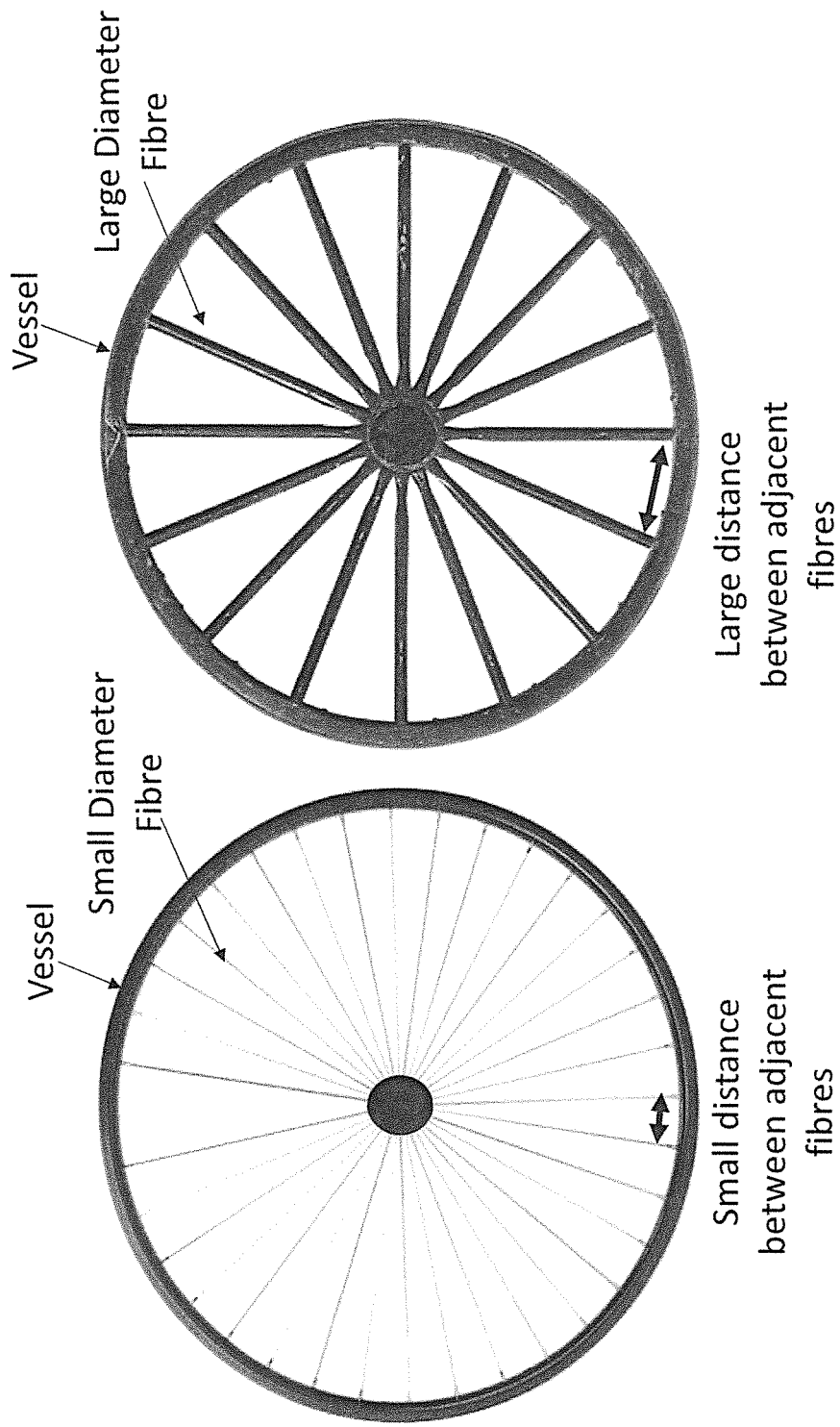

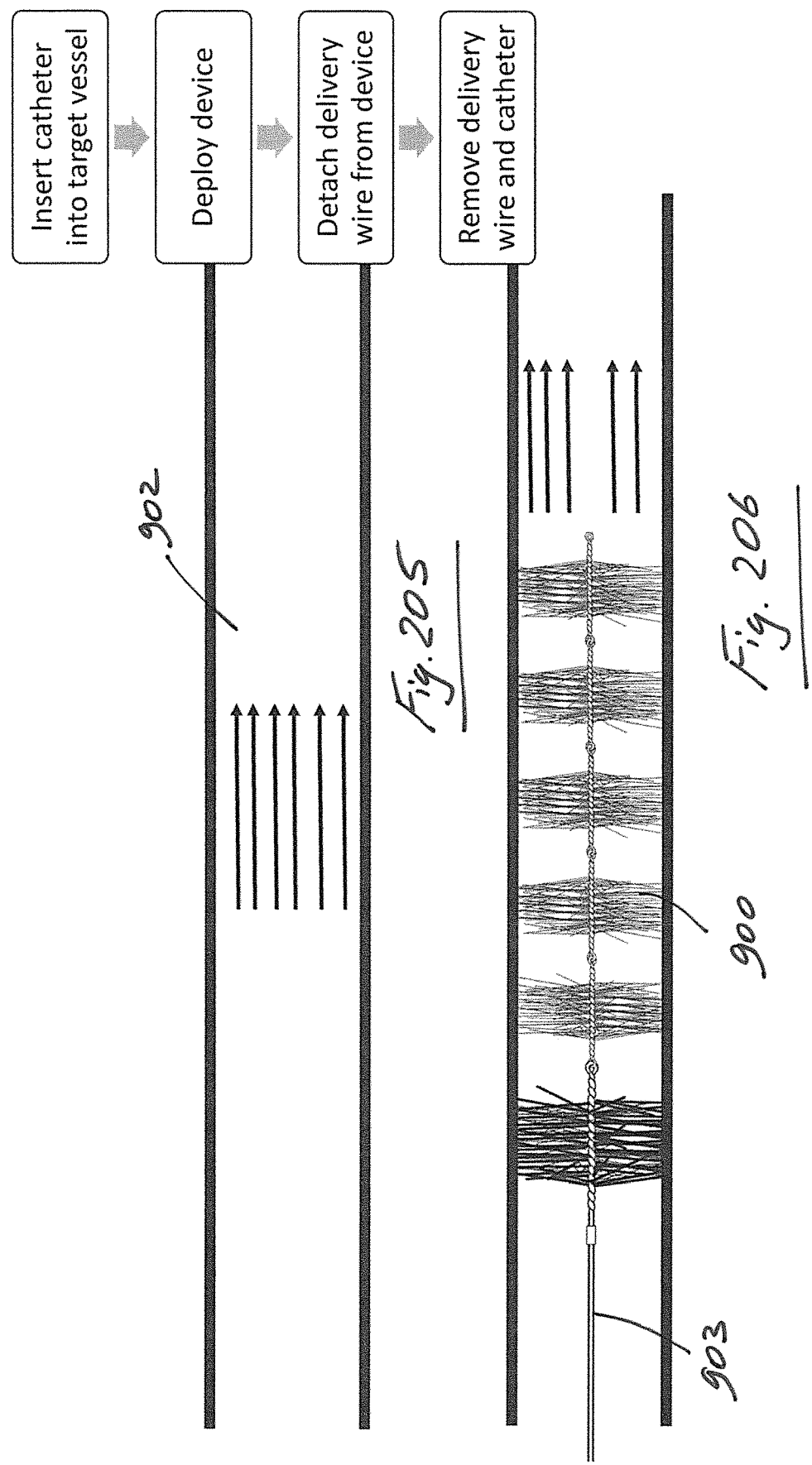

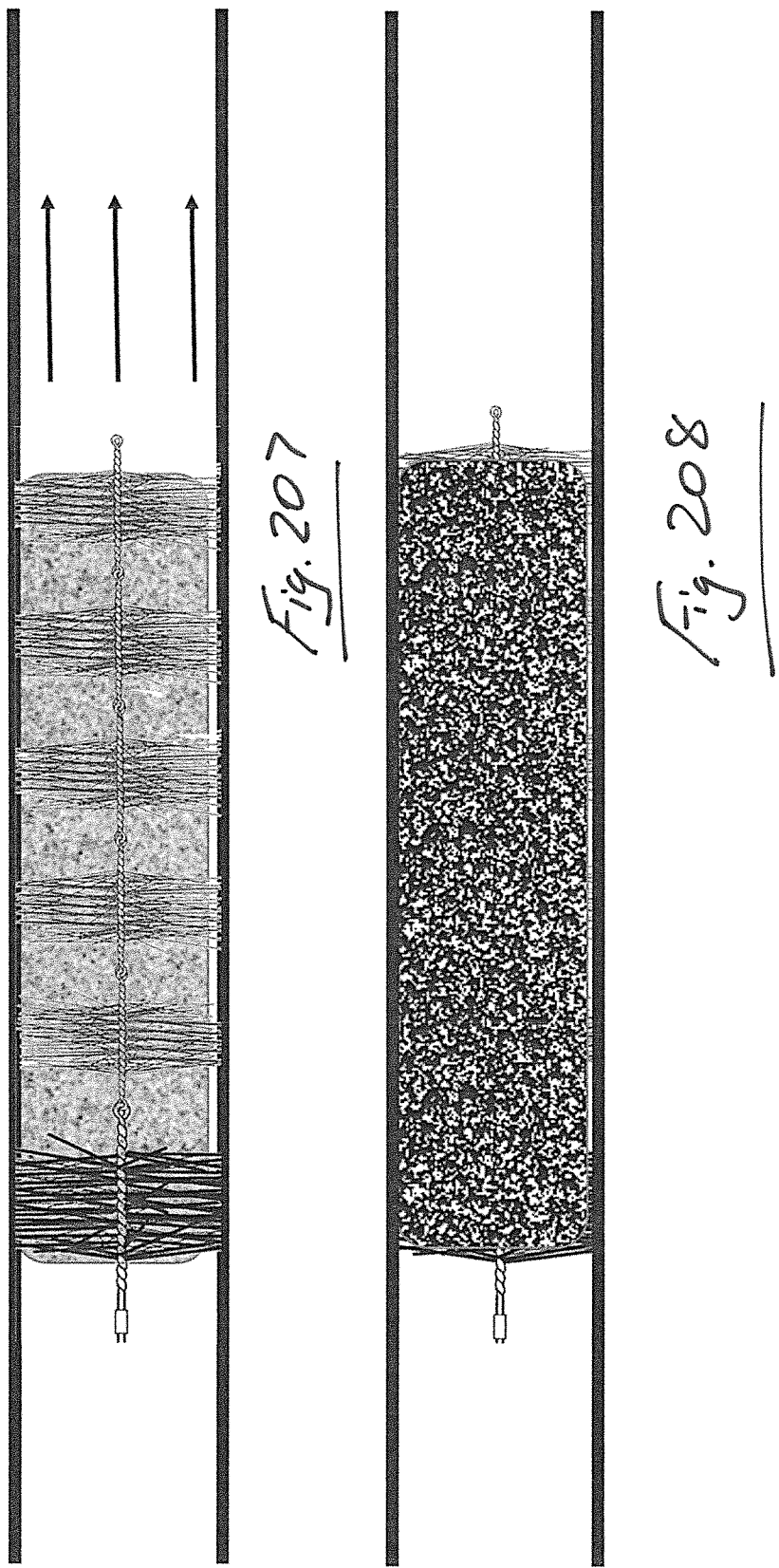

EMBOLISATION SYSTEMS

INTRODUCTION

This invention relates to devices and systems for embolisation.

Migration of conventional embolisation coils occurs 4-14% of transcatheter embolisations [2,3]. Non-target embolisation is an outcome of coils migration, the impact of which depends on the final location of the coils. In the venous system, the consequences can be catastrophic with literature indicating that coils can migrate into the renal vein, right atrium of the heart, lung (pulmonary artery). Percutaneous retrieval of the coils is technically very challenging and frequently cannot be attempted as the coils are often entrapped within the organs and tissue.

Coil migration occurs for various reasons:

Technical error: release of a coil or coil pack too distal or proximal to an adjoining larger vessel or plexus [6,7]

High blood flow areas can cause the coil to migrate.

Coil: vessel mismatch. The coils are undersized, hence will not injure the vessel wall, will not induce thrombosis, and are likely to migrate. Or the coils are oversized and will act like a guide-wire and pass further distally into the vessel [8,9].

Vessel dilation: coil migration can occur due to a disparity in the size of coils and dilated vessels, which can change in their diameters depending on vessel hemodynamics [5].

Coils impart a very low radial (anchor) force on the lumen, once a clot forms within the coil, blood flow can force it to migrate.

The profile of the embolisation device and delivery system is a critical success factor in successfully accessing target embolisation locations e.g. the iliac arteries are frequently tortuous in the presence of abdominal aortic aneurysms [8]. To combat this issue today, microcatheters are often employed in difficult or tortuous anatomy where use of standard catheters may induce spasm and lead to a failed embolisation procedure [8]. Additionally different stages in a procedure may require catheters with different mechanical properties e.g. accessing a visceral vessel, particularly in the presence of diseased or tortuous arteries, may require a catheter with a high degree of stiffness and torque control. In general, the lower the profile of the device and delivery system, the greater the accessibility of the device into tortuous and higher order vessels. A lower profile device reduces the diameter of catheter required for delivery and lowers the risks of access site infections, hematomas and lumen spasm.

Dependent on the clinical application of the device, variable anchor forces may be required to prevent migration of the prosthesis e.g. arterial and venous applications have variable blood flow rates and forces. This in turn, will lead to a compromise in terms of profile since larger fibres, which better anchor the bristle device in the lumen, will require a larger catheter for delivery.

The technique generally used to embolise vessels today is to insert a metallic scaffold (coil, plug) into the target vessel, to cause a thrombus that adheres to the scaffold, relying on the thrombus to induce blood cessation and eventually occlude the vessel. In general, available embolisation technology does not interfere with or interact with blood flow densely enough across the vessel cross section to induce rapid, permanent vessel occlusion.

Using technology available today, the physician will often have to prolong a specific duration of time for the technology to induce occlusion. In one approach the physician inserts coils and then waits 20 minutes for the coils to expand and cause vessel occlusion [1].

The restoration of the lumen of a blood vessel following thrombotic occlusion by restoration of the channel or by the formation of new channels, is termed recanalisation. Recanalisation can occur due to, coil migration, fragmentation of the embolisation material, and formation of a new vessel lumen that circumvents the occlusion [9]. Recanalization rates vary by procedure and embolic agent, ranging from 10% to portal vein embolisation to 15% for pulmonary arteriovenous malformations to 30% for splenic artery embolisation [12,14,15].

U.S. Pat. No. 5,573,547 describes a brush fixation method for attachment of tissues and occlusion of blood vessels.

STATEMENTS OF INVENTION

According to the invention there is provided an embolisation device for promoting clot formation in a lumen comprising a stem and a plurality of flexible bristles extending outwardly from the stem, the bristles having a contracted delivery configuration and a deployed configuration in which the bristles extend generally radially outwardly from the stem to anchor the device in a lumen, the device comprising a plurality of segments, each of which comprises a plurality of bristles and wherein the device comprises flexible sections between at least some of the bristle segments.

In one embodiment the stem comprises flexible sections between the bristle segments. The flexible sections may articulate.

In one case a bristle segment in the deployed configuration has a segment diameter, a segment length and a bristle density defined by the number of bristles in the segment. The segment bristle density may be from 100 to 1000 per centimetre of segment length. The segment bristle density may be from 100 to 300, optionally 200 to 800, optionally 300 to 800, optionally 200 to 1000 per centimetre of segment length. The segment diameter may be from 3 to 24 mm. The segment diameter may be from 3 to 6, optionally 6 to 8, optionally 8 to 10, optionally 10 to 12, optionally 12 to 16, optionally 10 to 18, optionally 10 to 24 mm. The segment diameter may be from 4 to 5, optionally 6, optionally 12, optionally 15, optionally 16 mm. The segment diameter may be from 4 to 6, optionally 8, optionally 15, optionally 17, optionally 22 mm. The segment length may be less than 8 mm, optionally from 3 to 7, optionally from 3 to 6, optionally from 3 to 4, optionally from 4 to 5 mm.

In some cases the diameter of the bristles is from 0.001 to 0.005 inches. The bristles may be from 0.001 to 0.002, optionally 0.002 to 0.003, optionally 0.002 to 0.004 inches. The stem may comprise a wire having a diameter of from 0.003 to 0.012 inches. The wire diameter may be 0.004, optionally 0.006 to 0.008, optionally 0.008 to 0.010, optionally 0.008 to 0.012 inches.

In one embodiment at least some of the segments are spaced-apart to define a gap therebetween.

The length of the gap between adjacent segments may be from 1 mm to 10 mm, optionally from 2 mm to 6 mm, optionally from 3 mm to 4 mm.

In one embodiment the embolisation device comprises a first group of bristles and a second group of bristles, the second group of bristles extending radially outwardly from the stem in the deployed configuration to a radial extent which is at least 1 mm, optionally at least 2 mm, optionally at least 3 mm, optionally at least 4 mm, optionally at least 5 mm more than the radial extent of the first group of bristles.

The second group of bristles may be provided at a proximal end of the device and/or at a distal end of the device.

In some embodiments at least some of the bristles are of a shape memory material such as Nitinol.

In one embodiment the device includes a flow restrictor having a contracted delivery configuration and an expanded deployed configuration. A flow restrictor may be located at a proximal end of the device and/or at a distal end of the device. The flow restrictor may comprise a membrane. At least some of the bristles urge the flow restrictor into the deployed configuration and/or the delivery configuration. In some cases the flow restrictor is at least partially self expandable on movement between the delivery configuration and the deployed configuration. The membrane may be impermeable. Alternatively the membrane comprises openings such as radially extending slots. In some cases the flow restrictor comprises a plurality of sections. The sections of the flow restrictor may be spaced-apart along a longitudinal axis of the device. In some cases the flow restrictor sections are of different diameters. The flow restrictor sections may be overlapped. At least a portion of the flow restrictor may be located between bristles on both sides of the restrictor. In some cases the flow restrictor in the deployed configuration extends from the stem to a radial extent which is less than that of the bristles. The flow restrictor may be of wind sock geometry and may have a distally facing opening. The flow restrictor may be of balloon geometry. In some cases sealing means is provided along the peripheral edge(s) of the flow restrictor.

In one embodiment at least some of the segments have loops and adjacent loops are interconnected to provide articulation between adjacent segments. In one case a suture or monofilament material which is less stiff than the stem is used to connect brush segments, providing improved flexibility and articulation. A spring connection may be provided between individual brush segments. The device may have means to limit the maximum length of the device. In some cases the device comprises a ring to connect bristle brushes with looped ends. In one embodiment the device comprises a wire or string connection, of a lower stiffness than the bristle brush stem, to accommodate bending of the device. In one case looped ends of the bristle brush stem are connected by a connector element. In one case a wire/string element is woven between a twisted wire stem of the bristle brush segment, the wire/string element being more flexible than the stem and emerging from the end of a bristle brush segment to connect to an adjacent bristle brush segment and wherein a gap between adjacent bristle brush segments enables the wire/string element to accommodate deformations. In one embodiment a thread type connection is provided between adjacent loops of bristle brush segments. The device may comprise an elastic tube mounted to two adjacent bristle brush segments to facilitate articulation between adjacent bristle brush segments. Adjacent bristle brush segments may be connected by a braid. In one case adjacent bristle brush segments are connected by a slotted tube, the slots being openable under a bending load to accommodate articulation between segments.

In one embodiment there are at least two different groups of bristles. In one case the bristles of one group have a thickness which is different than the thickness of bristles of another group. Alternatively or additionally one group of bristles is of a different material than the material of another group of bristles. Alternatively or additionally one group of bristles is more flexible than another group of bristles. Alternatively or additionally one group of bristles are interspersed with another group of bristles. Alternatively or additionally one group of bristles are adapted for anchoring the bristle device in a body lumen. An anchoring group of bristles may be provided at the proximal and/or distal end of the device. In some cases one group of bristles are adapted for occlusion of a lumen. The occlusion group of bristles may be located intermediate the proximal and distal ends of the bristle device. Some of the occluding group of bristles may be interspersed with the anchoring group of bristles so that the number of occluding bristles increases from the distal end towards the proximal end of the device. In one embodiment some of the anchoring groups of bristles are interspersed with the occluding group of bristles so that the number of anchoring bristles decreases from the distal end towards the proximal end of the device. In one case one group of bristles extend radially outwardly to one diameter and another group of bristles extend radially outwardly to another diameter which is different than the diameter of the first group of bristles. One group of bristles may be aligned differently than another group of bristles.

In one embodiment at least some of the bristles are adapted for delivery of a therapeutic agent. The agent delivery bristles are at least partially coated with a therapeutic agent. Alternatively or additionally at least some of the bristles contain a therapeutic agent. In one case the bristles comprise striations and/or holes for containing a therapeutic agent.

In one aspect the invention provides an embolisation bristle device for promoting clot formation in a body lumen comprising a stem and a plurality of flexible bristles extending generally radially outwardly from the stem, the bristles having a contracted delivery configuration and a deployed configuration in which the bristles extend generally radially outwardly of the stem to anchor the device in a lumen, the device comprising a plurality of segments, each of which comprises a plurality of bristles, and wherein at least some of the segments are spaced apart to define spaces therebetween to accommodate bending of the bristles. This aspect may have some or all of the features mentioned above and later in this specification.

The invention also provides a loading system for an embolisation bristle device comprising a stem and a plurality of bristles extending outwardly from the stem, the bristles having a contracted delivery configuration and a deployed configuration in which the bristles extend generally radially outwardly of the stem to anchor the device in a lumen, the bristles, on deployment being oriented towards one longitudinal direction. The loading system may be for deployment in a vein wherein, on deployment, the ends of the bristles are directed towards the heart to prevent migration. Alternatively the loading system may be for deployment in an artery wherein, on deployment, the ends of the bristles are directed away from the heart to prevent migration. The loading system may comprise a loading tube having a distal end which can be connected to a guide catheter. The loading system may comprise a loading wire which is releasable attachable to the distal end of the bristle device. The loading system may comprise a delivery wire which can attach to the proximal end of the bristle device for pushing the bristle device through the loading tube and into a guide catheter for delivery to a target vessel site. A distal end of the bristle device may be connectable to the loading wire. A proximal end of the bristle device may be connectable to the delivery wire. In one case the distal end of the bristle device and the end of the loading wire has a loop and hook configuration for interconnection. In one case the proximal end of the bristle device has a threaded end. In some cases both the proximal and distal ends of the bristle device are threaded.

Also provided is an embolisation bristle device loading system comprising a bristle device for delivery into a body lumen; a loading tube; and a loading element for loading the bristle device into the loading tube. In one case the loading element is detachably mountable to the bristle device. The loading element may comprise a loading wire. The embolisation bristle device loading system may comprise a delivery catheter for receiving the bristle device from the loading tube. The loading element may be adapted for loading the bristle device from the loading tube into the delivery catheter. The loading element may be adapted for deploying the bristle device from the delivery catheter. The embolisation bristle device loading system may comprise a taper or a funnel to aid loading of the bristle device into the loading tube and/or the delivery catheter. The taper or funnel may comprise an extension of the loading tube.

In one embodiment the loading tube comprises means for re-orientating at least some of the bristles of the bristle device as the bristle device is passing through the loading tube. In one case the re-orientation means comprises at least one hole in the wall of the loading tube through which the bristles may temporarily extend radially outwardly for transition from a first configuration in which the bristles are aligned at a first angle to the longitudinal axis of the loading tube and a second configuration in which the bristles are aligned at a second angle to the longitudinal axis of the loading tube. In the second configuration the bristles may extend generally in an opposite direction to the orientation of the bristles in the first configuration. In one case the re-orientation means comprises at least one slot in the wall of the loading tube.

Also provided is a method for loading an embolisation bristle device into a delivery catheter comprising the steps of providing a bristle device, a loading tube and a loading element; using the loading element, delivering the bristle device into the loading tube; and using the loading element, delivering the bristle device into a delivery catheter.

The method may comprise deploying the bristle device from the delivery catheter using the loading element. The loading element is releasably mountable to the bristle device and the method comprises mounting the loading element to the bristle device for loading the bristle device into the loading tube and/or for loading the bristle device into the delivery catheter and/or for deploying the bristle device from the delivery catheter, and/or for retrieving a deployed bristle device. In one case after delivery of the bristle device into the loading tube and/or into the delivery catheter and/or after deployment of the bristle device, the loading element is detached from the loading element. The loading element may be re-attached to the bristle device for retrieval of the bristle device.

In a further aspect the invention provides an embolisation device for promoting clot formation in a lumen comprising a stem and a bundle of flexible bristles extending outwardly from the stem, the bristles having a contracted delivery configuration and a deployed configuration in which the bristles extend generally radially outwardly from the stem to anchor the device in a lumen, the bundle of bristles in the deployed configuration having a diameter, a length and a bristle density defined by the number of bristles in the bundle and wherein the bristle density is from 100 to 1000 per centimetre of segment length, the bundle diameter is from 3 to 24 mm, and wherein the longitudinal length of the bundle is less than 8 mm. The device may comprise a flow restrictor at a proximal end of the device and/or at a distal end of the device. In one case the flow restrictor comprises a membrane which has a contracted delivery configuration and an expanded deployed configuration. This aspect may have some or all of the features mentioned above and later in the specification.

According to the invention there is provided a bristle device for delivery into a body lumen comprising a longitudinally extending stem and a plurality of bristles extending generally radially outwardly from the stem wherein there are at least two different groups or types of bristles.

In one embodiment bristles of one group have a thickness which is different than the thickness of bristles of another group.

In one case one group of bristles is of a different material than the material of another group of bristles.

One group of bristles may be more flexible than another group of bristles.

In one embodiment one group of bristles are interspersed with another group of bristles.

In one case one group of bristles are adapted for anchoring the bristle device in a body lumen. An anchoring group of bristles may be provided at the proximal and/or distal end of the device.

In one embodiment one group of bristles are adapted for occlusion of a lumen. The occlusion group of bristles may be located intermediate the proximal and distal ends of the bristle device.

In one case at least some of the occluding group of bristles are interspersed with the anchoring group of bristles so that the number of occluding bristles increases from the distal end towards the proximal end of the device.

In one embodiment some of the anchoring groups of bristles are interspersed with the occluding group of bristles so that the number of anchoring bristles decreases from the distal end towards the proximal end of the device.

In one case one group of bristles extend radially outwardly to one diameter and another group of bristles extend radially outwardly to another diameter which is different than the diameter of the first group of bristles.

According to a further aspect of the invention one group of bristles are aligned differently than another group of bristles.

At least some of the bristles may be adapted for delivery of a therapeutic agent. The agent delivery bristles may be at least partially coated with a therapeutic agent. Alternatively or additionally at least some of the bristles contain a therapeutic agent. In one case the bristles comprise striations and/or holes for containing a therapeutic agent.

In another aspect the invention provides a bristle device loading system comprising:—
  a bristle device for delivery into a body lumen;
  a loading tube; and
  a loading element for loading the bristle device into the loading tube.

In one embodiment the loading element is detachably mountable to the bristle device.

In one case the loading element comprises a loading wire.

The system may comprise a delivery catheter for receiving the bristle device from the loading tube. The loading element may be adapted for loading the bristle device from the loading tube into the delivery catheter. The loading element may also be adapted for deploying the bristle device from the delivery catheter.

In one embodiment the system comprises a taper or a funnel to aid loading of the bristle device into the loading tube and/or the delivery catheter.

In one case the taper or funnel comprises an extension of the loading tube.

In one embodiment the loading tube comprises means for re-orientating at least some of the bristles of the bristle device as the bristle device is passing through the loading tube.

The re-orientation means may comprise at least one hole in the wall of the loading tube through which the bristles may temporarily extend radially outwardly for transition from a first configuration in which the bristles are aligned at a first angle to the longitudinal axis of the loading tube and a second configuration in which the bristles are aligned at a second angle to the longitudinal axis of the loading tube. In one case, in the second configuration the bristles extend generally in an opposite direction to the orientation of the bristles in the first configuration.

The re-orientation means may comprise at least one slot in the wall of the loading tube.

In a further aspect the invention provides a method for loading a bristle device into a delivery catheter comprising the steps of:—
  providing a bristle device, a loading tube and a loading element;
  using the loading element, delivering the bristle device into the loading tube; and
  using the loading element, delivering the bristle device into a delivery catheter.

The method may comprise deploying the bristle device from the delivery catheter using the loading element.

In one case the loading element is releaseably mountable to the bristle device and the method comprises mounting the loading element to the bristle device for loading the bristle device into the loading tube and/or for loading the bristle device into the delivery catheter and/or for deploying the bristle device from the delivery catheter, and/or for retrieving a deployed bristle device.

In one case after delivery of the bristle device into the loading tube and/or into the delivery catheter and/or after deployment of the bristle device, the loading element is detached from the loading element.

In one embodiment the loading element is re-attached to the bristle device for retrieval of the bristle device.

The invention also provides a bristle device which confirms to a vessel lumen. The bristle device in this embodiment has a larger diameter than the target vessel but the bristles do not deliver sufficient force to perforate the vessel.

The invention further provides a bristle device which, when implanted imposes a greater resistance to flow in the axial direction compared to the radial (lateral) direction.

In another aspect the invention provides the use of a bristle device to cause vascular occlusion for the treatment of haemorrhoids.

The invention also provides a bristle device for delivery into a body lumen comprising a stem and a plurality of flexible bristles extending generally radially outwardly from the stem wherein the device comprises a plurality of segments, each of which comprises a plurality of bristles extending generally radially outwardly from the stem, and wherein at least some of the segments are spaced apart to define spaces therebetween to accommodate bending of the bristles.

This bending of the bristles enables the device to be deformed into a collapsed condition, so that the diameter in the collapsed condition is smaller than would be the case if such spaces were not present between the segments.

The invention further provides a bristle device for delivery into a body lumen comprising a stem and a plurality of flexible bristles extending generally radially outwardly from the stem wherein the device comprises a plurality of bristle segments, each of which comprises a plurality of bristles extending generally radially outwardly from the stem, and wherein the device comprises flexible sections between at least some of the bristle segments.

In one case the stem comprises flexible sections between the bristle segments.

In some embodiments the flexible sections articulate. The flexible sections may articulate to enable the device to pass through a catheter place in a tortuous anatomy, to enable the device to be deployed in a curved vessel and/or to enable the device to be deployed across a bifurcation.

The flexible sections also enable the device to accommodate bending during physiological loading and thereby preventing fracturing.

In one case at least some of the segments have loops and adjacent loops are interconnected to provide articulation between adjacent segments.

The stem may be constructed from wires twisted together and a region of increased flexibility is provided by discontinuing one of the wires, thus decreasing the stiffness between adjacent bristle segments.

In one embodiment a suture or monofilament material which is less stiff than the stem is used to connect brush segments, providing improved flexibility and articulation. The suture may be connected to the bristle segments using a hypotube. The hypotube may be attached to the stem and suture by crimping.

In another embodiment a spring connection is provided between individual brush segments. This spring may be configured such that in the unloaded configuration it cannot compress In another case the spring is configured to compress or elongate to facilitate adjustment of the device length during deployment.

In one embodiment the device has a limiter to limit the maximum length of the device.

In one case the maximum extension of a spring-like connection is limited by the inclusion of a tension wire, which is connected to each segment of the bristle brush.

In another embodiment the spring may be configured such that the total device length may be reduced but not increased.

In one case the device comprises a ring to connect bristle brushes with looped ends. The ring may be of relatively stiff to provide a hinge type joint. The ring may be relatively flexible such that the ring flexes during bending of the device.

In one embodiment a wire or string connection, of a lower stiffness than the bristle brush stem, is used to accommodate bending of the device.

In one case looped ends of the bristle brush stem are connected by a connector element.

In one embodiment a wire/string element is woven between a twisted wire stem of the bristle brush segment, the wire/string element being more flexible than the stem and emerging from the end of a bristle brush segment to connect to an adjacent bristle brush segment and wherein a gap between adjacent bristle brush segments enables the wire/string element to accommodate deformations.

In one case a thread type connection is provided between adjacent loops of bristle brush segments.

In one embodiment an elastic tube is mounted to two adjacent bristle brush segments to facilitate articulation between adjacent bristle brush segments.

In one case the elastic tube has an inner diameter which is smaller than the outer diameter of the bristle brush stem.

In another case the elastic tube is of a heat shrinkable material, which when subject to heat reduces its diameter to adhere to the stem of adjacent brush segments.

Adjacent bristle brush segments may be connected by a braid.

Adjacent bristle brush segments may be connected by a slotted tube, the slots being openable under a bending load to accommodate articulation between segments.

In a one embodiment at least some of the segments are spaced apart to define spaces therebetween to accommodate bending of the bristles.

In another aspect the invention provides a loading system for a bristle device comprising a stem and a plurality of bristles extending generally radially outwardly from the stem, the bristles, on deployment being oriented at least in part in one longitudinal direction.

For deployment in a vein, on deployment, the ends of the bristles are directed towards the heart to prevent migration.

For deployment in an artery, on deployment, the ends of the bristles are directed away from the heart to prevent migration.

In one embodiment the loading system comprises a loading tube having a distal end which can be connected to a guide catheter.

The loading system may comprise a loading wire which is releasable attachable to the distal end of the bristle device.

The loading system may comprise a delivery wire which can attach to the proximal end of the bristle device for pushing the bristle device through the loading tube and into a guide catheter for delivery to a target vessel site.

In one case a distal end of the bristle device is connectable to the loading wire.

Alternatively or additionally a proximal end of the bristle device is connectable to the delivery wire.

In one case the distal end of the bristle device and the end of the loading wire has a loop and hook configuration for interconnection.

In one embodiment the proximal end of the bristle device may have a threaded end.

In another embodiment both the proximal and distal ends of the bristle device are threaded.

BRIEF DESCRIPTION OF THE DRAWINGS

The invention will be more clearly understood from the following description of an embodiment thereof, given by way of example only, with reference to the accompanying drawings, in which:

FIG. 1 is an illustration of a bristle device according to the invention with two types of bristles having different diameters;

FIG. 2 illustrates the device of FIG. 1 loaded into a tube;

FIGS. 3 and 4 illustrate bristles of different diameters;

FIGS. 5 to 8 illustrate bristle devices with bristles of different diameters;

FIG. 9 illustrates a bristle device with two types of bristles (dashed, continuous, interspersed and evenly distributed);

FIG. 10 illustrates the uniform anchoring force applied by the device of FIG. 9;

FIG. 11 illustrates a bristle device in which two different types of bristles are used;

FIG. 12 illustrates the variation in the anchoring force applied by the device of FIG. 11;

FIGS. 17a to 17c illustrate the effect of time in the collapsed condition on unconstrained geometry of a bristle device, when deployed;

FIG. 34 shows a bristle device with bristles pointing in opposed directions;

FIG. 35 illustrates vessel perforation by portion of a bristle device;

FIGS. 37 to 39 illustrate alternative bristle devices with geometries to conform with particular vessel shapes;

FIG. 40 illustrates deformation of a vessel by a bristle device;

FIGS. 86 and 87 illustrate a bristle device with length modifying components;

FIG. 88 illustrates deployment of the device of FIGS. 86, 87;

FIG. 97 illustrates a bristle device deployed to treat a cerebral aneurysm;

FIGS. 98 to 100 illustrate bristle devices with gaps to limit clot fragments;

FIG. 113 illustrates the manufacture of a twisted wire bristle device;

FIG. 114 shows a twisted wire device with varying core wire pitch;

FIGS. 118 to 125 illustrate bristle devices with various drug delivery features;

FIGS. 125 and 126 illustrate the use of a bristle device of the invention to treat haemorrhoids;

FIG. 131 are perspective views of another embolisation device in a straight configuration (a) and a bent configuration (b);

FIGS. 132(a) to 142(b) are perspective views of further embolisation devices of the invention in configurations similar to FIGS. 131(a) and 131(b);

FIG. 143 is a diagram illustrating the optimal orientation of bristles to prevent migration in venous vessels;

FIG. 144 is a diagram illustrating the optimal orientation of bristles to prevent migration in arteries;

FIGS. 149 to 153 illustrate loading, delivery and deployment in an artery;

FIGS. 154 to 158 illustrate loading, delivery and deployment in a vein;

FIGS. 159 to 166 illustrate various configurations of anchoring segments and occluding segments;

FIG. 169 illustrates fibres which are shape set;

FIGS. 170 to 177 illustrate various embolisation devices in different locations of use;

FIG. 178 illustrates delivery of a number of segments from a catheter;

FIGS. 179 to 181 illustrate offsetting of the stem core;

FIGS. 182 and 183 illustrate the use of the device to prevent backflow of particles delivered during particle embolisation;

FIGS. 187 to 190 illustrate one method of joining segments together;

FIGS. 191 to 200 illustrate various embolisation devices incorporating a flow restrictor;

FIGS. 202 and 203 illustrate the effect of using small diameter and large diameter fibres;

FIGS. 205 to 208 are diagrams illustrating steps in an embolisation procedure using a device of the invention.

DETAILED DESCRIPTION

Figures 13, 14:
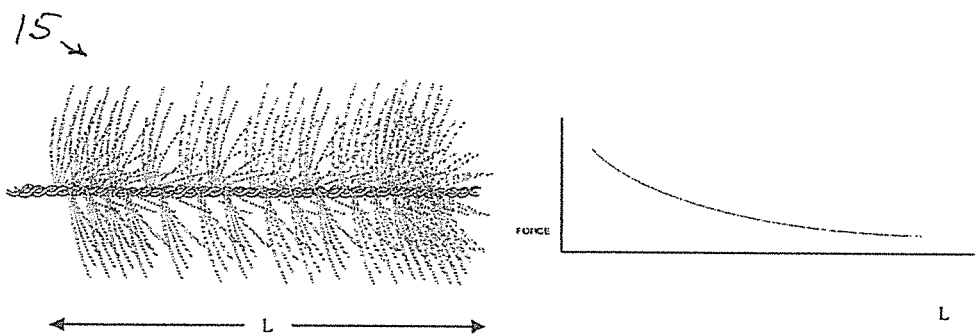
FIG. 13 illustrates another bristle device with a gradual variation in bristle density.
FIG. 14 is a diagram illustrating the variation in the force applied by the device of FIG. 13.

Referring to the drawings and initially to FIGS. 1 to 8 thereof there is illustrated a bristle device for delivery into a body lumen. The bristle device comprises a longitudinally extending stem 1 and a plurality of bristles extending generally radially outwardly from the stem. In the invention there are at least two different groups or types of bristles.

In one case a prosthesis with two or more bristle fibre diameters is provided to ensure a low profile for the device when loaded in the catheter 5, and with sufficient anchor force to prevent migration. Smaller diameter fibre bristles 2 are intended primarily to promote and enhance thrombogenicity, while larger diameter fibre bristles 3 are intended primarily to anchor the device in the lumen to prevent migration.

Lumen occlusion occurs due to thrombogenicity of the device, which is a function of its surface area and its ability to cause stasis. For a given volume of fibre material, many small fibres 2 can be more efficiently fitted into a catheter than few larger fibres 3.

Similarly, small fibres 2 are more thrombogenic per unit volume than larger fibres 3; as for a given volume of fibre material, there will be a greater amount of surface area for multiple small diameter fibres, than a few large diameter fibres.

FIGS. 5 and 6 illustrate a bristle device 6 with low diameter fibres 2. This enables the device to be collapsed to a low diameter, $ø_1$. FIGS. 7 and 8 illustrate a prosthesis 7 with larger diameter fibres 3, which will enhance the migration prevention properties of the prosthesis. The collapsed diameter, $ø_2$, of this prosthesis is larger than $ø_1$.

The bristle device of FIGS. 1 and 2 has a combination of both low and high diameter fibres 2, 3. This enables a compromise in profile to a diameter, $ø_3$, where $ø_1<ø_3<ø_2$. This approach provides good migration prevention properties (from large diameter fibres 3) combined with good thrombogenicity and low profile (from the smaller diameter fibres 2).

The different bristle types can be of the same or different materials. More than one bristle material could also be used instead of, or in combination with more than one bristle diameter.

FIG. 9 illustrates another bristle device 8 according to the invention which in this case has two different types of bristle interspersed and generally equally distributed along the length of the device. The different types of bristles may be distinguished by their dimensions or material, each contributing separately in terms of anchor force and occlusion. Because of the equal distribution, the anchor force is uniformly distributed along the bristle device length as illustrated in FIG. 10.

Various alternative arrangements of different types or groups of bristles may be provided.

For example, FIGS. 11 and 12 illustrate a bristle device 9, of length L, in which two different types of bristle are used: one for the middle section 10 and one for the ends 11, 12. In this case, the bristles at the ends of the device have a higher diameter. These bristles are intended to anchor the prosthesis within the lumen. The middle section contains a higher density of bristles with a lower diameter, and is intended to cause more interference with blood flow along with more surface contact with the blood and consequently, occlusion of the lumen.

FIG. 13 illustrates a bristle device 15, which has two different types of bristle. In this case the bristles with better properties for anchoring the device in the lumen are more densely located on the left hand side of the bristle device and taper off towards the right hand side of the device where the density of the bristles of the second type of bristles is higher. This would be advantageous in a high flow scenario requiring extremely large number of small diameter bristles to cause occlusion. By having the anchoring bristles at the end only, the other end could contain the extremely high number of lower diameter bristles required to cause occlusion, without compromising profile. Because of the distribution, the anchor force is distributed along the bristle device length as illustrated in FIG. 14.

Figure 16:
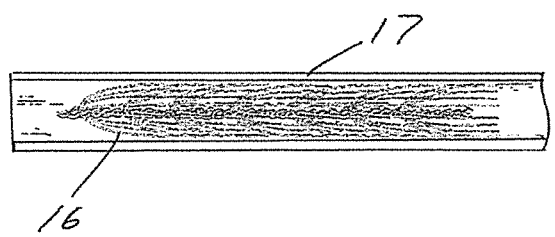
FIGS. 15 and 16 are illustrations of another bristle device of the invention in collapsed and unconstrained configurations.
Figure 15:
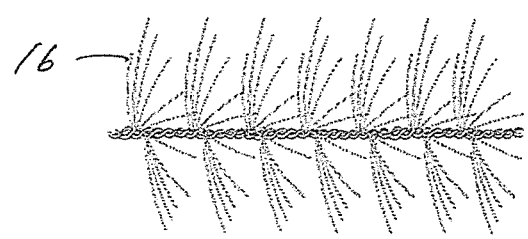

A bristle device 16 when manufactured has an unconstrained geometry as illustrated in FIG. 15, which is the desired shape. In order to be delivered through a catheter the bristle device must spend some time in a collapsed condition in a catheter 17 as illustrated in FIG. 16.

Storage of a device in a collapsed condition can lead to shape-setting of a bristle device, particularly if the bristles are constructed from a polymer. Specifically, once the bristle device is deployed from the catheter it may not return fully to its original shape. Shape-setting refers to any change in shape, which is caused due to storage a catheter for a prolonged period. In general, the longer the period of storage the greater the degree of shape setting is likely to be. This is shown schematically in FIGS. 17 a to 17 c.

To counteract this problem, in the invention a loading system is provided. The loading system comprises a loading tube 20. The purpose of the loading tube 20 is to allow the clinician to collapse a bristle device 25 for delivery through a delivery catheter 26 immediately before for (temporary or permanent) implantation in a lumen. In this way the bristle device 25 will not spend a substantial amount of time in the collapsed condition, minimising the potential for shape setting. The loading system also comprises a loading element such as a wire 21 for loading the bristle device 25 into the loading tube 20.

Figure 18:
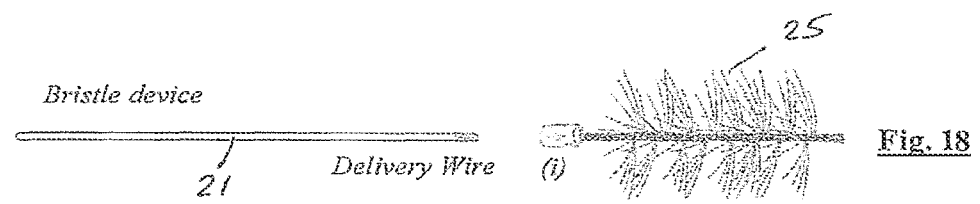
FIGS. 18 to 24 illustrate a bristle device loading system according to the invention in various configurations of use.
Figure 19:
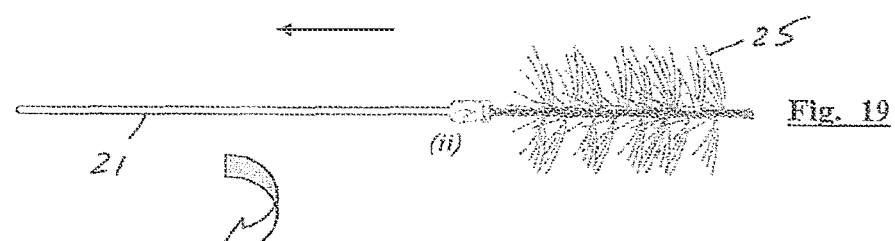
Figure 20:
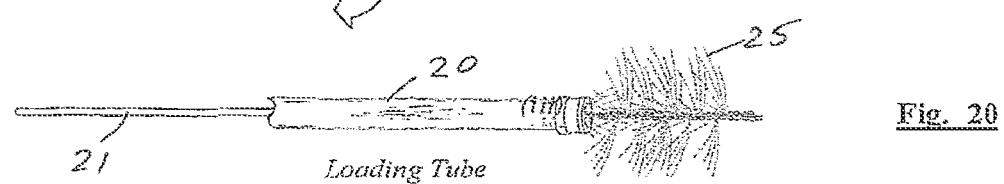
Figure 21:
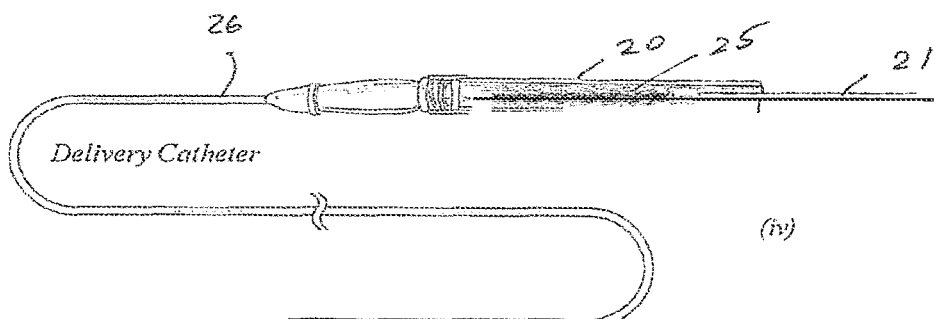
Figure 22:
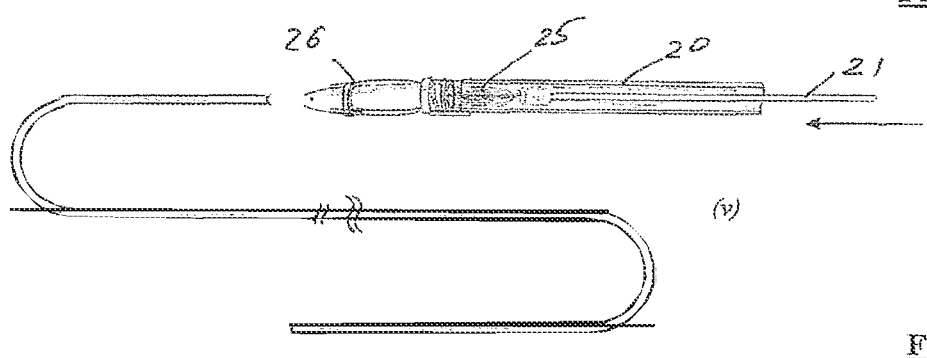
Figure 23:
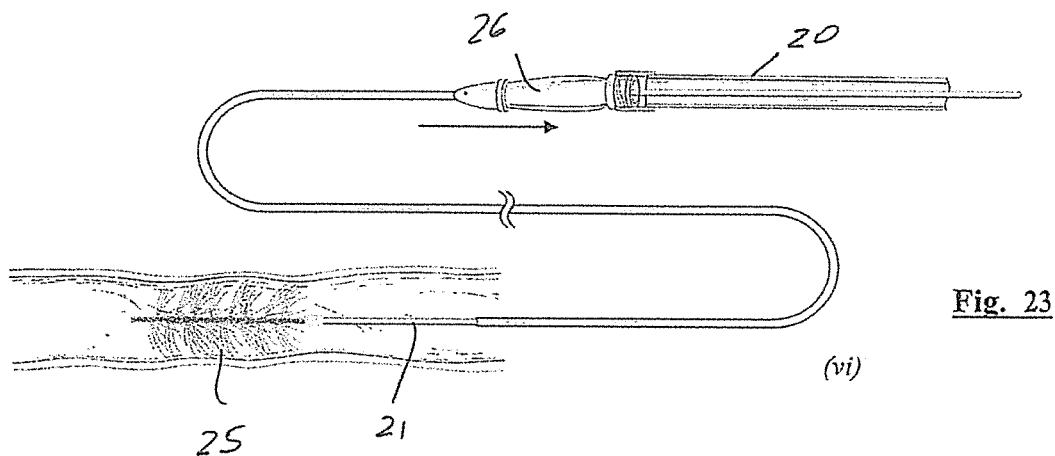
Figure 24:
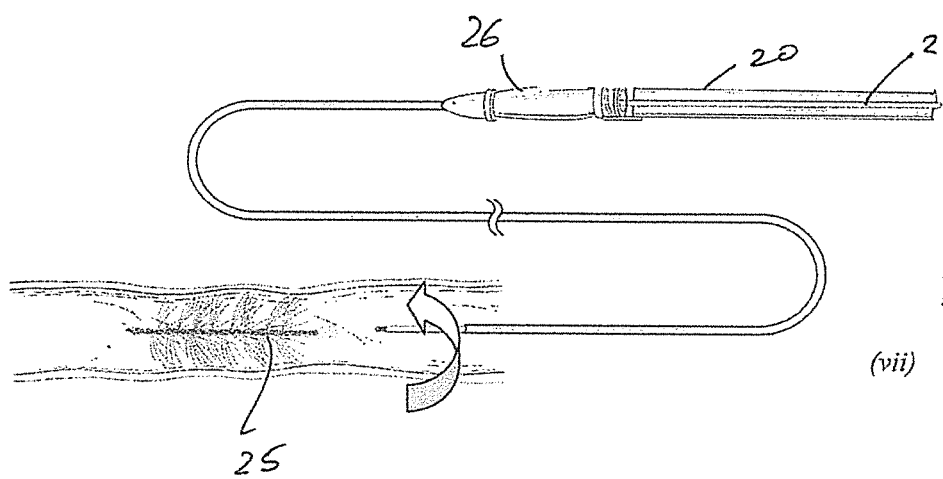

The bristle device can be delivered through any suitable delivery catheter 26. The steps for use of the loading system are as follows:
 i. Bring bristle device 25 and delivery wire 21 in contact (FIG. 18)
 ii. Screw the delivery wire 21 into the prosthesis 25 (FIG. 19)
 iii. Using the delivery wire 21, pull the bristle device 25 into the loading tube 20 (FIG. 20)
 iv. Connect the loading tube 20 to a delivery catheter 26 (FIG. 21)
 v. Push the bristle device 25 into the delivery catheter 26 using the delivery wire 21 (FIG. 22)
 vi. Once the tip of the bristle device 25 is at the tip of the catheter 26 (located at the distal point of the vessel intended for implantation), holding the delivery wire 21 still, retract the delivery catheter 26 to deploy the bristle device 25 (FIG. 23)
 vii. Once satisfied with the position of the device 25, unscrew the delivery wire 21 from the bristle device 25 to detach (FIG. 24)

Figure 25:
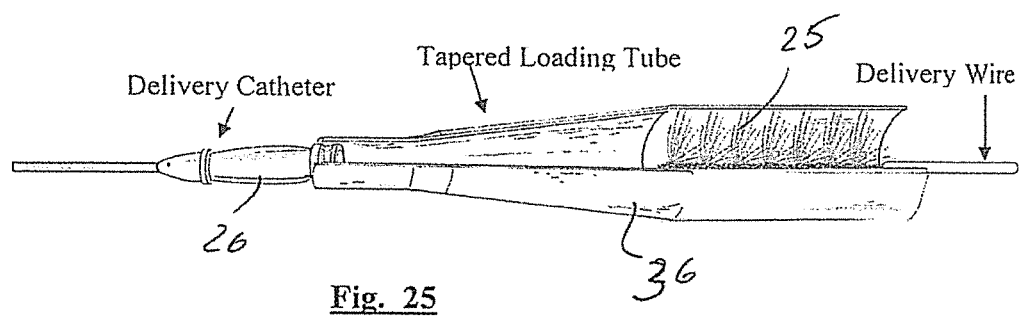
FIGS. 25 and 26 illustrate a tapered loading tube.
Figure 26:
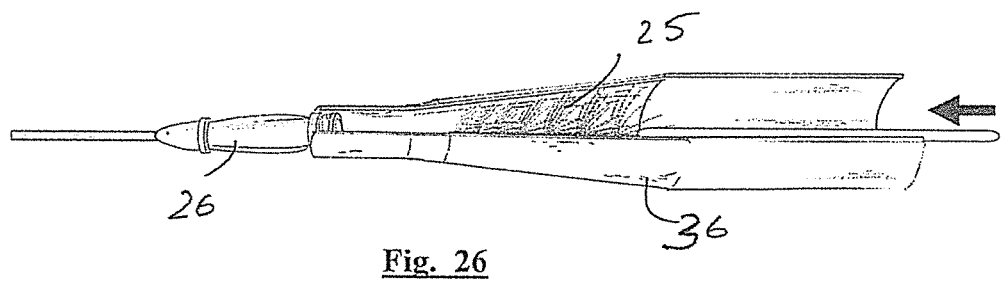

Referring to FIGS. 25 and 26, in another embodiment, a loading tube 36 of tapered geometry will allow the user to crimp down the bristle device 25 to the collapsed state as it is pushed via the delivery wire into the catheter for delivery to a vessel.

Figure 27:
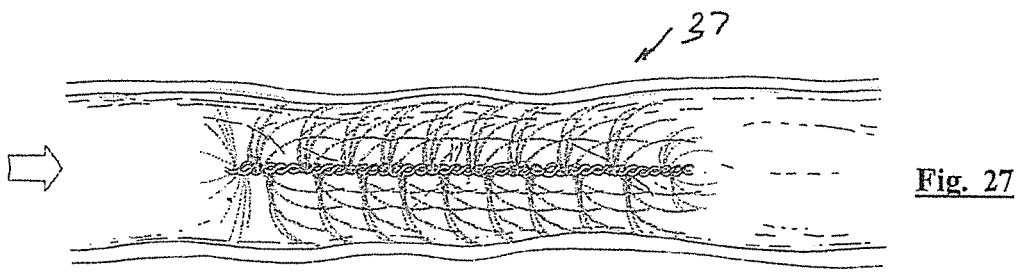
FIGS. 27 and 28 illustrate differing bristle orientations with respect to flow.
Figure 28:
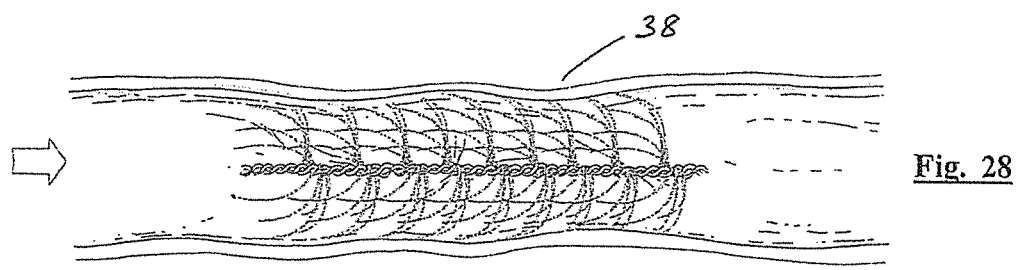
Figure 29:
FIGS. 29 and 30 show a loading tube with a re-orientation feature according to the invention.
Figure 30:
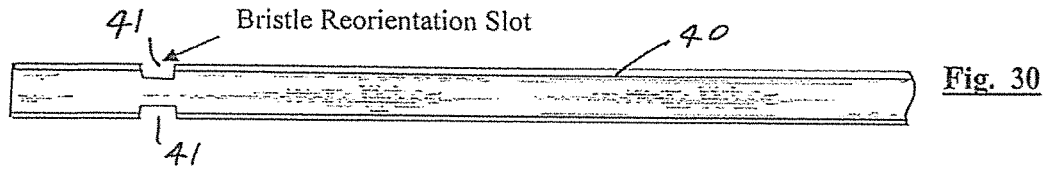
Figure 31:
FIGS. 31 to 33 illustrate the loading tube of FIGS. 29, 30, in use.
Figure 32:
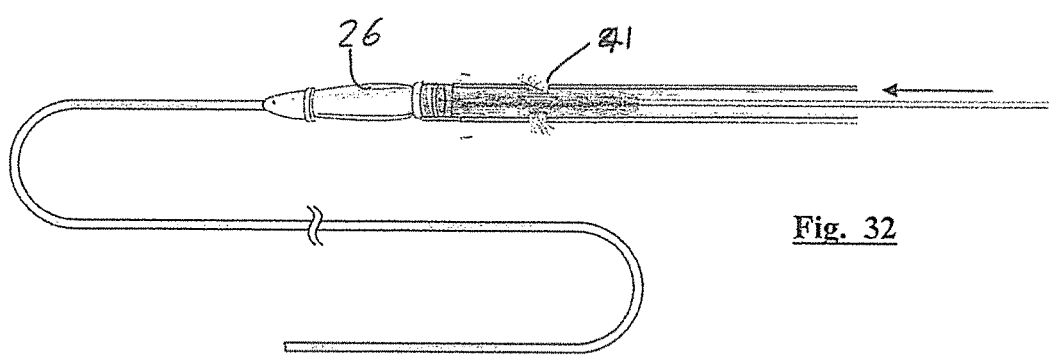
Figure 33:
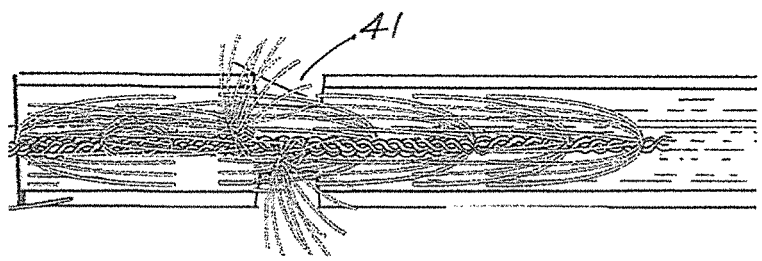

Referring now to FIG. 27 there is illustrated a bristle device 37 with a diameter larger than the lumen, deployed such that the bristles point along the direction of flow within the lumen. FIG. 28 shows a schematic in which a prosthesis 38 is deployed with the bristles pointing the opposite direction of the flow.

The force of the flow against the prosthesis could cause it to migrate. If the direction of flow (force) is opposite to the direction in which the bristles point along the lumen, the force required to move the device will be smaller than the case in which the direction of the flow (force) is the same as the direction along which the bristles point in the lumen. This is due to the interaction of the tips of the bristles with the vessel wall and the resulting friction—the tips of the bristles help anchor the prosthesis in the lumen if any movement of the device begins to occur.

As the direction of action of the flow may not always be predictable, it may be preferable to ensure that, when deployed, the bristle device has some bristles oriented in one direction, and other bristles oriented in the opposite direction. A physician may wish to use different approaches to deploy the device, which may or may not lead to a desirable bristle direction with respect to the flow direction.

When a bristle device is pulled into a loading tube 20 to be pushed into a delivery catheter 26, its bristles are aligned within the loading tube such that they point distally when in the catheter. This means that all bristles will point one direction when the prosthesis is deployed. As explained above, this means that the device will have lower force to migration in one direction than the other.

In one embodiment of the invention a loading tube is provided which is configured to reorient at least some of the bristles while the bristle device is being pushed into the delivery catheter.

Referring to FIGS. 29 to 34 in one case a loading tube 40 contains reorientation slots 41 which allow the bristles to spring out while the bristle device 25 is being pushed into the delivery catheter 26. Subsequently, as these bristles encounter the end of the slot 41 while the device is being pushed into the delivery catheter 26, they are forced to collapse and realign, pointing in the opposite direction to the direction they had originally pointed.

The loading tube may be adapted to include a means to open or close the hole depending on the wishes of the physician to change or not change the orientation of the bristles.

Ideally an embolisation device should interact with the entire surface area of the target lumen. This has multiple benefits:
- Assists denudation of the endothelium of the lumen wall, which is known to aid in lumen embolisation.
- Occludes the lumen along its entire length and cross sectional area thereby preventing recanalization via a collateral or side-branch into the target lumen.
- Leads to a permanent occlusion thus reducing the risk of surgical failure and the requirement for a repeat procedure.
- Greater interaction with the vessel wall helps lock the implant in position thereby reducing the risk of implant migration.

Removing or damaging the endothelium has a critical role to play in the clotting cascade within a lumen. When the endothelium is removed, the normally isolated, underlying collagen is exposed to circulating platelets, which bind directly to collagen, which is released from the endothelium and from platelets; leading to the formation of a thrombus. If the device does not provide adequate lumen conformance and coverage then recanalization can occur. This coverage should be maximised not only in terms of vessel cross section but also vessel wall area also. In spermatic vein occlusion, a liquid (e.g. sclerosant, which has greater lumen conformance and coverage capabilities than coils) results in higher technical success and lower recanalization rates than coils alone [8]. However, damage to the endothelium should be done without causing vessel perforation. This could lead to catastrophic events such as internal bleeding. This is shown schematically in FIG. 35.

In another aspect of the invention a bristle device is provided which has a larger unconstrained diameter than the target vessel and which incorporates bristles which are flexible enough to conform to the vessel anatomy and which will not cause vessel perforation i.e. delivery force to the vessel wall is not sufficient to perforate.

Figure 36:
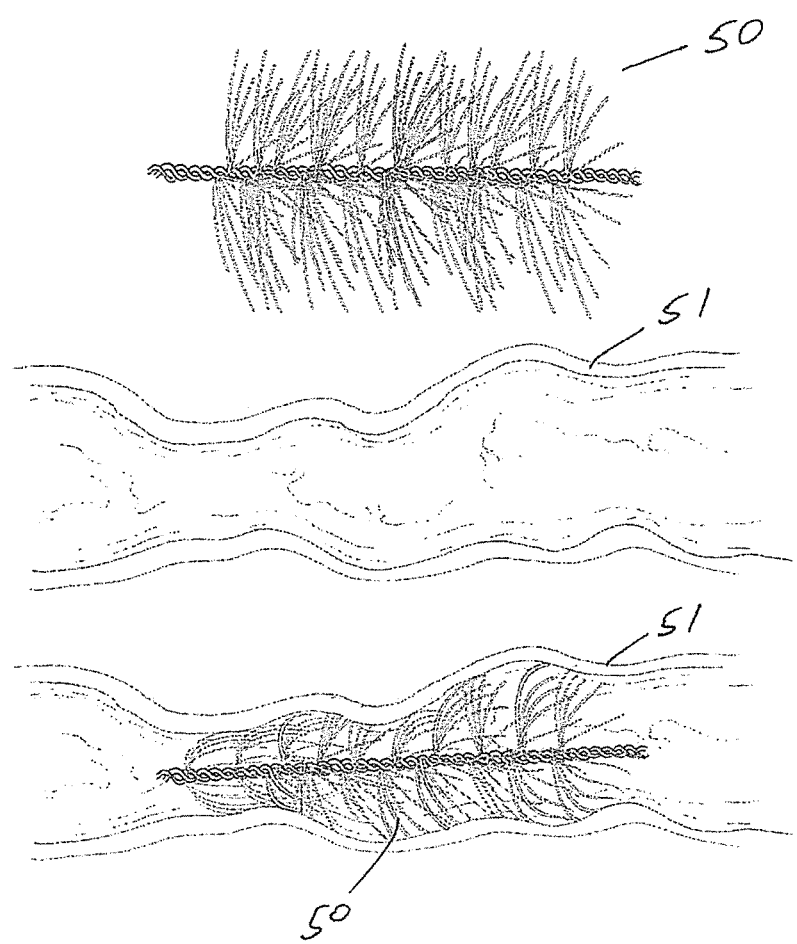
FIG. 36 illustrates a bristle device with flexible fibres for vessel conformance.

FIG. 36 shows a prosthesis 50 for deployment in a lumen 51 with a varying lumen diameter. When deployed in a lumen with a varying diameter, the device can conform to the variations in the lumen diameter without causing lumen perforation. This is due to the flexibility of the fibres of the prosthesis which, while providing an anchor within the lumen, are not too stiff to perforate the lumen.

The potential for the fibres to perforate the vessel is dependent primarily on the fibre material, fibre diameter and the surface area of contact between the fibre and the vessel wall. A fibre with a low stiffness may have the potential to perforate the vessel if its stiffness is high enough due to a large diameter (and potentially a sharp bristle tip).

The fibres may be of a radiopaque material to enable the physician to visualise the device using x-ray.

| Material | Diameter Less Than: |
|---|---|
| Nitinol | <0.015 |
| Platinum | <0.015 |
| Stainless Steel | <0.015 |
| Polyester | <0.015 |
| PTFE | <0.01 |
| Nylon (Polyamide) | <0.015 |
| Polypropylene | <0.015 |
| PEEK | <0.015 |
| Polyimide | <0.015 |
| Pebax | <0.015 |
| Polyurethane | <0.015 |
| Silicone | <0.015 |
| FEP | <0.015 |
| Polyolefin | <0.015 |

FIGS. 37 to 39 illustrate various embodiments in which lumens with non-uniform diameters may be treated using a prosthesis which has conforming geometries. FIG. 37 shows a "dog-bone" shaped prosthesis 55. FIG. 38 shows a tapered prosthesis 56 suitable for a tapered lumen. FIG. 39 shows a prosthesis 57 suitable for a lumen with a step-change in diameter.

Referring to FIG. 40 in another embodiment a bristle device 58 in which at least some of the bristles are stiffer and impose the geometry of the bristle device on the vessel wall. This occurs because the diameter of the bristle device is larger than that of the target vessel.

A Method to Treat Haemorrhoids

Background

Hemorrhoids, often described as "varicose veins of the anus and rectum," are a common condition in which the veins lining the anus or lower rectum become swollen and inflamed.

Hemorrhoids are varicosities of the hemorrhoidal plexus (rectal venous plexus). This plexus communicates with the uterovaginal plexus and drains, via the rectal veins, into the internal pudendal vein and internal iliac vein. Although the exact cause of hemorrhoids remains unknown, standing too long in an upright position exerts pressure on the rectal veins, which often causes them to bulge.

There are two types of hemorrhoids: external and internal, which refer to their location. External hemorrhoids develop under the skin around the anus; if a blood clot develops in one of them (in a condition known as thrombosed external hemorrhoids), a painful swelling may occur. External hemorrhoids are characteristically hard and sensitive, and bleed upon rupture. Internal hemorrhoids are sac-like protrusions that develop inside the rectal canal. Painless bleeding and protrusion during bowel movements are the most common symptoms of internal hemorrhoids; however, they may cause severe pain if they become completely prolapsed, or protrude from the anal opening.

Hemorrhoidectomy, the surgical removal of hemorrhoids, is recommended for third- and fourth-degree internal hemorrhoids (with or without external hemorrhoids). The two major types of hemorrhoidectomy operations are the closed (Ferguson) hemorrhoidectomy and the open (Milligan-Morgan) hemorrhoidectomy. Both techniques are performed using a variety of surgical devices, including surgical scalpel, monopolar cauterization, bipolar energy, and ultrasonic devices.

Complications associated with Hemorrhoidectomy include [17]:
  Urinary retention following hemorrhoidectomy is observed in as many as 30 percent of patients
  Urinary tract infection develops in approximately 5 percent of patients after anorectal surgery
  Delayed hemorrhage, probably due to sloughing of the primary clot, develops in 1 to 2 percent of patients; it usually occurs 7 to 16 days postoperatively. No specific treatment is effective for preventing this complication, which usually requires a return to the operating room for suture ligation.
  Fecal impaction after a hemorrhoidectomy is associated with postoperative pain and opiate use. Most surgeons recommend stimulant laxatives, stool softeners, and bulk fiber to prevent this problem. Should impaction develop, manual disimp action with anesthesia may be required.

An alternative to hemorrhoidectomy is stapled hemorrhoidopexy, in which an intraluminal circular stapling device resects and resets the internal hemorrhoid tissues. When the stapler is fired, it creates a circular fixation of all tissues within the purse string to the rectal wall. In effect, it will draw up and suspend the prolapsed internal hemorrhoid tissue.

This procedure is best utilized when offered to patients with significant prolapse, such as those with grade II, grade III, or IV internal hemorrhoids. This procedure does not effectively treat most external hemorrhoids, and often requires separate excision of the external component when performed on patients with combined disease.

Neither procedure is effective at inducing long-term relief. In a randomized trial of stapled hemorrhoidopexy versus hemorrhoidectomy, the procedures were equally effective in preventing recurrence after one year [18]. Patients undergoing hemorrhoidectomy were more likely to have symptomatic relief from the hemorrhoids (69 versus 44 percent with hemorrhoidopexy), but had significantly greater postoperative pain [18].

It has been demonstrated that embolisation of the internal iliac veins removes reflux from hemorrhoidal plexus. Some dimishment and/or disappearance of hemorrhoids has been associated with embolisation of refluxing pelvic and internal iliac veins (16). Technical success of embolisation of the internal iliac or hypogastric veins has been reported to be 85% [9,10].

In the clinical literature, caution has been advised when embolising the internal iliac vein tributaries where there is clinically significant communication with veins of the lower limb; as this communication between the obturator and the common femoral veins increases the risk of coil migration and displacement into a deep vein [5]. Displacement into a deep vein can have serious consequences if the coil led to a deep vein thrombosis [5]. Accordingly, a safe and effective device is still required for embolisation of the internal iliac veins for the treatment of hemorrhoids.

In one aspect of the invention a method for the treatment of haemorrhoids is proposed in which a bristle device is implanted in the internal iliac, or hemorrhoidal veins to cause permanent occlusion. This occlusion will prevent venous reflux to the hemorrhoidal plexus, which causes hemorroids.

Figure 125:
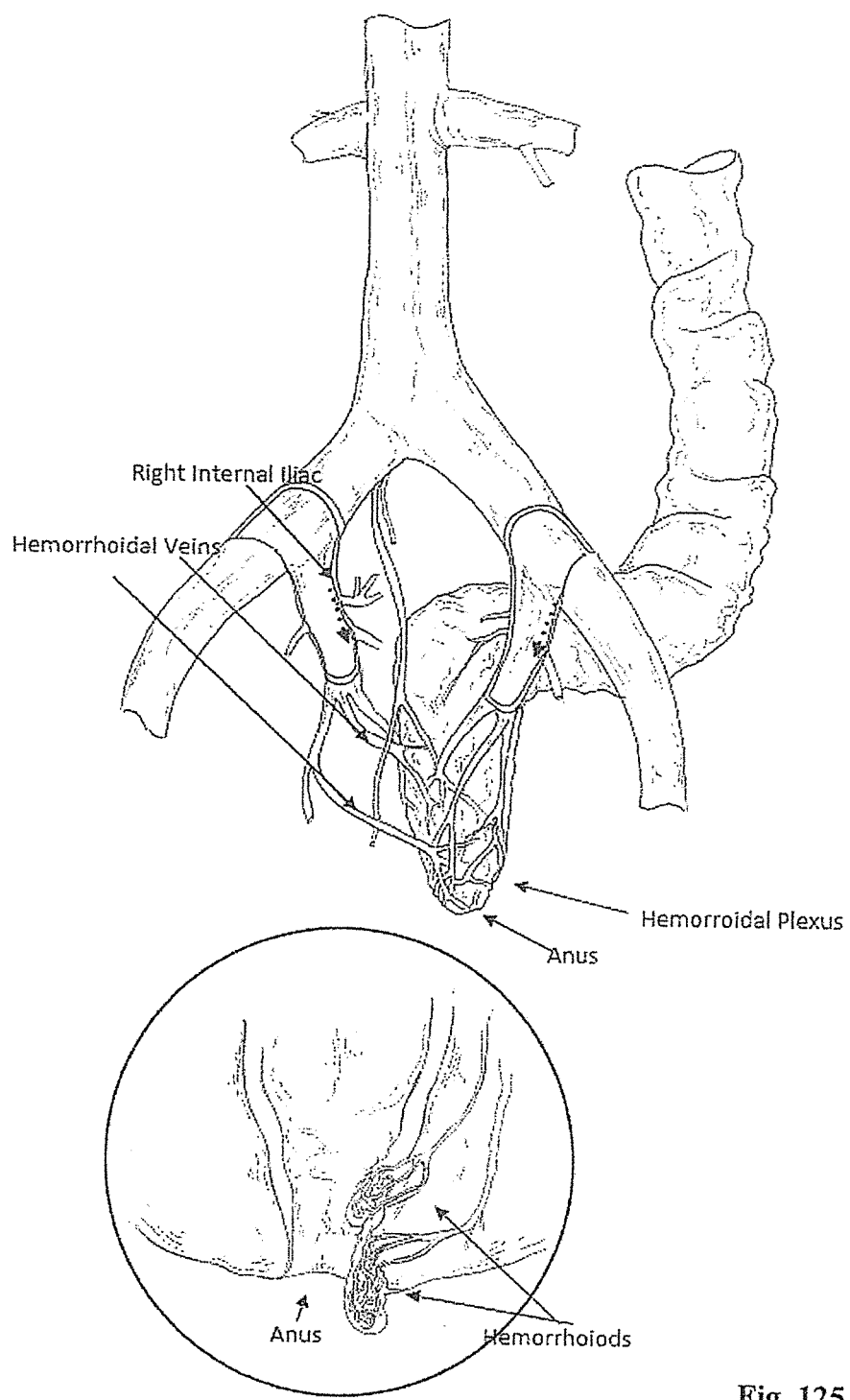

FIG. 125 is a schematic showing the venous anatomy relating to the presence of a haemorrhoid (detailed view of cross section of anus). The broken arrows show direction of venous reflux through internal iliac veins leading to varicosities off the haemorrhoidal plexus, causing haemorrhoids.

Figure 126:
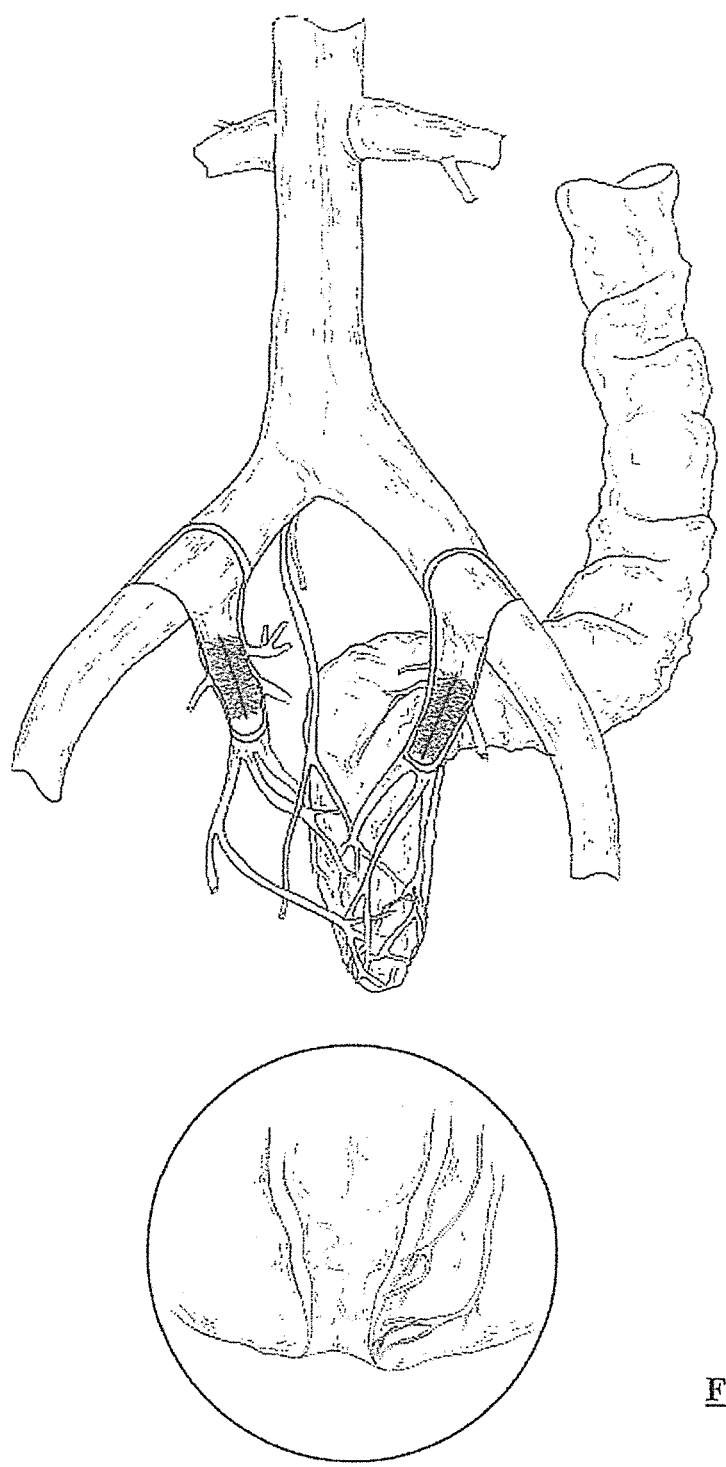

FIG. 126 illustrates the insertion of bristle devices in internal iliac veins has arrested refluxing flow to the haemorrhoidal veins and caused the haemorrhoid to disappear.

Figure 41:
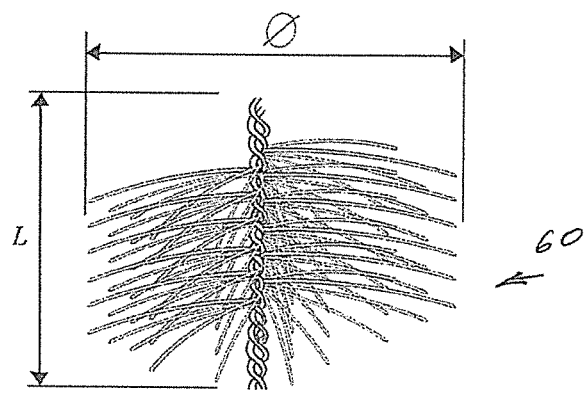
FIG. 41 illustrates a bristle device with length and diameter attributed.

FIG. 41 shows a bristle device 60 with a length, L, and a diameter, ø. The stability of the device during and after deployment from a catheter is dependent upon the ratio of these quantities with respect to the vessel diameter. Ideally, the bristle device should have a diameter greater than or equal to the target lumen, and a length to diameter ration, L/ø, of 1.0 or greater.

Figure 42:
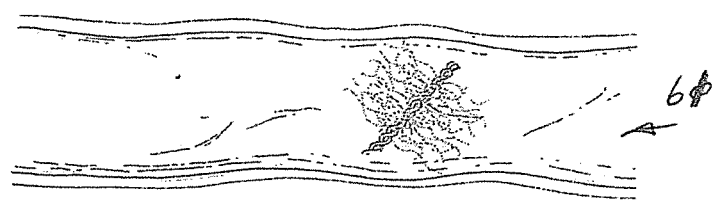
FIG. 42 shows the negative effect of a low length to diameter ratio.

FIG. 42 shows a bristle device 61 with a ratio L/ø<1 deployed in a lumen. The prosthesis has become unstable during, or after, deployment and consequently now lies at an angle to the long axis of the lumen. Due to a L/ø ratio <1 the device could migrate, recanalise or damage the lumen wall. The low length to diameter ratio also means that the prosthesis could "pop" out of the catheter making it difficult to deploy accurately to the target site.

Figure 43:
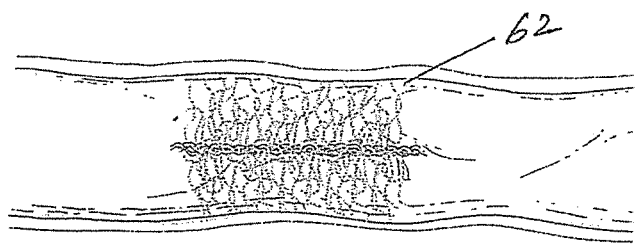
FIG. 43 illustrates a bristle device with a high length to diameter ratio.

FIG. 43 shows a bristle device 62 according to the invention with L/ø>1.0. In this case the prosthesis is correctly aligned, is stable and is unlikely to migrate or cause damage to the lumen wall.

Figure 44:
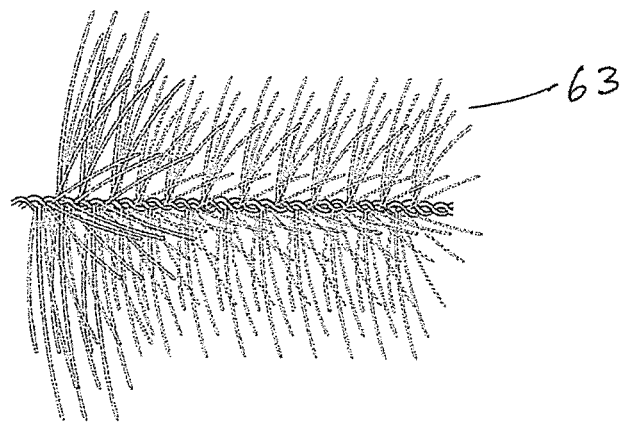
FIG. 44 illustrates a bristle device with distal anchoring fibres.
Figure 45:
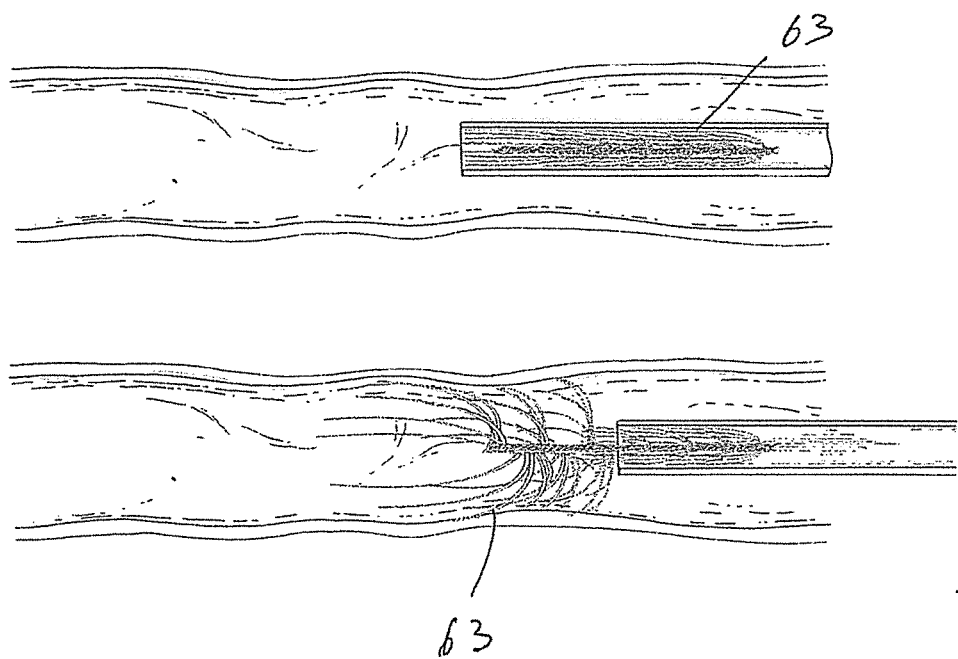
FIG. 45 shows the use of longer bristles at the ends acting as stabilisers.

Referring now to FIGS. 44 and 45 in this case a bristle device 63 has longer bristles at the distal end (the end which will be deployed first from the catheter). These longer bristles are intended to act as "stabilisers" upon initial partial deployment of the prosthesis. The longer bristles extend distally along the vessel wall providing and anchor, ensuring the prosthesis cannot "pop" forward from delivery catheter upon completion of deployment.

Figure 46:
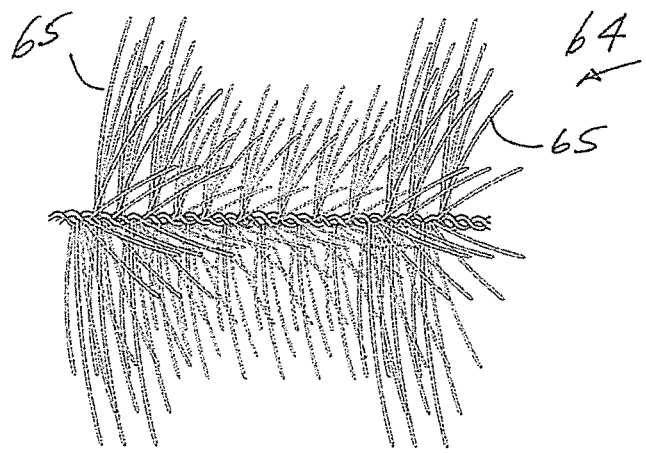
FIG. 46 illustrates a bristle device with stabilisers on both ends.

The prosthesis may have stabilising bristles 65 at one or both ends of a prosthesis 64 as illustrated ion FIG. 46.

Figure 47:
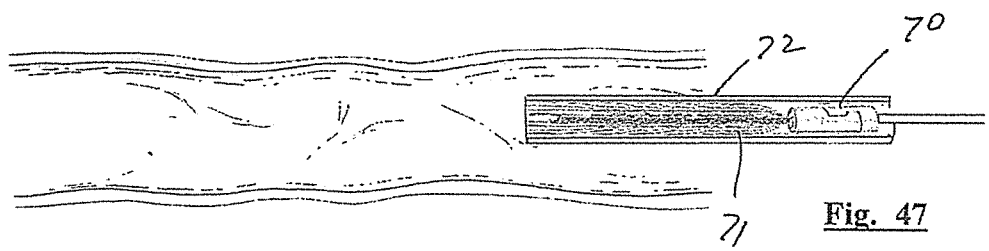
FIGS. 47 to 49 illustrate a delivery system having a slot detachment mechanism.
Figure 48:
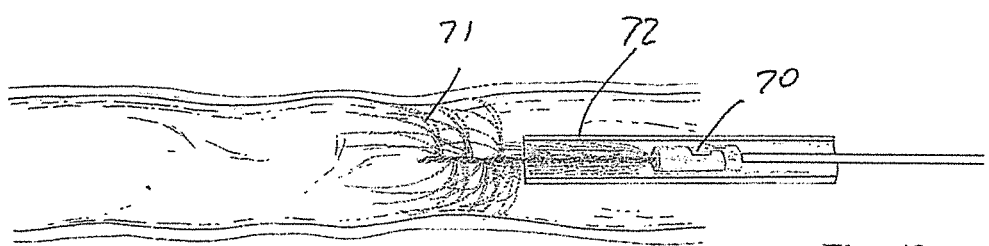
Figure 49:
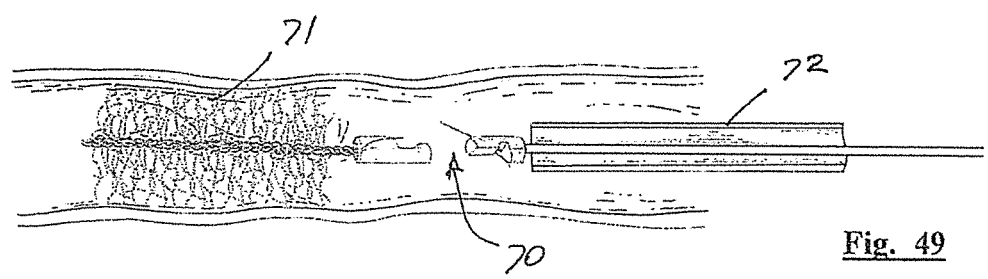

FIG. 47 shows a bristle device 71 in the collapsed configuration within a delivery catheter 72. A slot mechanism 70 is incorporated to enable detachment once the device is fully deployed. The slot detachment mechanism 70 may be radiopaque to enable the physician to establish the position of the mechanism with respect to the catheter tip. FIG. 48 shows the bristle partially deployed. In this configuration the slot detachment mechanism is still engaged since the bristle device cannot move off the axis of the delivery catheter and wire. Accordingly the physician may still retract the bristle device at this point. FIG. 49 shows the bristle device in the deployed configuration. Since the bristle device has exited the catheter it is not constrained to remain on the same axis of the delivery wire and becomes disengaged from the delivery wire.

Figure 50:
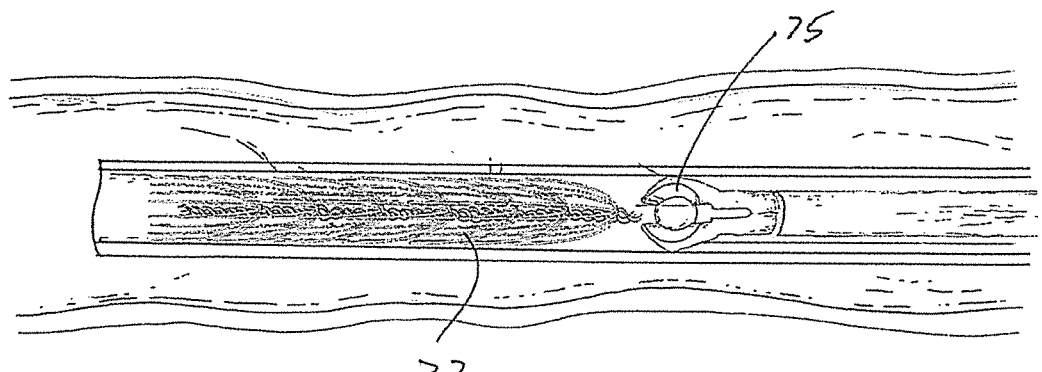
FIGS. 50 to 52 illustrate a bristle device with another detachment feature.
Figure 51:
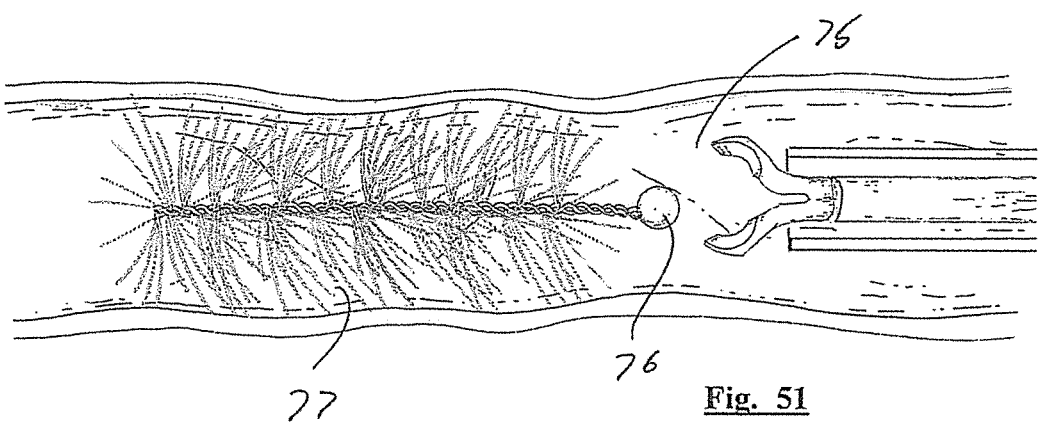
Figure 52:
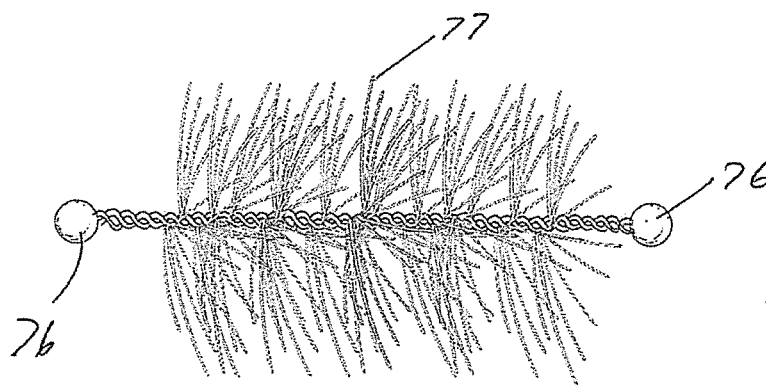

In another embodiment, and referring to FIGS. 50 to 52 a delivery wire with a normally open grasping mechanism 75 illustrated. The grasping mechanism is designed to fit snugly around a ball end or lip 76 on a bristle device 77. This mechanism 75 will always be open if not constrained by the catheter wall. Once the bristle device has been pushed out of catheter, the grasping mechanism 75 pops open detaching the bristle device. Until this point the device can be retracted. Equally this type of mechanism could be used to retrieve the detached bristle device by forcing the normally mechanism closed as it is retracted into the catheter.

FIG. 52 illustrates a bristle device with ball features 76 on both ends.

Figure 53:
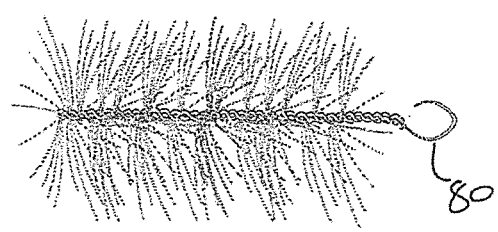
FIGS. 53, 54 and FIGS. 55, 56 illustrate bristle devices with further detachment features.
Figure 54:
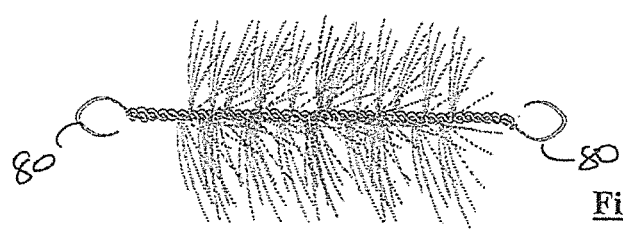

FIGS. 53 and 54 show a bristle device with a hook type mechanism 80 for detachment and retrieval. The bristle device may have a hook at one, or both ends. To ensure that lumen perforation cannot occur, the hook end does not project towards the lumen wall, but towards the bristle portion of the device instead.

Figure 55:
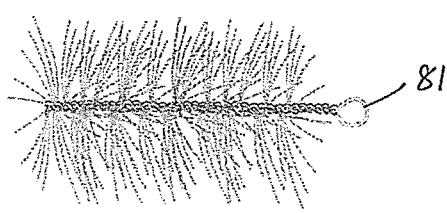
Figure 56:
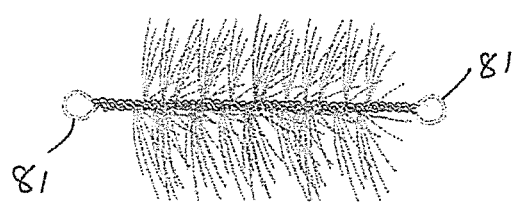

FIGS. 55 and 56 show a bristle device with a loop type mechanism 81 for detachment and retrieval. The bristle device can have a retrieval mechanism at one, or both ends. In this embodiment, the retrieval loop is created by forming the end of the twisted wire of the bristle burn.

Figure 57:
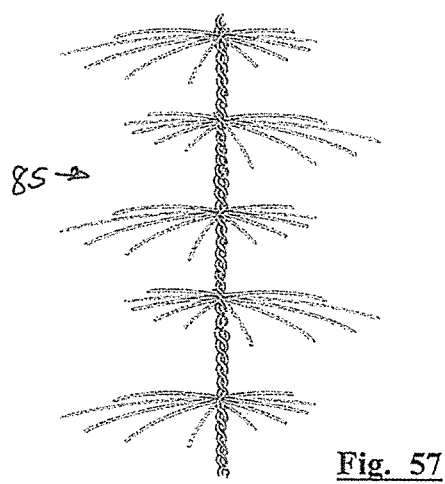
FIGS. 57 and 58 illustrate a bristle device with non uniform bristle lengths.
Figure 58:
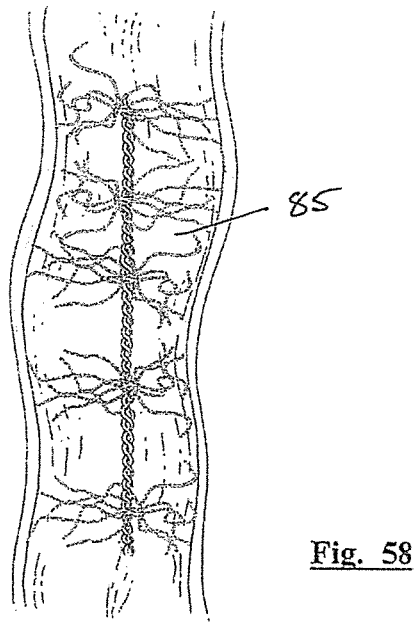

FIG. 57 shows a bristle device 85 with non-uniform bristle lengths about the circumference and along the device length. Variations in the bristle length will reduce the potential for bristle device migration. FIG. 58 shows the device of FIG. 57 deployed in a lumen.

Shorter bristles are less likely to buckle and can therefore transmit a greater load to the lumen wall, increasing the radial or "anchor" force of the device in the lumen, particularly within non-uniform lumen diameters.

Imposition of undulations, roughness and non-uniformity in the lumen wall will increase the resistance to migration of the device due to increased friction.

Figure 59:
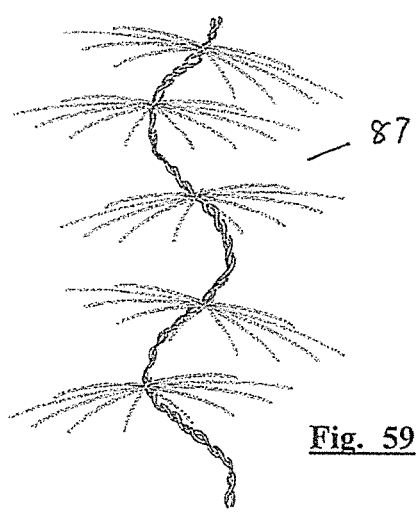
FIGS. 59 and 60 illustrate another bristle device with a curved core and a diameter less than that of the target lumen.
Figure 60:
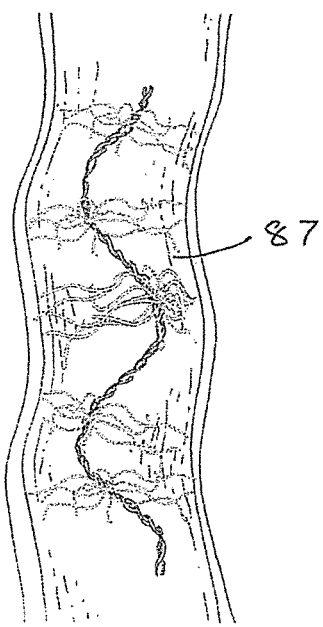

FIG. 59 shows a bristle device 87 with a curved core or stem. In a preferred embodiment the core is helical, and the diameter of the helix is less than the diameter of the lumen. This configuration forces the bristles against the lumen wall, such that the radial force of the bristle device is not dependent on the outward force of the length and diameter of the bristles alone, but also on the distance subtended by the core to the lumen wall. This will increase the anchor force locally and cause undulations/roughness in the lumen wall increasing the resistance to migration. FIG. 60 shows the bristle device 87 deployed within the lumen.

Figure 61:
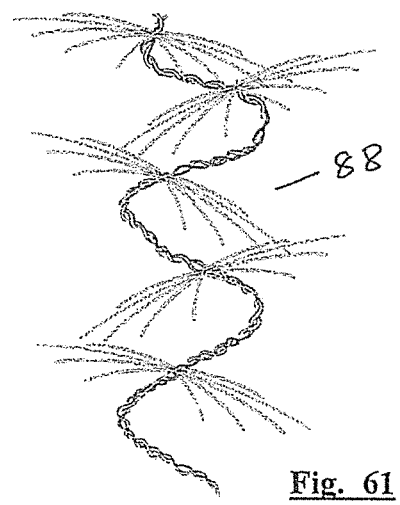
FIGS. 61 and 62 show a further bristle device with a curved core and a diameter greater than that of the target lumen.
Figure 62:
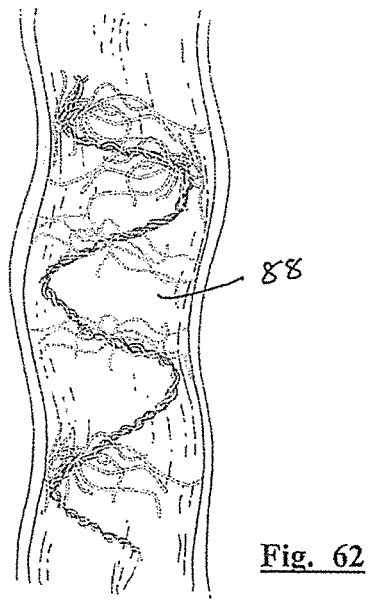

FIGS. 61 and 62 illustrate a bristle device 88 in which a core wire is curved and the external diameter of the core is greater than that of the lumen. This configuration forces both the bristles and the core wire against the lumen wall. In this case the radial force of the bristle device is a combination of both bristle and core, but is dominated by outward force of the core.

Figure 63:
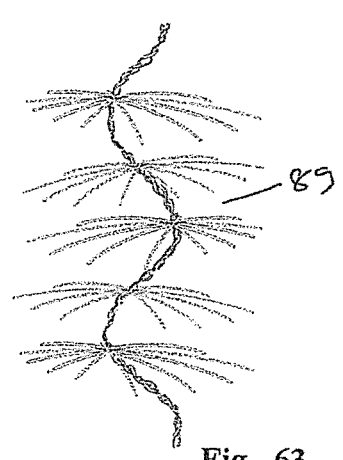
FIGS. 63 and 64 show a bristle device with a curved core and variable bristle lengths.
Figure 64:
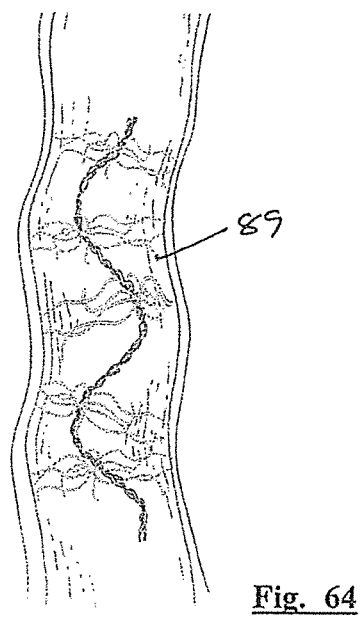

FIGS. 63 and 64 illustrate a bristle device 89 with a curved core and non-uniform bristle length. In this configuration, the bristle device is configured such that the bristle device has a curved core, and variable bristle lengths about the circumference and along the length.

Figure 65:
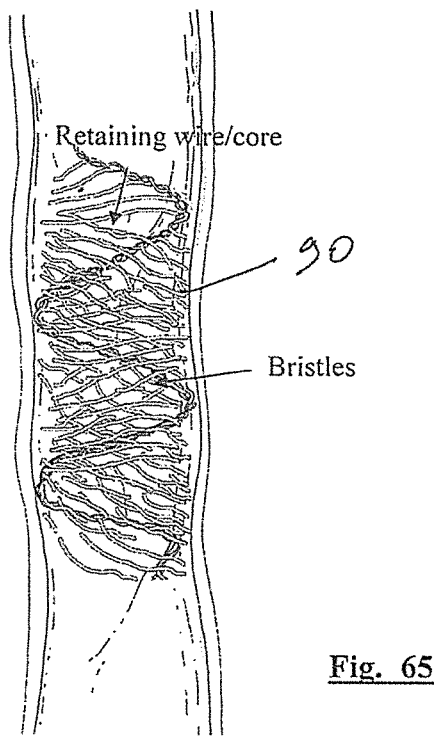
FIGS. 65 and 66 show a bristle device with bristles pointing inwardly from a retaining wire.
Figure 66:
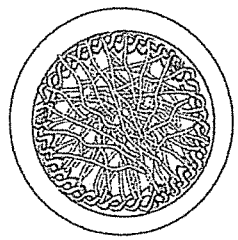

FIGS. 65 and 66 illustrate another embodiment of a bristle device 90 in which all bristles point inward from a retaining wire. In this case the device is anchored entirely by the core/retaining wire.

To enable the physician to deliver the bristle device through tortuous anatomy it must be flexible. This also enables the bristle device to conform to tortuous anatomy once implanted. The flexibility of the prosthesis is defined, primarily, by properties of the core to which the bristles are attached. The flexibility of the core is a function not only of the amount of material in the core, but also its distribution, and material (lower modulus means greater flexibility).

There are certain clinical indications where the optimal clinical outcome would be to simultaneously embolise a vessel and an adjoining, diverging division.

Such a clinical situation is the prophylactic embolisation to prevent type II endoleak pre-endovascular aneurysm repair (EVAR). Type II endoleaks can be identified during angiography by the presence of contrast travelling from a peripherally catheterized vessel into the excluded aneurysm sac. The objective when embolising pre-EVAR is permanent occlusion of the internal iliac artery proximal to its bifurcation to ensure that there is complete occlusion before proceeding to EVAR, as any leak will cause reoccurrence of the issue. Using an angled, adjacent vessel to anchor a portion of the device while deploying the majority of the same device in the larger vessel would provide an anchor for the device, preventing future migration.

Additionally, the internal iliac vein bifurcates into anterior and posterior divisions, which supply pelvic organs as well as the gluteal muscles. It is frequently necessary to embolise one of the anterior or posterior divisions as well as the internal iliac vein. The same approach as described previously would be advantageous; embolising the adjacent tributary while retracting the remainder of the device to occlude the higher order vessel.

A bristle device, which has the flexibility to be deployed across bifurcating vessels, may be preferable in these instances.

Figure 67:
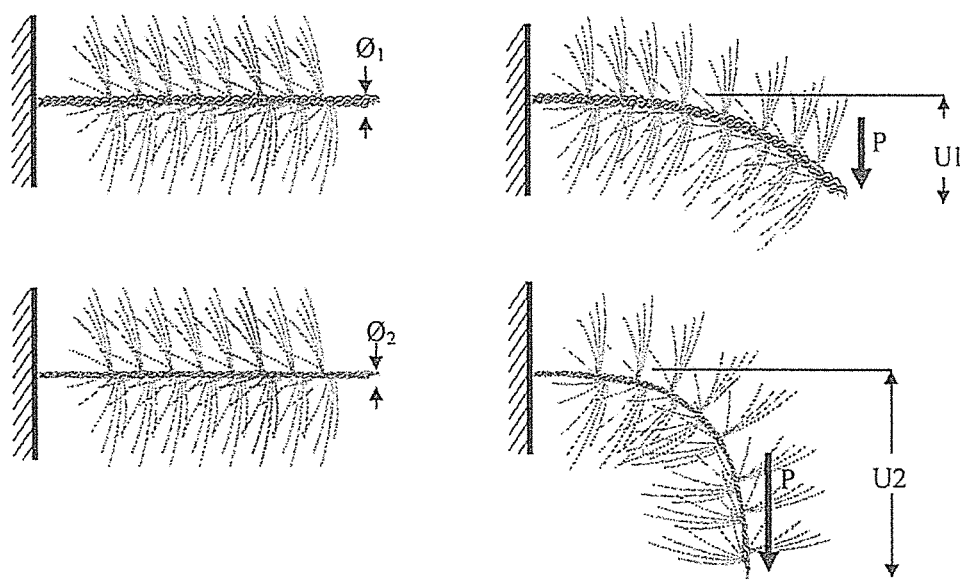
FIG. 67 illustrates the effect of core diameter on flexibility.

FIG. 67 illustrates two device prostheses of the same length with different core wire diameters, $ø_1$ and $ø_2$, where $ø1>ø_2$, Note: it is assumed that the core is approximately of circular cross section. One end of the prostheses is fixed and a load, P, is applied to the opposite end causing deflection of the prosthesis. The deflection of the larger diameter device, U1, is much smaller than that of the lower diameter device (U2).

Considering a bristle device with a stainless steel core constructed from twisted wire, its diameter should preferably be constructed from twisted wires of diameter 0.02 inches or less. Otherwise it may not be possible to track the device to the target vessel for deployment.

Figure 68:
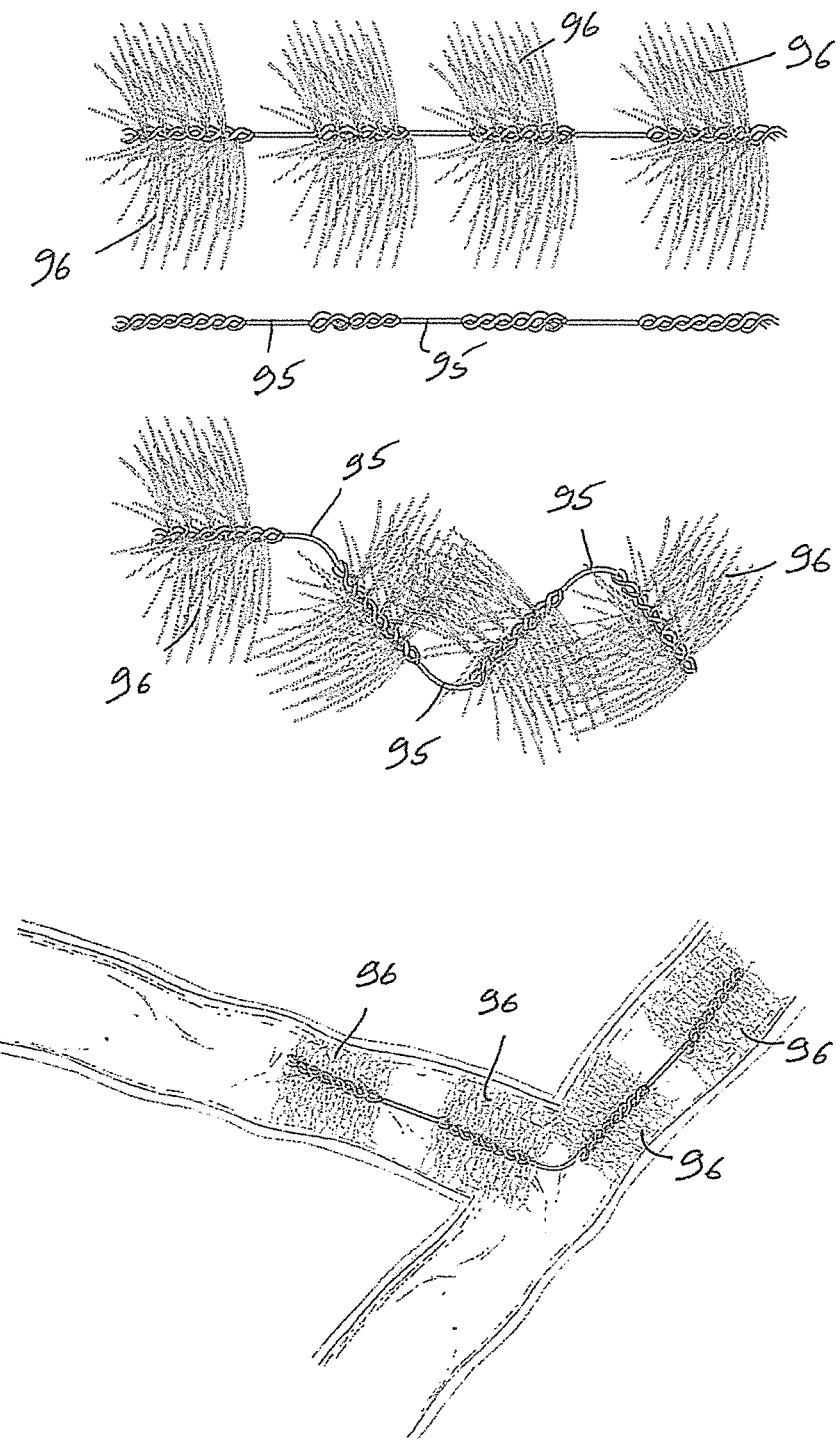
FIG. 68 shows a bristle device with flexible sections and application to bifurcated vessels.

In other embodiments, the flexibility of the device could be improved by having flexible sections 95 between device sections 96 as shown in FIG. 68. Bending within the device is taken up, primarily, by the flexible sections, which can articulate to enable it to pass through a catheter placed in tortuous anatomy, or to be deployed in a curved vessel, or across a bifurcation. In this case the bristle device has flexible sections for articulation Directional control of fluids (e.g. contrast media for angiographic visualization, sclerosant for vessel embolisation) cannot be achieved with today's embolisation technology. Currently the physician has limited control over fluid dispersion. The current technique involves flushing the fluid through the lumen of a catheter proximal to the target location.

This is of significant relevance in male and female varicocele embolisation. A varicocele is a varicose dilation of the pampiniform plexus that drains the testicle and epididymis. The pampiniform plexus drains into the internal spermatic vein. Additional small veins drain into saphenous, external iliac, and internal iliac systems.

For specific embolisation procedures e.g. varicocele, additional coils must be deployed in the cephalad portion of a vessel to ensure that that the coils occlude the main branch and all accessible collaterals [7]. To minimize the risk of recurrence, it is often necessary to isolate the most distal (caudal) segment of the target vessel from any potential collateral supply. An alternative to coils is to use an occlusion balloon.

Furthermore in some patients, collateral parallel channels must be selectively catheterized and occluded, either with coils, sclerosant, glue or other embolic agents. When using sclerosants, the intention is to destroy the endothelium to expose subendothelial tissues that in turn will lead to irreversible vascular fibrosis. For certain embolisation procedures, e.g. varicocele, if the scleroscant migrates too distally adverse effects can occur e.g. approximately 10% of males develop testicular phlebitis [8].

The sclerosant effect largely depends on a) the time it is in contact with the endothelium and b) the volume and rate of injection [8]. Controlling these variables significantly influence the outcome and also the propensity to damage adjacent non-target vessels.

This proximal migration of the fluid is often referred to as reflux. In some cases, this fluid may contain a drug, sclerosant, fibrin, thrombin, glue, alcohol, beads, or drug coated beads. The physician may require accurate delivery of these agents to prevent non-target therapy.

In the invention a bristle device may be used to prevent proximal migration of a fluid during delivery using a catheter.

When implanted, a bristle device causes a resistance to flow through the device. Similarly, the construction of the device itself means that flow is initiated within the device itself, the flow will have a lower resistance laterally than axially, and will be inclined to fill up any available space outside of the device rather than travel axially through the device itself. Consider the following steps in order to inject a fluid into a vessel, wherein the direction of the flow is controlled using a bristle device.
1. A bristle device is deployed distal to the location in which it is intended to deliver the fluid
2. The bristle device is crossed using a catheter such the tip of the catheter resides on the distal side of the bristle device.
3. The fluid is injected through the catheter tip. It is prevented from migrating through the bristle device and will fill any vessels distal to the device.

Figure 69:
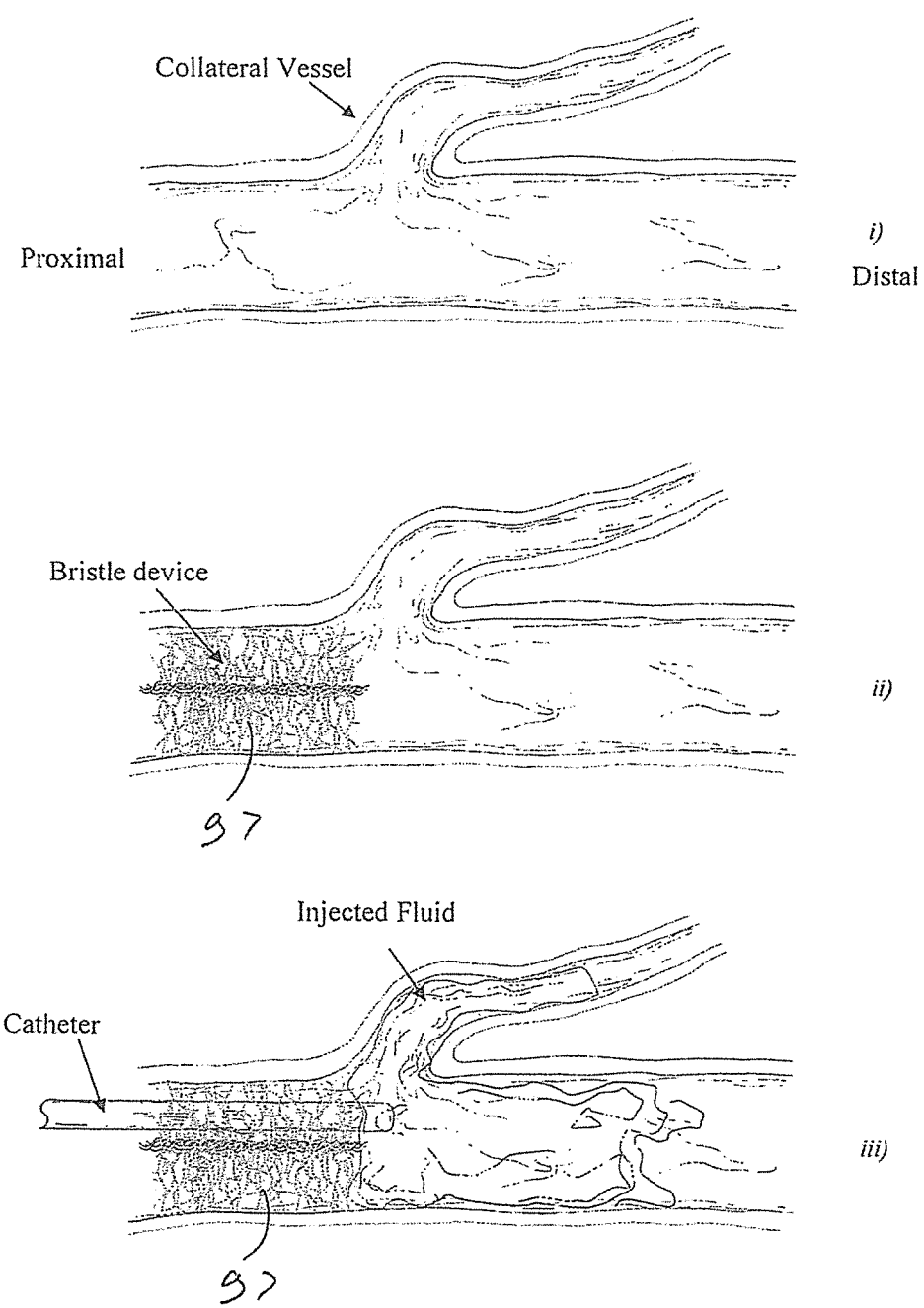
FIG. 69 illustrates the control of fluid using a bristle device.
Figure 70:
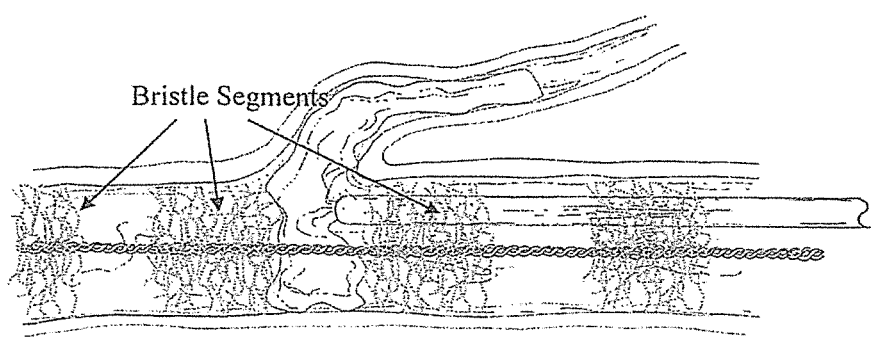
FIGS. 70 to 72 illustrate the uses of bristle devices.

FIG. 69 illustrates a bristle device 97 in use to prevent proximal migration of a fluid during delivery using a catheter.

Figure 71:
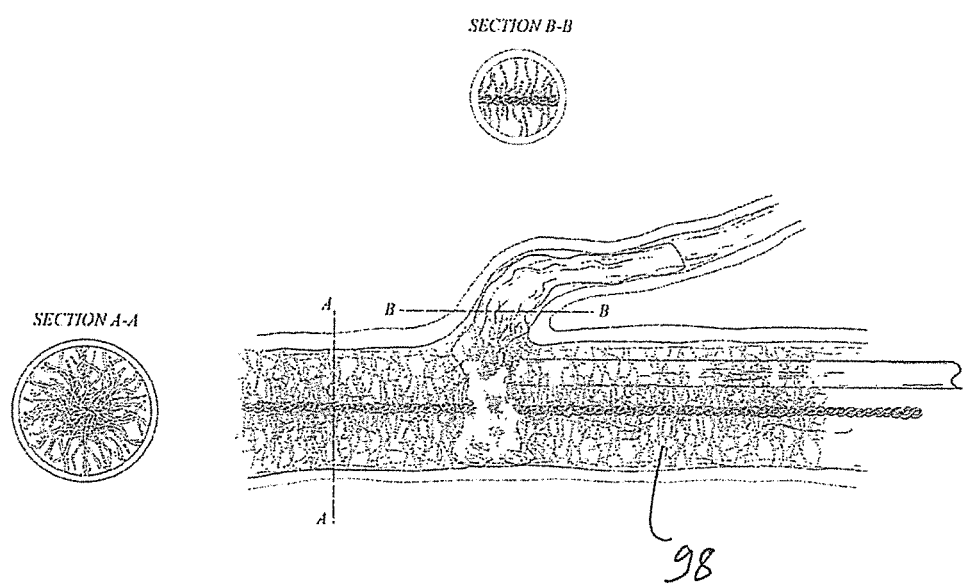

In another embodiment, without the presence of individual bristle segments, the path of least resistance for flow is still laterally. This is because the density of bristles laterally is lower than that proximally and distally. Accordingly, the flow will naturally be laterally from the catheter tip. This enables treatment of a collateral vessel and is shown schematically in FIG. 71. FIG. 71 illustrates the use of a bristle device 98 to ensure lateral dispersion of a fluid. Note: Section A-A shows a much higher density of fibres meaning flow will have a higher resistance in this direction (axially) compared to laterally (Section B-B).

The presence of these gaps between the brush segments is also a means to reduce the profile of the bristle device when constrained for placement in a catheter. This is because effect of bristles lying on top of one another, increasing profile is limited.

Figure 72:
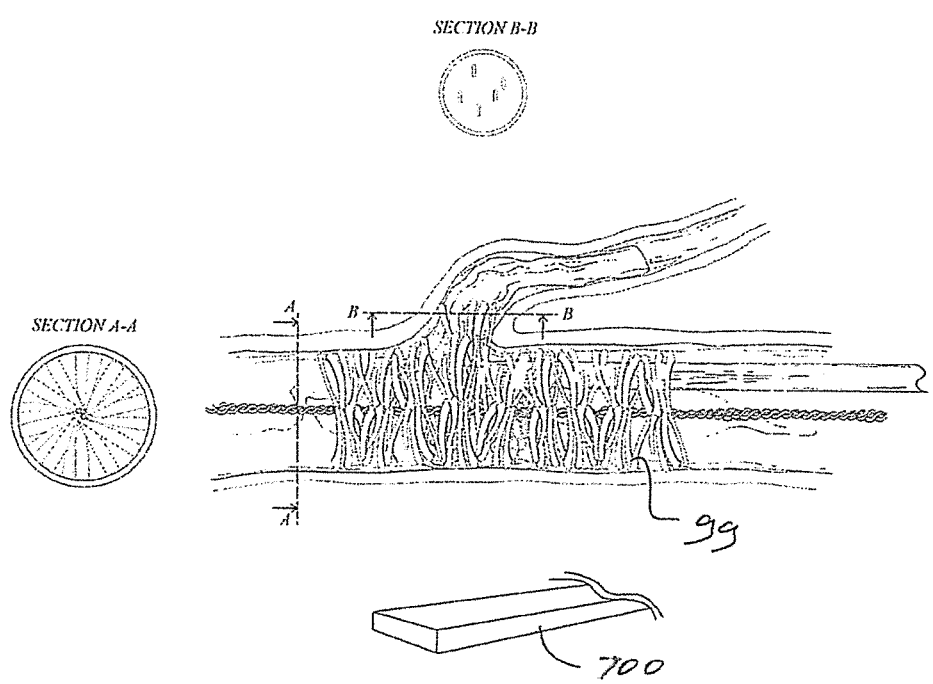

Referring to FIG. 72 in another embodiment, to further improve the ability of a bristle device 99 to prevent longitudinally flow (ensure lateral dispersion of a fluid), bristles with a rectangular cross section 100 are illustrated. The bristles are aligned such that the long axis of the bristle is perpendicular to the centreline of the main vessel. These bristles mean that the path of least resistance is laterally rather than distally or proximally. This can be observed by viewing Section A-A and B-B in FIG. 72. Clearly, it will be easier for a fluid to pass through B-B than A-A due to the geometry of the bristles.

A blood vessel wall is composed of three layers. The innermost layer is called the endothelium and is merely a layer of endothelial cells. The middle and outer layers are known as the medial and adventitial layers respectively.

It has been shown that denudation, or damage to the endothelial lining of a blood vessel can induce vasospasm, and inflammatory reactions leading to vessel occlusion. Removing or damaging the endothelium has a critical role to play in the clotting cascade within a vessel. When the endothelium is removed, the normally isolated, underlying collagen is exposed to circulating platelets, which bind directly to collagen, which is released from the endothelium and from platelets; leading to the formation of a thrombus.

Figure 73:
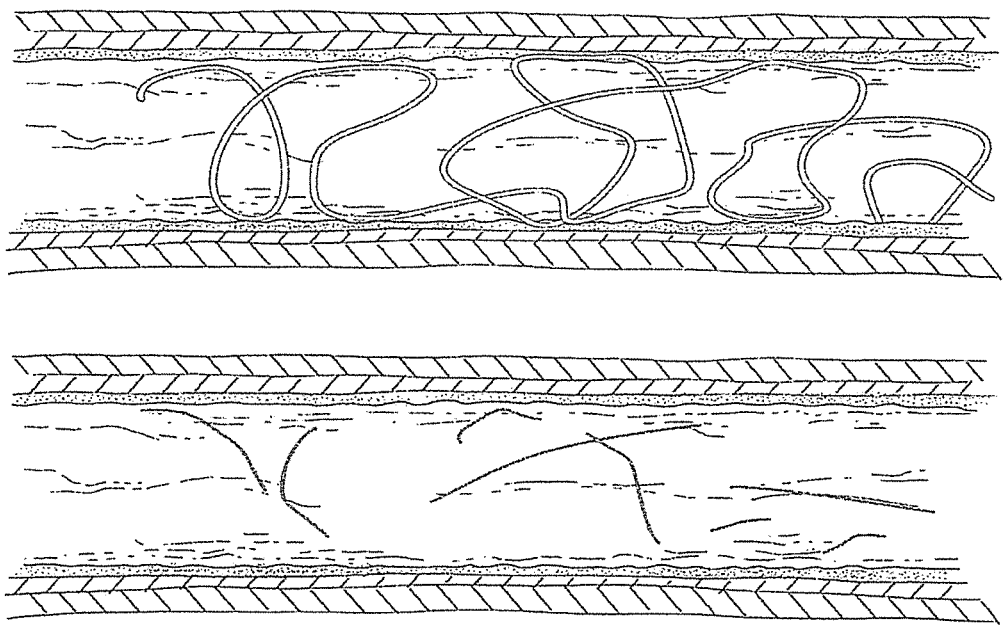
FIG. 73 are typical patterns of contact caused by coils.

Preferably, in order to induce the greatest damage to the endothelium, a bristle device should have a large number of fibres in contact with the lumen wall per unit surface area. Embolisation coils do not cause significant denudation to the vessel wall as the degree of wall contact is minimal. This can be seen in FIG. 73.

Figure 74:
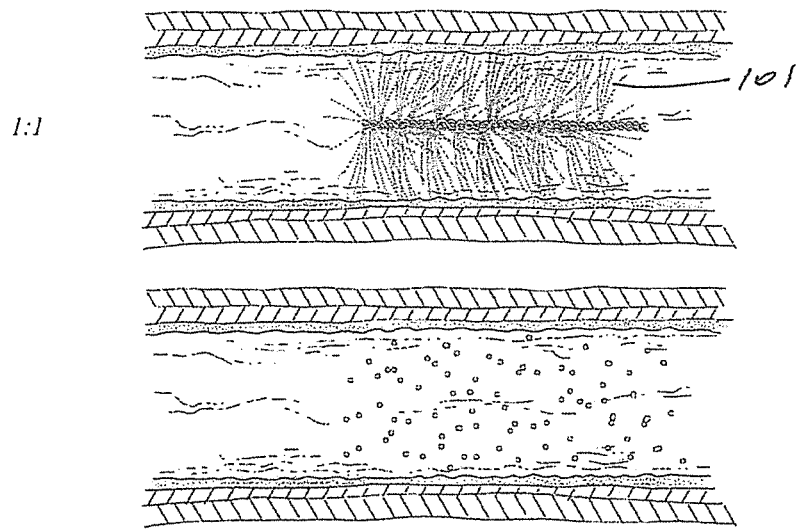
FIGS. 74 and 75 illustrate the effect of oversizing on surface area divided by a bristle device.
Figure 75:
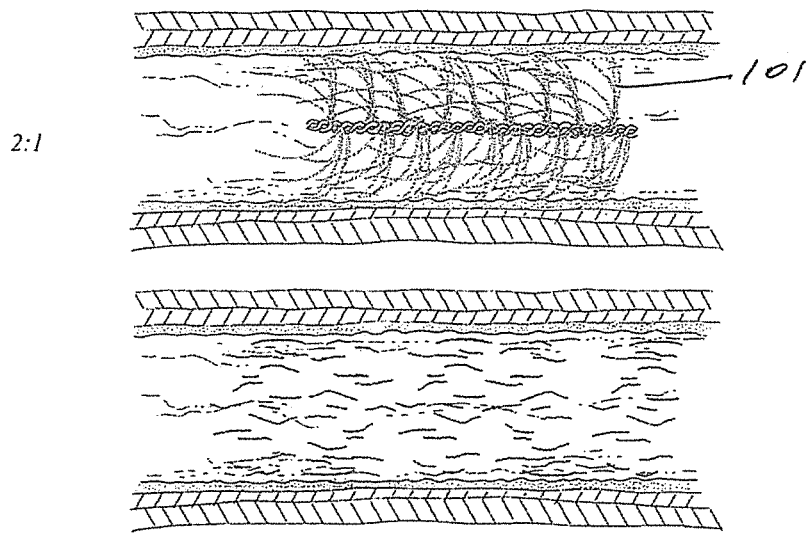

In order for a bristle device 101 to cause significant denudation of a vessel wall it should have a greater diameter than the vessel in which it is implanted. This ensures a larger contact area between fibres and the vessel wall as shown in FIGS. 74 and 75.

Figure 76:
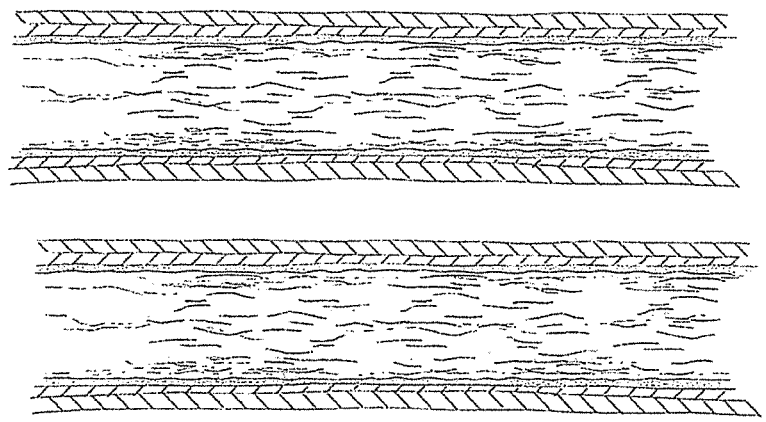
FIG. 76 illustrates the impact of bristle density on vessel damage.

Similarly, a greater number of fibres in contact with the vessel wall will have a greater impact in causing denudation and inducing embolisation. This is shown schematically in FIG. 76. This can be expressed in terms of the bristle length or area in contact with the vessel wall, per unit surface area of the vessel wall.

In some embodiments of the invention we provide
    a bristle device for embolisation with a device diameter to vessel diameter ratio of 1.1 or greater and/or
    a bristle device a minimum length of bristle of 1 mm in contact with a vessel surface area of 2 $mm^2$ and/or
    a minimum of 0.1% of the vessel surface area in contact with the bristle device fibres.

Figure 77:
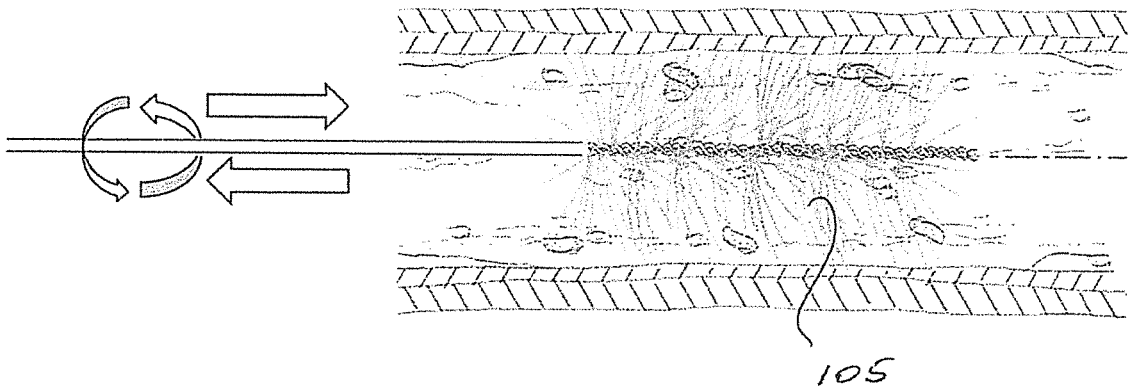
FIG. 77 illustrates a denudation technique using a bristle device.

In another embodiment, the bristle device could be used for denudation of the vessel wall by advancing, retracting and rotating the bristle device at the site of treatment. Once denudation is complete, the prosthesis can be left behind to promote permanent occlusion. FIG. 77 is a schematic showing denudation of the endothelium using translation and rotation of a bristle device 105. This "polishing" action will help strip the endothelial cells from the vessel and enhance the potential for vaso-occlusion. Once complete the prosthesis can be detached from the delivery wire and left in place.

The bristle devices of the invention are also suitable for the treatment of septal defects and patent foramen ovale.

Emboli leading to stroke or to transient ischemic attack can originate in either the systemic venous circulation (paradoxical emboli) or in the systemic arterial circulation. Some patients with cryptogenic stroke have a patent foramen ovale (PFO), an atrial septal defect (ASD), or an atrial septal aneurysm (ASA) that can be identified by echocardiography. These structures have been implicated in the pathogenesis of embolic events, leading to stroke.

Paradoxical emboli: a paradoxical embolus originates in the systemic venous circulation and enters the systemic arterial circulation through a PFO, atrial septal defect, ventricular septal defect, or extracardiac communication such as a pulmonary arteriovenous malformation [10]. The embolus can originate in veins of the lower extremities, in pelvic veins, in an atrial septal aneurysm, or from a clot around the edges of a PFO [10]. Patients with paradoxical emboli can present with cryptogenic stroke.

PFO and ASD: The foramen ovale and its flap-like valve between the right and left atrium are important components of the fetal circulation. In the developing fetus, oxygenated blood from the umbilical vein enters the right atrium via the inferior vena cava and is shunted into the left atrium, circumventing the non-inflated lungs. After birth, a relative increase in left atrial pressure closes the flap, and adhesions frequently result in a structurally intact atrial septum. However, in approximately 25 percent of adults, the foramen ovale remains patent and acts as a potential right-to-left shunt [10].

The closure devices commonly used for percutaneous PFO repair include occluders made of two wire mesh discs filled with polyester fabric. The device is folded into a special delivery catheter, advanced into the heart and through the defect. When the catheter is in the proper position, the device slowly is pushed out of the catheter until the discs of the device sit on each side of the defect, like a sandwich. The two discs are linked together by a short connecting waist. Over time, heart tissue grows over the implant, and it becomes part of the heart.

Complications associated with trans-catheter closure of a PFO/ASD include device embolisation or malposition, arrhythmias (usually atrial but include sudden death), and device erosion/perforation [11].

Figure 78:
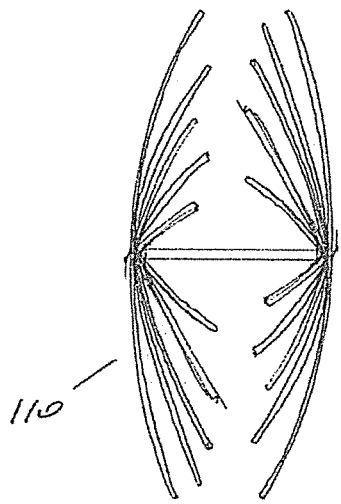
FIGS. 78 to 81 illustrate bristle devices for use in treatment of a septal defect.
Figure 79:
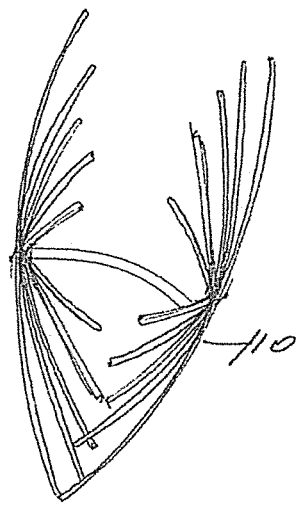

Referring to FIG. 78 a bristle device 110 suitable for occlusion septal defects of a patent foramen ovale is shown. The bristle device comprises at least two distinct device sections, which are connected via a core. Referring to FIG. 79, the device 110 is shown in a tilted configuration highlighting the flexibility of the device. This flexibility will enable the device to conform to the anatomy of the patient, and will ensure good trackability of the device during delivery. The bristle device 110 can be used for septal defect and PFO occlusion. FIGS. 78 and 79 show a septal defect or PFO device 110 which can articulate/bend depending on the target anatomy.

Figure 80:
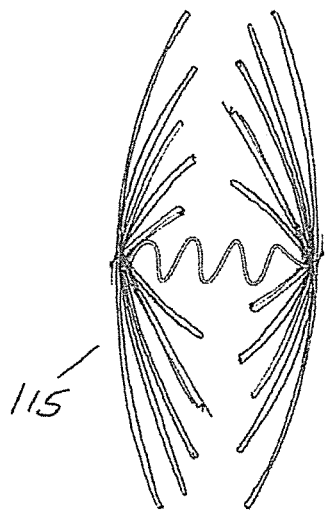
Figure 81:
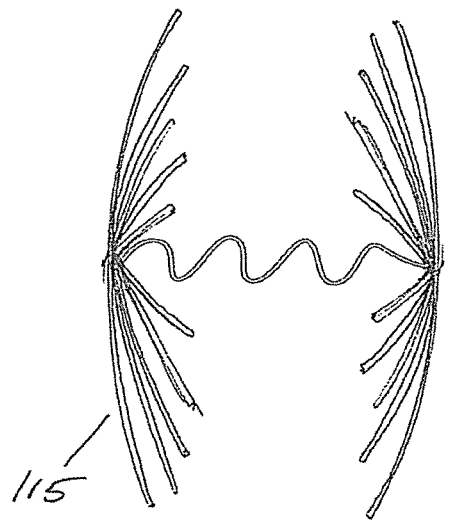

FIGS. 80 and 81 illustrate a septal occlusion device 115, which can stretch depending on the target anatomy (thickness of the septal wall).

Figure 82:
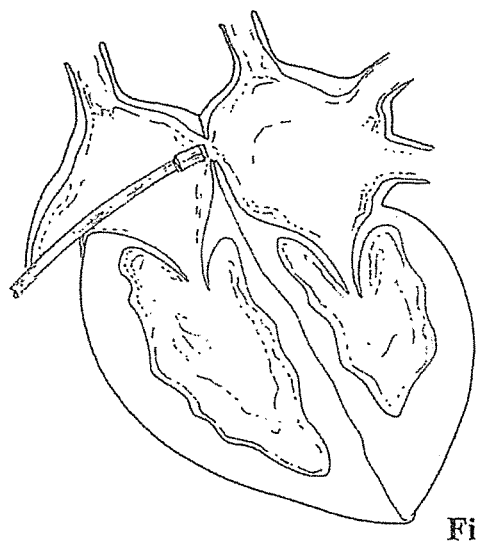
FIGS. 82 to 85 illustrate steps in deployment of the devices of FIGS. 78 to 81.
Figure 83:
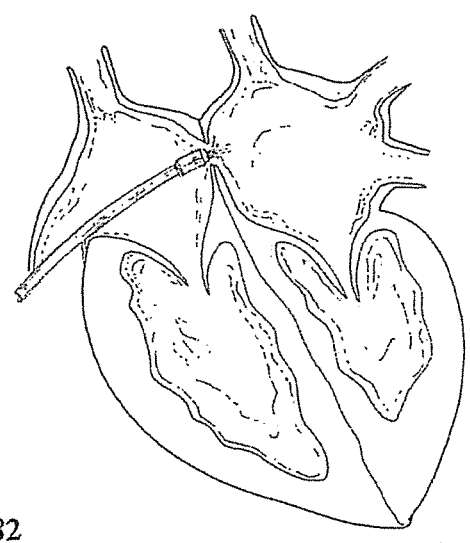
Figure 84:
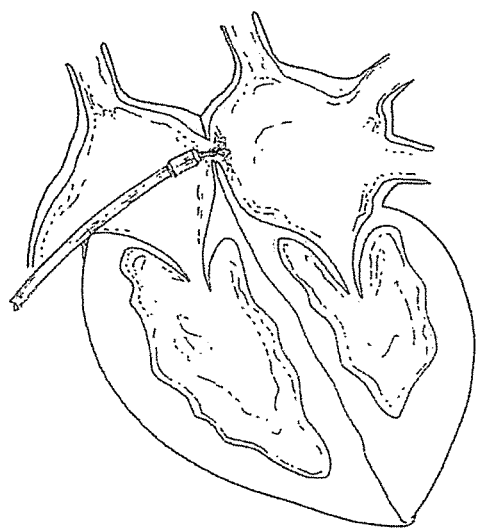
Figure 85:
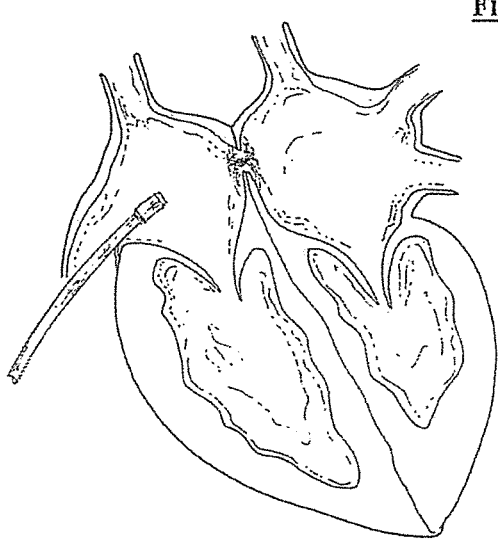

Referring to FIGS. 82 to 85 the implantation of the device 110 or 115 is illustrated. In FIG. 82 a catheter is shown advanced through the right atrium via the inferior vena cava. In FIG. 83 a segment of the device is shown partially deployed. This first segment will provide an anchor on the left atrium side of the patent foramen ovale. FIG. 84 illustrates one segment of the bristle device fully deployed within the left atrium. FIG. 85 illustrates the bristle device fully deployed.

Current technology foreshortens significantly upon deployment into a vessel, between 30-50%, this intended approach attempts to ensure that the pre-shaped coil snaps into its set shape when deployed into a vessel and adheres to the vessel wall [13].

With the exception of glue, which is occasionally used, there is no technology on the market today that does not use this approach.

Therefore it is difficult to embolise the entire length of a large vessel (>10 cm) with technology available today as complete vessel occlusion cannot be achieved and is cost prohibitive.

Additionally there is no product on the market today that can accommodate variable lengths peri-procedurally. This would be advantageous for three reasons:

Significantly reduce inventory requirements and range of products to be manufactured Allows the physician to precisely occlude the portion of the vessel that requires occlusion Allows a physician to occlude a bifurcation, feeder vessel or tributary that may contribute towards recanalization FIGS. 86 and 87 illustrate a bristle device 120 with length modifying components 121 that can be extended or retracted intraluminally to adjust the device to the requirements of the target vessel FIG. 88 illustrates deployment of a first bristle bundle into the lumen of the target vessel. Also illustrated is a technique of retracting delivery catheter to extend adjustable section between bristle bundles.

Figure 89:
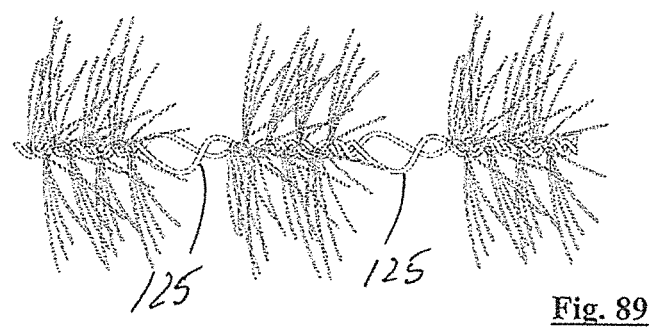
FIG. 89 shows a bristle device with a loosely wound core.
Figure 90:
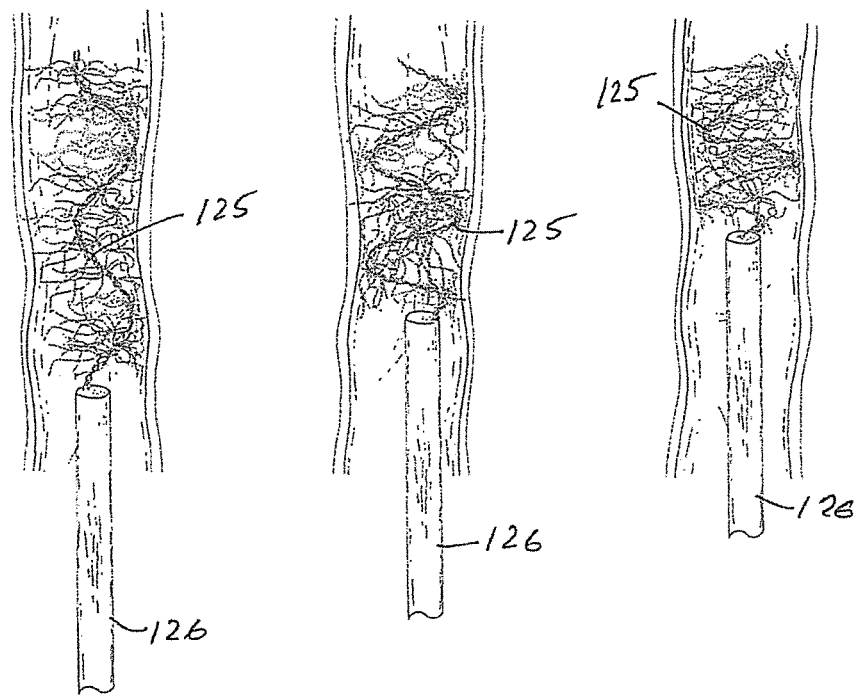
FIG. 90 shows techniques of pushing a delivery catheter to decrease adjustable sections between bristle segments.

FIG. 89 illustrates an alternative embodiment depicting a loosely wound core 125 that accommodates compression of bristle bundles intraluminally FIG. 90 illustrates technique of pushing a delivery catheter 126 forward to decrease adjustable sections between bristle bundles.

In order to induce stasis and cause thrombus formation, ideally no through flow path should exist in the prosthesis that permits blood to flow uninhibited from one end to the other. In reality, some flow path may exist which forces the blood to travel a tortuous path past the prosthesis bristles. If a low resistance flow path is present, occlusion may not occur.

For a bristle device, manufactured using a twisted wire approach, the bristles effectively define a helical surface. The negative of this helical surface defines a flow path.

By its nature, a bristle device may have a through flow path as shown in FIG. 91(a). This will cause turbulent flow and force the blood to interact with a greater surface area of the device, inducing thrombus formation and occlusion. A more tortuous path is shown in FIG. 91(b).

Figure 91:
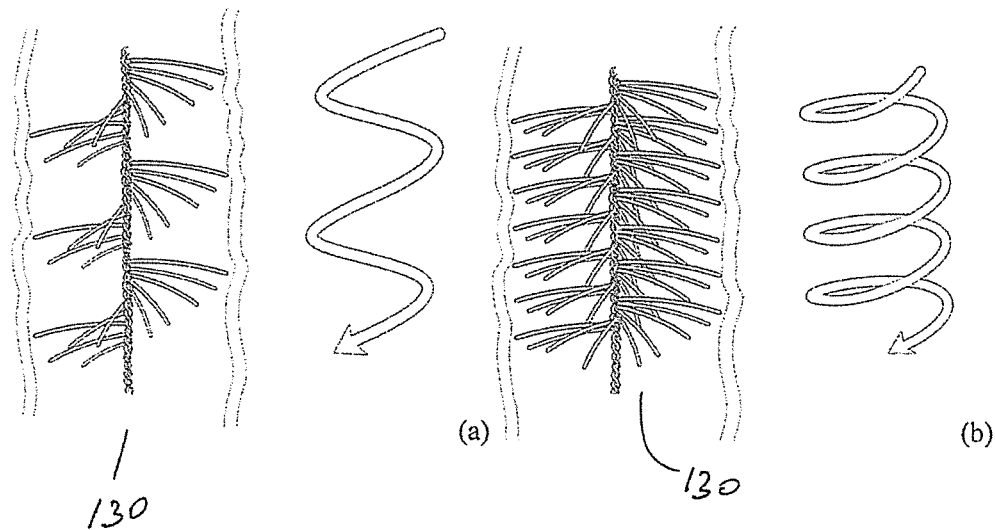
FIG. 91 illustrates bristle devices with a through flow path.
Figure 92:
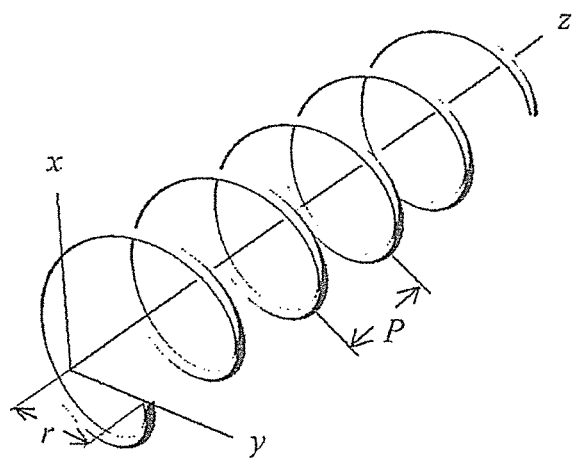
FIG. 92 depicts the flow path in a twisted bristle device.

FIG. 91 illustrates a bristle device 130 with a through flow path. Path is shown adjacent to the bristle device using the arrow. This path could be described as the inverse of volume of the device. This tortuosity of this flow path is defined by the pitch and radius of the helix, which defines the flow path as shown in FIG. 92.

A longer pitch, p, with a small radius, r, will mean a relatively easy and straight flow path. A short pitch with a large radius will imply a longer tortuous flow path. If a flow path does exist, this should be as tortuous and as long as possible to cause occlusion.

Preferably, for inducing occlusion of a blood vessel, the ratio of the pitch to the radius, p/r, of the flow path should be 50 or less. More preferably, the ratio of the pitch to the radius, p/r, of the flow path should be 10 or less. More preferably, the ratio of the pitch to the radius, p/r, of the flow path should be 1 or less. More preferably, the ratio of the pitch to the radius, p/r, of the flow path should be 0.5 or less.

Figure 93:
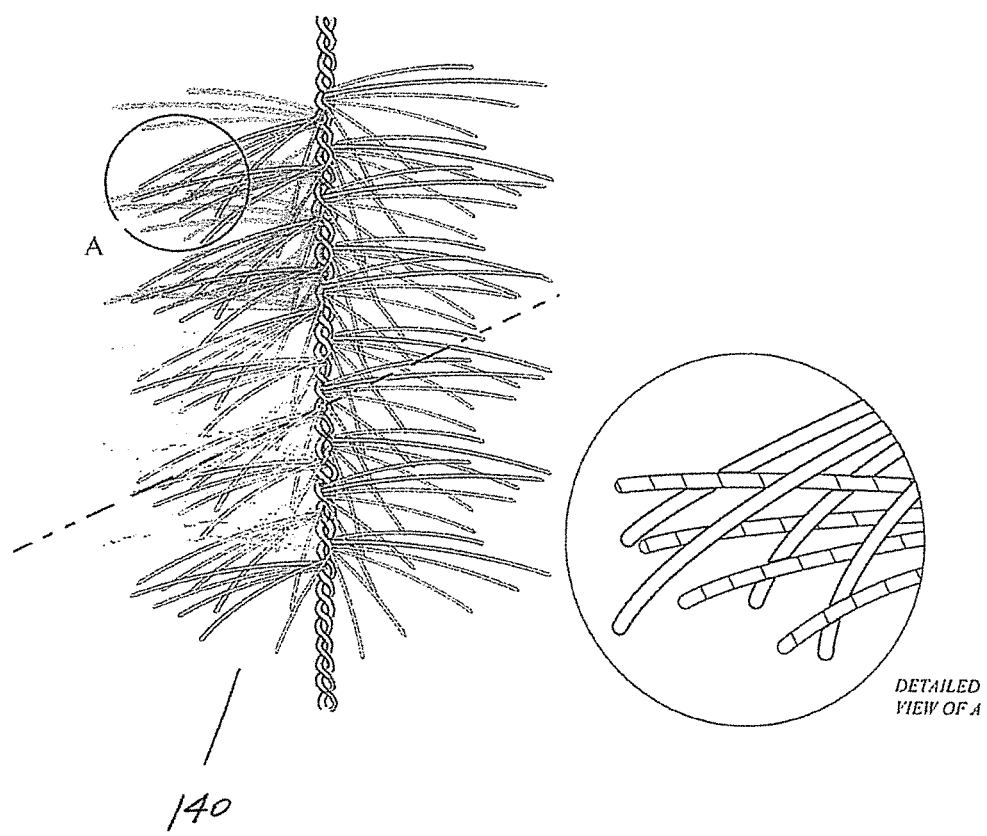
FIG. 93 illustrates overlapping bristle sections to inhibit flow.

If a twisted wire manufacturing approach is used, the ratio of the pitch to the radius of the helix should be such that the adjacent bristle sections of a bristle device 140 overlap as shown in FIG. 93.

FIG. 93 illustrates overlapping bristle sections to inhibit flow path through device.

Another means of ensuring overlapping bristles is to form the device using pre-shaped bristles e.g. saw tooth or spiral, which would increase interaction between bristles.

Figure 94:
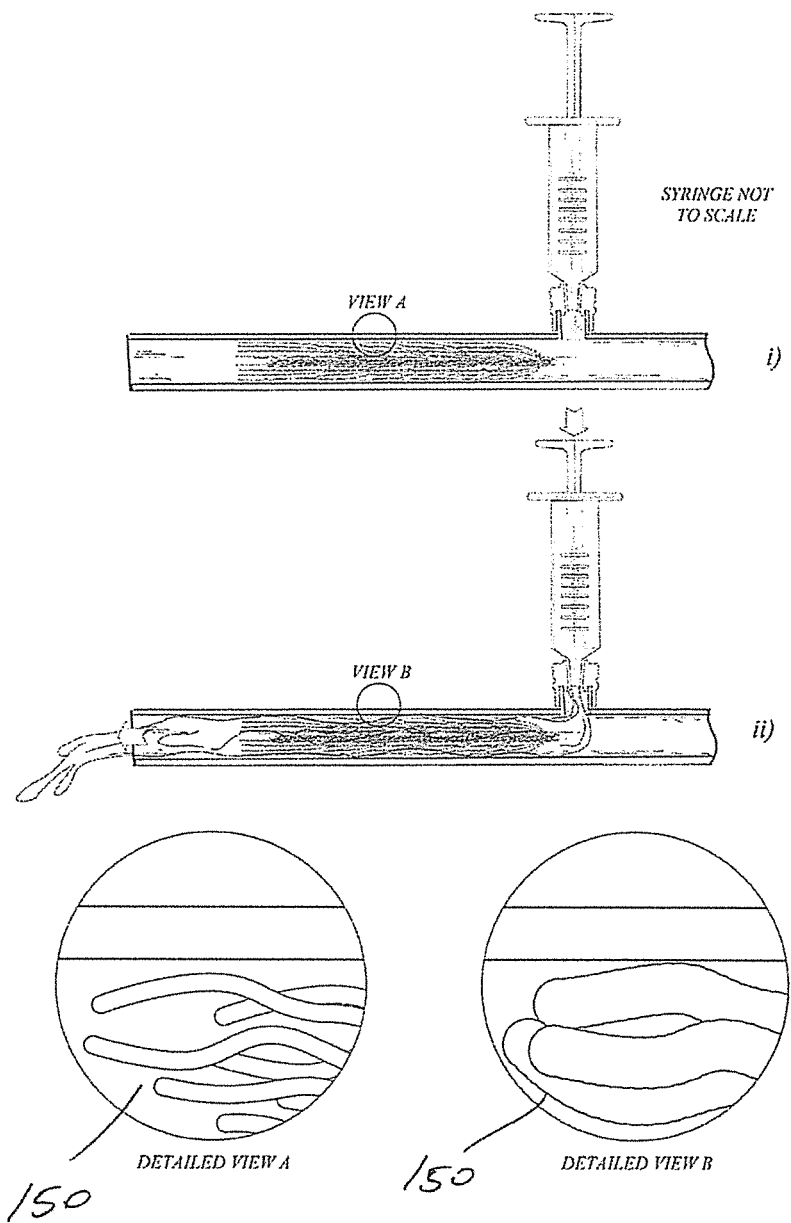
FIG. 94 shows another bristle device with fibres that increase in volume.

In FIG. 94 a bristle device is shown in which, upon coming in contact with a fluid or blood, the fibres 150 swell up increasing in volume in order to further occlude the lumen in which they reside. This process could be initiated before deployment in the body, or while the bristle device is in its collapsed condition in a catheter/loading tube, as shown in FIG. 94. Similarly, the fibres could be intended to absorb a drug when increasing in volume. This drug would then be delivered to the vessel wall once the bristle device is deployed. FIG. 94 illustrates fibres that increase in volume when in contact with a fluid and or the blood.

Figure 95:
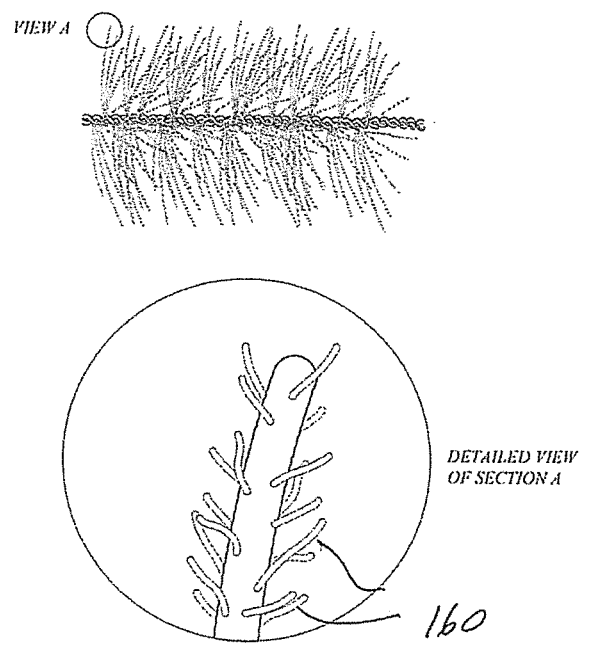
FIG. 95 illustrates a bristle device with microfibers for improved thromogenicity.

In another embodiment, the bristles could have micro fibres 160 in order to increase thrombogenicity and reduce flow path. This is shown schematically in FIG. 95.

Due to adjacent vessel blood flow, an embolus could break away from the clot within the bristle device. The maximum potential size of an embolus which could break away from the bristle device is dictated by the density of the bristles in the device, i.e. the cavities within which thrombus can form in the device. This is defined by the distance between adjacent bristles. Similarly, the ability of the bristle device to cause vessel occlusion can be improved by reducing the distance between adjacent bristles.

Pulmonary Embolism

A common vessel for embolisation is the gonadal vein (for the treatment of varicocele, pelvic vein competence). An embolus could detach from a bristle device, which has been deployed in the proximal portion of a gonadal vein close to the renal vein. This embolus can then travel via the left common iliac vein through the inferior vena cava into the right atrium of the heart. This could potentially travel into the pulmonary arteries causing a pulmonary embolism. In about 5% of people in whom autopsy is done to elucidate the cause of death, pulmonary embolism is unexpectedly found to be the cause. Gardner suggests that the clot size should be limited to 4.5 mm or less using clips in order to prevent a lethal pulmonary embolism [19].

Peripheral Arterial

Figure 96:
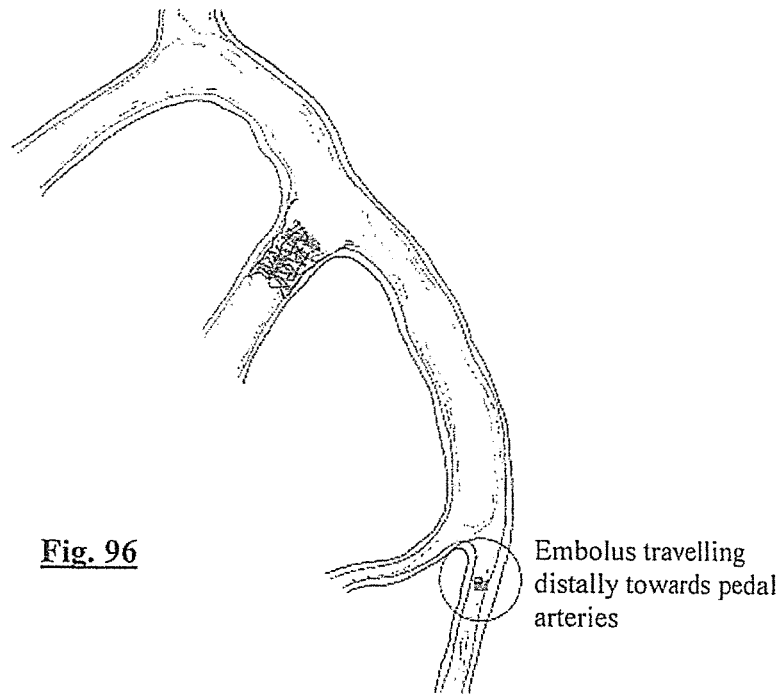
FIG. 96 shows an embolus detaching from a bristle device.
Figure 101:
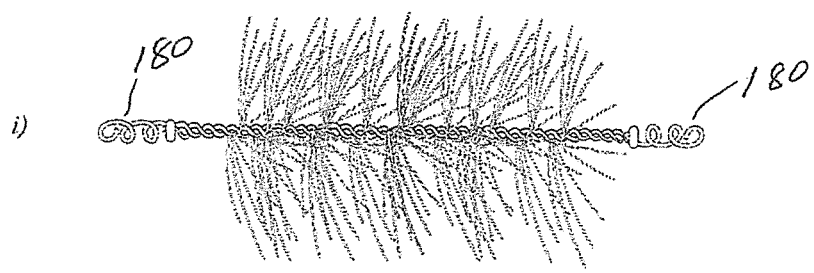
FIGS. 101 to 104 show various bristle tips to prevent vessel perforation upon or after deployment.
Figure 102:
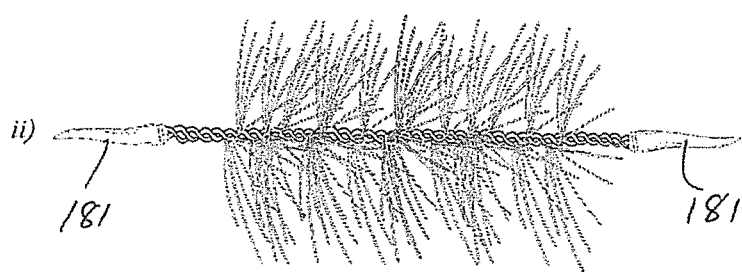
Figure 103:
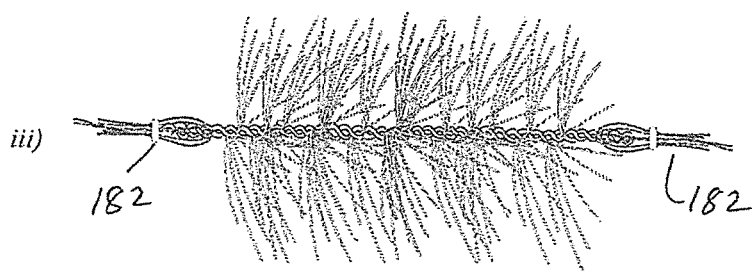

Ideally any embolus which could break away from the embolisation device is small enough so that it can be thrombolyzed by the body's own defences and remain clinically asymptomatic. A large embolus could cause tissue ischemia and infarction. In 1989, Kazmier proposed a classification for disseminated peripheral atheroembolisation into three major clinical presentations: peripheral syndrome, renal syndrome, and visceral syndrome [20]. By definition, microemboli represent atheromatous material with a size less than 1 mm. Accordingly the maximum size embolus which can be permitted to break away from the occlusion device should be less than or equal to 1 mm. To ensure this, the maximum dimension between adjacent bristles which define the cavity from which an embolus could break away should be 1 mm or less. An embolus from a bristle device deployed in the internal iliac artery could enter the common iliac and travel distally to the smaller lumens such as the popliteal and tibial or pedal arteries (shown in FIG. 64). A blockage of these lumens can cause ischemia of the foot, a phenomenon known as trash foot. FIG. 96 shows an embolus detaching from a bristle device which has been deployed in the left internal iliac artery.

Cerebral

The effect of an embolus may not be confined to the peripheral circulation. In the case of the cerebral lumens, an embolus of 1 mm or less may not be tolerated, as emboli of this size can cause a stroke. For aneurysm treatment, the maximum acceptable diameter should be lower than 1 mm. For the case of embolic filters, used to capture emboli which occur during carotid stenting, the pore sizes are approximately 0.8 mm in diameter [21]. Accordingly the gap between the bristles in the deployed configuration should be 0.8 mm or less. FIG. 97—shows a bristle device deployed to treat a cerebral aneurysm. An embolus has broken away from the bristle device which could cause stroke.

In the invention, and referring to FIGS. 98 to 100 to prevent pulmonary embolism a bristle device 170, 171, 172 has gaps between adjacent bristles to limit clot fragments to 4.5 mm or less. To prevent potential for peripheral microembolism the bristle device should have gaps between adjacent bristles of 1 mm or less. For the prevention of cerebral infarction events, the bristle device should have gaps between adjacent bristles of 0.8 mm or less.

FIGS. 98 to 100 illustrate gaps between bristles dictate the potential emboli which could detach form the bristle device. A=4.5 mm, B=1.0 mm, C=0.8 mm.

Figure 104:
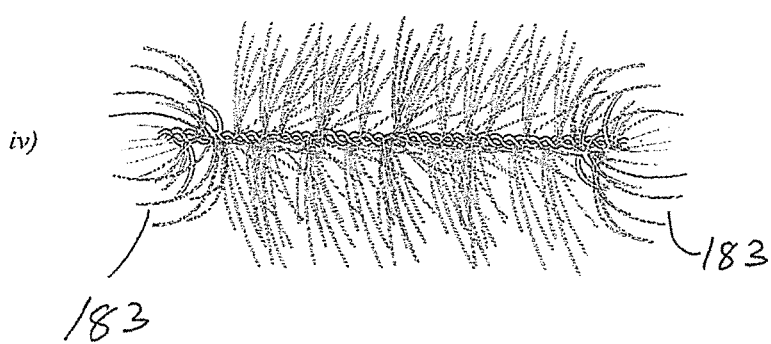

Ideally medical devices that come in contact with a vascular wall or are deployed endovascularly require features that ensure they do not perforate or puncture the vessel wall. Perforations can lead to hematoma and other serious adverse events. It is critical for devices to reduce the risk of internal wall damage. This also provides the clinician with confidence to advance the device against resistance, knowing that the device will not induce trauma. FIGS. 101 to 104 show various bristle tips to prevent vessel perforation upon or after deployment. (i) soft spring 180 (FIG. 101), (ii) soft flexible tips (e.g. made from a polymer) 181 (FIG. 102), (iii) bristles at end of bristle device tied to make an atraumatic end 182 (FIG. 103), (iv) bristles 183 naturally protrude from the end of the device (FIG. 104).

FIGS. 101 to 104 illustrate various embodiments of atraumatic distal and proximal ends designed to prevent vessel wall perforation During percutaneous endovascular treatment an embolisation coil is typically delivered to a desired location in the vasculature of a patient through the use of a catheterization procedure. In this procedure, a catheter is inserted into the vasculature of a patient and positioned to be proximal or distal to the targeted anatomical location. Generally, an embolisation coil is loaded into the lumen of the catheter and advanced through the catheter using a pusher rod until it reaches and exits through the distal end of the catheter.

Unless "detachable" coils are used this device cannot be repositioned or retrieved once deployed. This technique suffers from difficulty associated with the precise and controlled placement of the embolisation coil. Accordingly, there exists a need to develop and provide a system or mechanism for the placement of an embolisation coil into the vasculature of a patient that can be done in a precise and controlled manner, while maintaining cost effectiveness, simplicity, reliability, and manufacturability.

Figure 105:
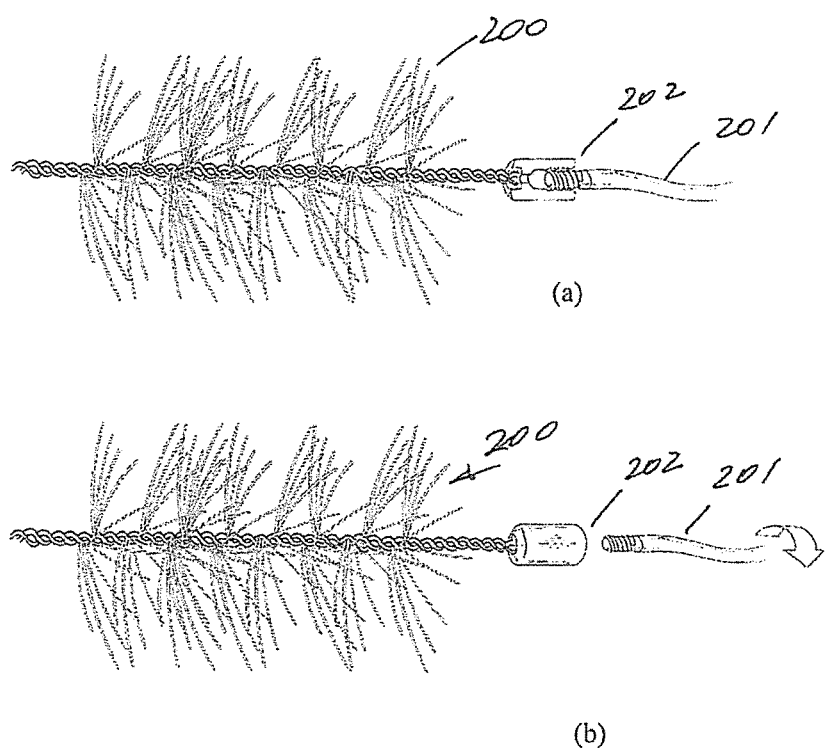
FIG. 105 illustrates the assembly of a bristle device to a delivery wire.

FIG. 105 (*a*) shows an assembly wherein the bristle device 200 is attached to a delivery wire 201 via a screw mechanism 202. In this assembly detachment is accomplished by unscrewing the delivery wire from the bristle device as shown in FIG. 105 (*b*).

The interaction of the device, which is constrained radially at least to some extent within the lumen, causes an interference fit. This interference fit occurs due to the propensity of the lumen to try alter (reduce) the diameter of the bristle device, and the propensity of the bristle device to try to alter (increase) the lumen diameter.

The classic relation describing the holding torque of an interference fit assembly using that the assumption that the surfaces have no irregularities and that the contact pressure at the interface is uniformly is distributed, is as follows (Mascle et al., 2011):

$T_{holding} \alpha \mu_s d_{sh} p A$

This implies that the holding torque, $T_{holding}$, or torque required to cause a rotation of the bristle device within the lumen is proportional to the coefficient of static friction between the bristle device and the lumen wall, $\mu_s$, the diameter of the lumen, the interference pressure, p, and the area of contact, A.

This implies that interference pressure is a function of the outward radial force of the device against the pressure. The coefficient of static friction between the bristle device and the lumen wall is a function of the lumen and bristle device materials, their roughness and the topography of the geometry which results when the bristle device is deployed within the lumen.

In order to allow detachment of the bristle device from the delivery wire once it has been deployed in the lumen, the torque to unscrew the delivery wire from the bristle device must not exceed the holding torque of the bristle device in the lumen, i.e. $T_{holding} > T_{unscrew}$. If the holding torque does not exceed the torque required to unscrew the delivery wire from the bristle device, the bristle device will simply rotate within the lumen and detachment may not occur.

Figure 106:
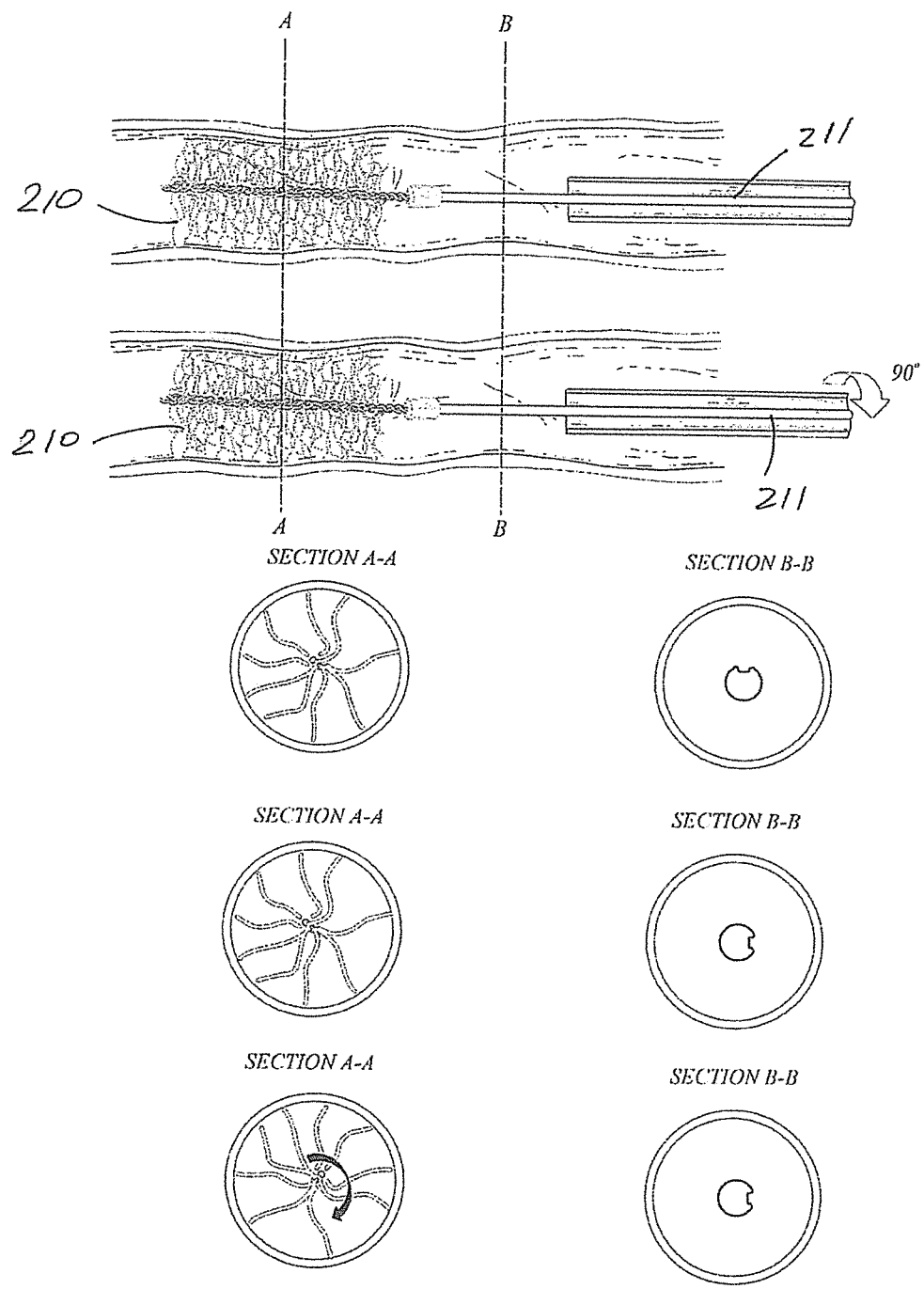
FIG. 106 illustrates a bristle device deployed in a lumen.

FIG. 106 shows a bristle device 210 deployed in a lumen. Section A represents a cross section within the bristle device. Section B represents a cross section at the level of the delivery wire proximal to the detachment mechanisms.

In FIG. 106 (b), the behaviour of the bristle device 210 is shown when no twist is applied to a delivery wire 211 (top). The middle schematic shows the behaviour when some twist is applied to the delivery wire 211 causing the bristle device 210 to rotate within the lumen (undesirable). This occurs because the holding torque of the bristle device does not exceed the torque required to unscrew the bristle device from the delivery wire. In the bottom schematic upon rotation of the delivery wire, no rotation of the device occurs since the holding torque of the bristle device exceeds the torque required.

When coils migrate to unintended locations, they are required to be removed to prevent non-target embolisation, tissue ischemia and/or erosion. In general removal of coils is attempted via a percutaneous endovascular approach, by placing a guiding catheter close to the migrated coils and extracted by using a forceps or gooseneck snare to grasp the coil. Technically, removal of coils is very challenging and can take dozens of attempts with various devices to remove [22]. Complications of coil retrieval are significant and can involve [8]:

Disturbing the rest of the coil nest and exacerbating the problem.

Damaging other vessels: dissection, occlusion, spasm, rupture of the vessel caused by manipulation of the retrieval device.

Cardiac arrhythmias if the coil has migrated to the heart.

Embedding or further distal embolisation of the coil or device

In the invention we provide a bristle device in which the diameter (size) of the core is greater than that of the core of the bristle device. This enables the bristle device to be retrieved easily using a gooseneck or snare type device.

Figure 107:
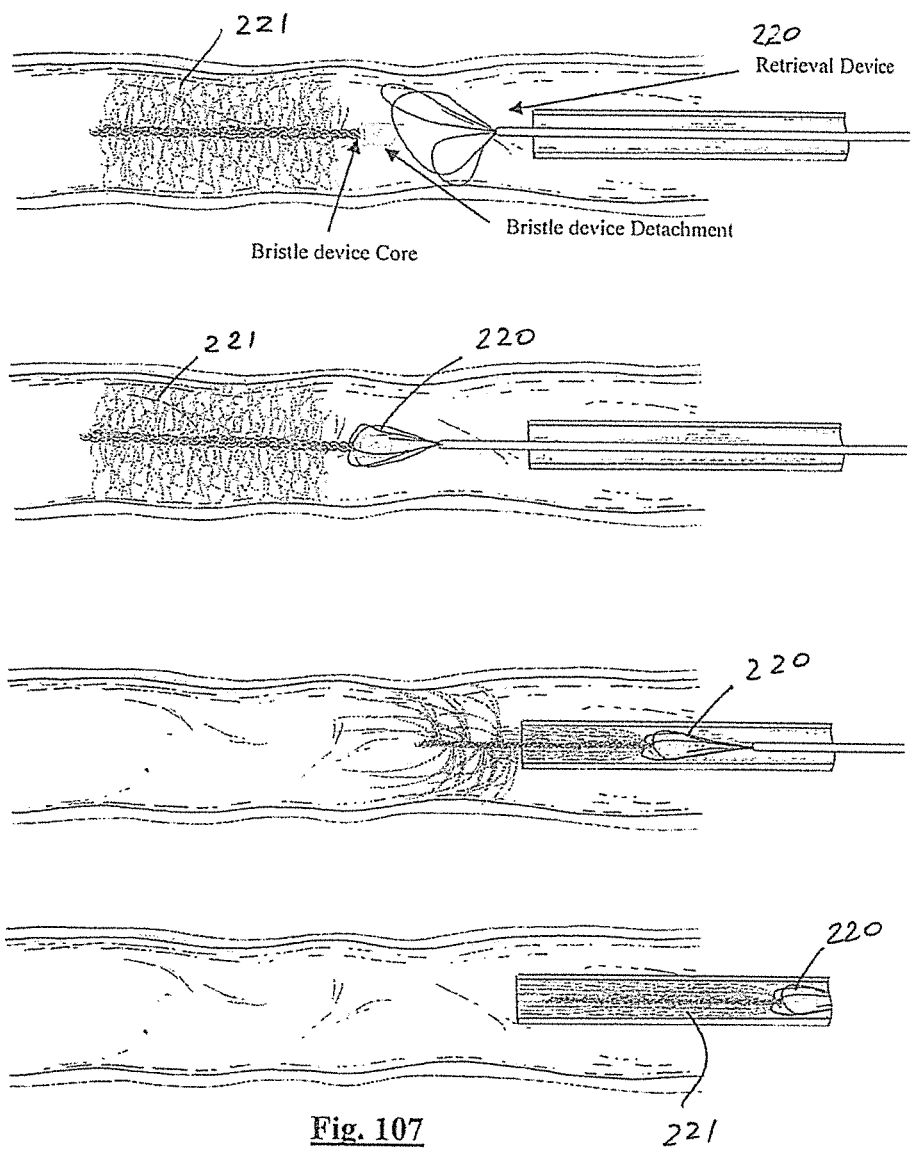
FIGS. 107 to 109 show various retrieval systems for retrieving a bristle device.

FIG. 107 shows how a retrieval device 220 can easily grasp a bristle device 221 at the screw detachment mechanism. In the top schematic the retrieval device has been deployed from its delivery catheter. In the middle schematic the bristle device detachment mechanism has been grasped in the wire "snare" of the retrieval device and is being retracted into the catheter. The bottom schematic shows the final retraction of the bristle device, now almost entirely in a collapsed condition, into the catheter.

Figure 108:
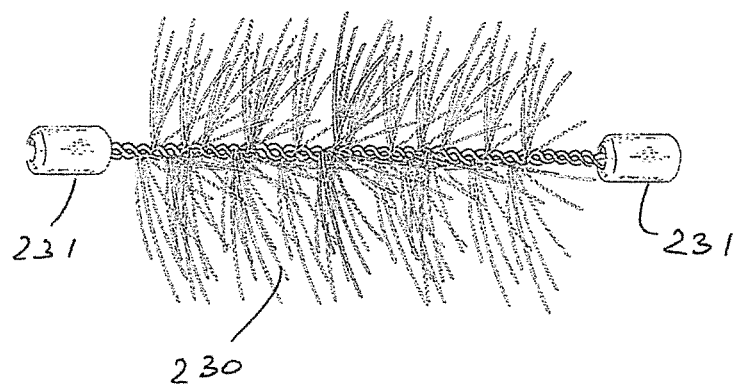

FIG. 108 shows a bristle device 230 with a screw detachment mechanism 231 at both ends. This can be retrieved from a distal or proximal approach.

Figure 109:
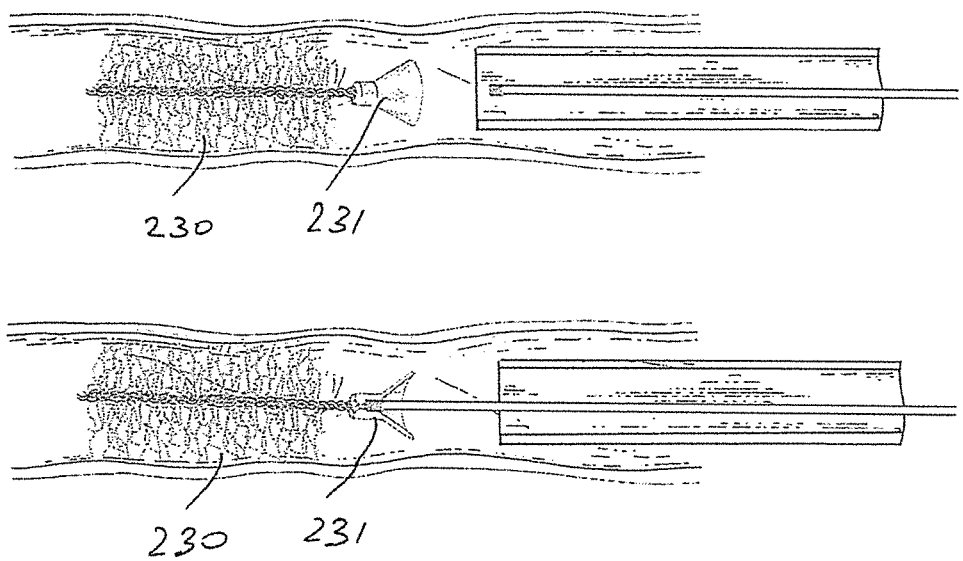

Migrated coils are generally retrieved using a forceps or a gooseneck snares. These are expensive devices and can significantly add to the procedural cost. Ii would be advantageous if a coil could be grasped and removed without the necessity to use additional retrieval devices. In the embodiment shown in FIG. 109, the screw detachment mechanism is shaped to guide the delivery wire into the thread to be screwed to the wire and retrieved.

In some cases, it is unnecessary or undesirable to permanently occlude a blood vessel. In these circumstances, using an agent which causes temporary vascular occlusion may be preferable.

Circumstances in which temporary agents may be indicated [8]:

Pre-operative embolisation: e.g., embolisation of a renal tumor immediately before resection. In these circumstances, there is no advantage in permanent obliteration of the tumor circulation and any non-target embolisation is less likely to be harmful.

Trauma: it is usually only necessary to arrest bleeding until a stable clot forms and the vessel can heal.

Upper gastrointestinal tract hemorrhage.

Temporary embolisation agents are most beneficial when a vessel can safely be sacrificed but permanent occlusion is not necessary (e.g., internal bleeding associated with trauma). Having a biodegradable embolisation device that provide temporary embolisation, relieves the clinical issue, and then safely degrades over a specific time period providing the opportunity for systemic blood flow to be restored would be a significant clinical advancement.

In other circumstances, it may be preferable that once embolisation has occurred, that the device, or a portion of the device, biodegrades meaning that the implant:

1. Has no structural role integrity, and therefore does not interfere with surrounding tissues 2. Is no longer present in the body In the invention, either the core, or the bristles, or both the bristles and the core could be biodegradable or absorbable.

The biodegradable/absorbable elements of the device may be composed of synthetic polymers (Poly-lactic acid (PLA) and its isomers and copolymers, Poly-glycolic acid [PGA], Poly-caprolactone [PCL], Poly dioxanone, Poly-lactide-co-glycolide) or Magnesium alloys. This is shown in FIGS. 110 to 112.

Figure 110:
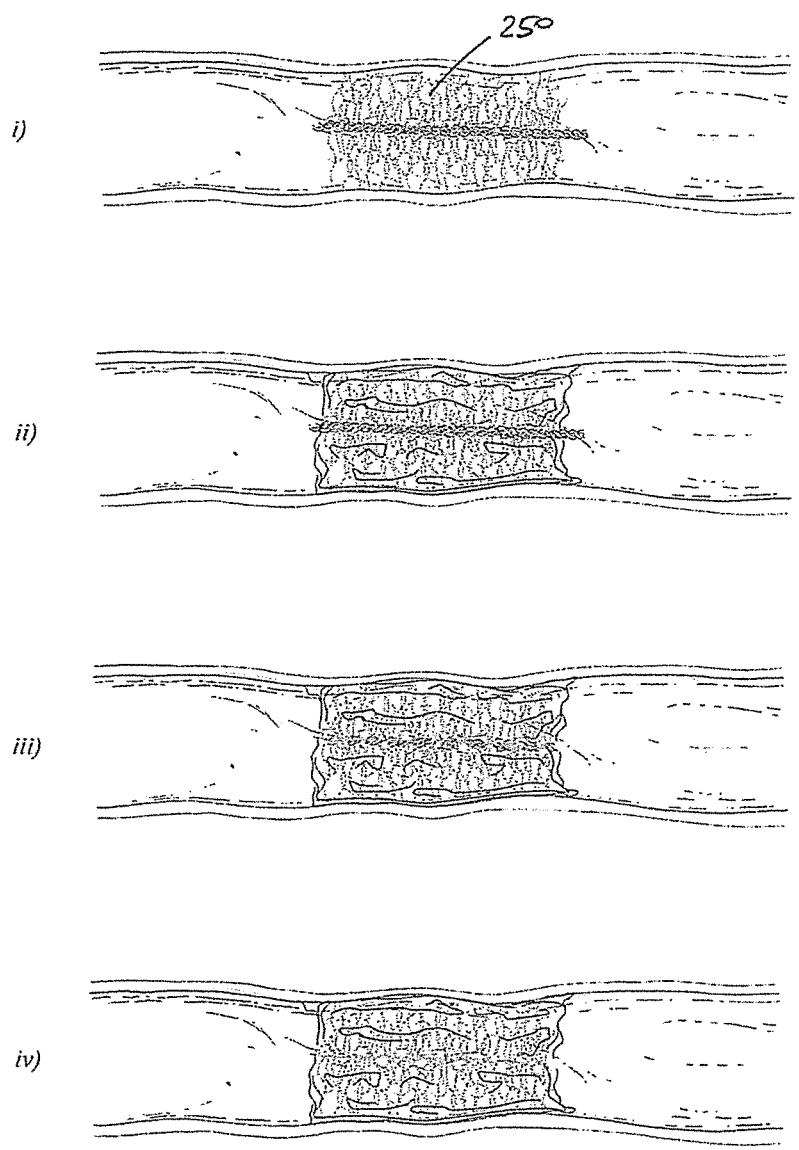
FIGS. 110 to 112 illustrates various degradable bristle devices.
Figure 111:
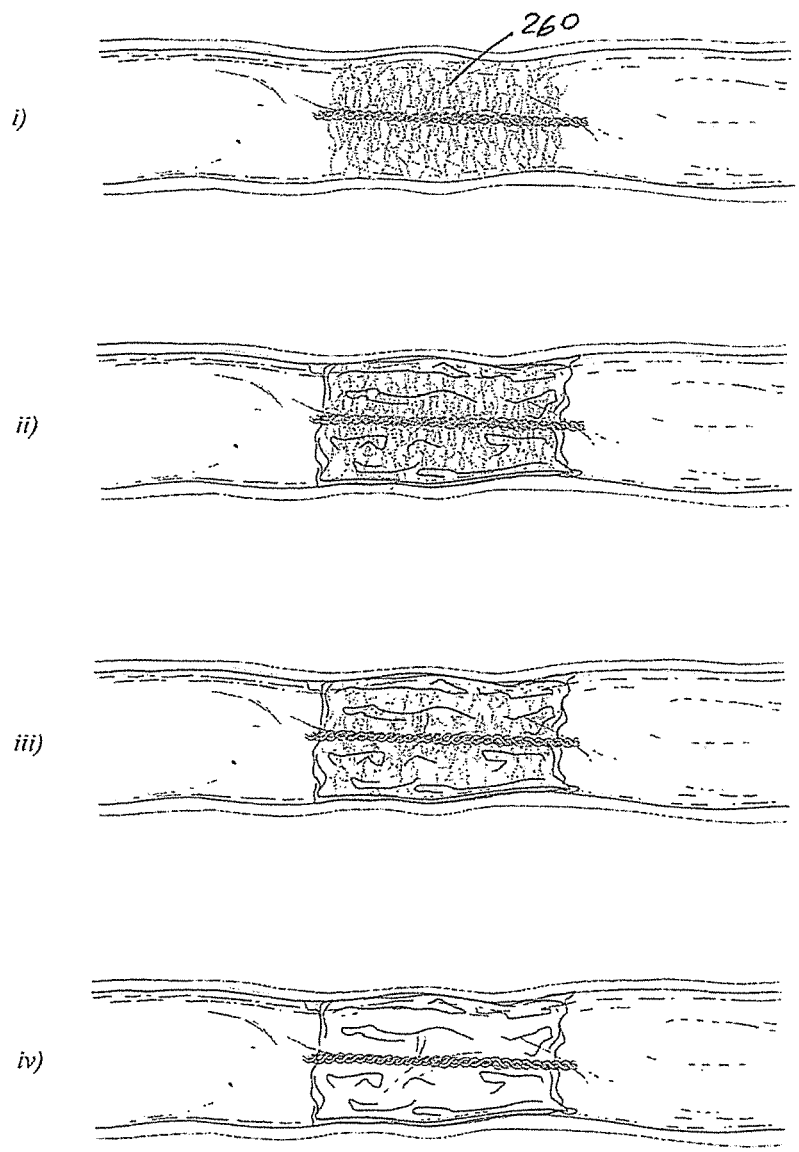
Figure 112:
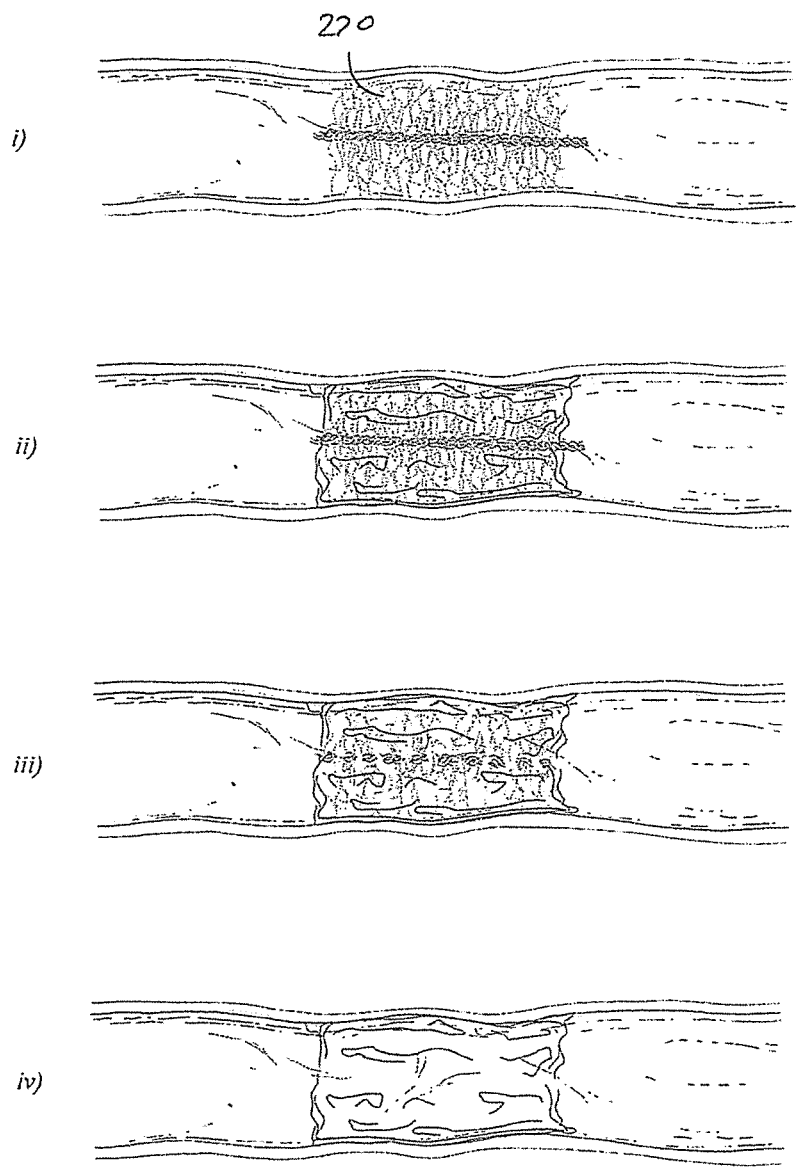

FIG. 110 (i) a bristle device 250 on implantation, (ii) thrombus formed in the bristle device, (iii) core begins to degrade, (iv) core fully degraded leaving only thrombus interspersed with bristles supporting the thrombus FIG. 111 (i) a bristle device 260 on implantation, (ii) thrombus formed in the bristle device, (ii bristles begins to degrade, (iv) bristles fully degraded leaving only thrombus a supporting core FIG. 112 (i) a bristle device 270 on implantation, (ii) thrombus formed in the bristle device, (iii) core and bristles begin to degrade, (iv) bristle device fully degraded leaving only thrombus within the vessel A number of methods of manufacture may be used to make the prosthesis. FIG. 113 shows a twisted wire device 280 manufactured using a twisted wire method. The fibres are placed between two parallel wires. These wires are fixed at one end and twisted at the other. Upon twisting the wires are formed into a helix causing the bristles to translate from being parallel to being rotationally offset from one another forming a device like construct.

In another embodiment variations in the bristle density can be achieved by varying the pitch of the twisted wire which the holds the bristles in place. This is shown schematically in FIG. 114. FIG. 114 illustrates a twisted wire device with varying core wire pitch in order to vary the density of the bristles.

Figure 115:
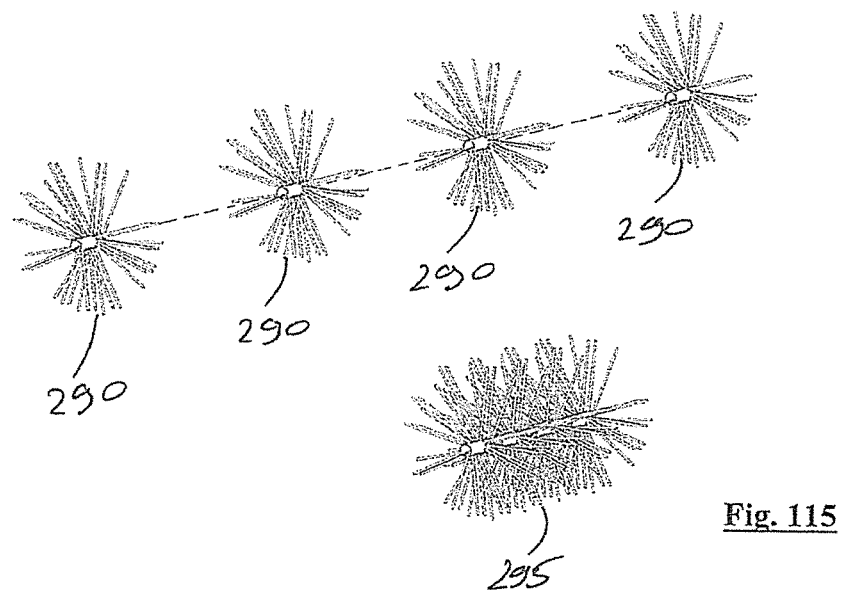
FIG. 115 illustrates manufacture of a bristle device from a number of segments.

FIG. 115 shows a series of individual segments which in this case are extrusions 290, each of which has an array of long elements projecting from the centre. Upon connection of these constructs, a prosthesis 295 suitable for lumen occlusion can be constructed. FIG. 115 illustrates manufacture from a series of device segments, or extrusions.

Figure 116:
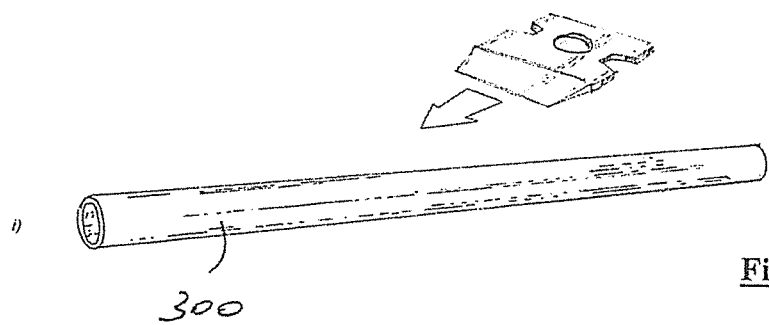
FIGS. 116 and 117 show another method of manufacture.
Figure 117:
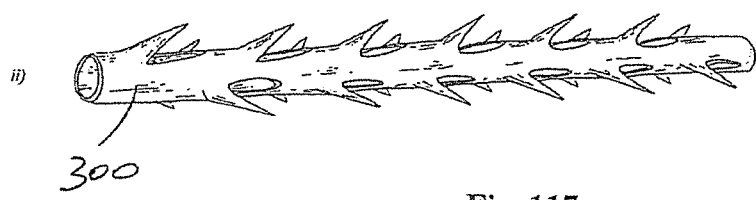

FIGS. 116 and 117 illustrates a method of manufacture in which the entire device is one piece is by cutting the fibres from a core 300. This could also be constructed by laser cutting the tube and passing and expanding element through the lumen to splay out the fibres.

A bristle device may also be used as a platform for therapeutic delivery. This could be an agent to augment thrombogenicity (sclerosant, fibrin, thrombin, glue, alcohol), or to delivery an oncologic drug to treat a tumour, or a device to aid in radiofrequency ablation. This is shown schematically in FIG. 118. The elution time of such an agent could be seconds, hours, days, or years. The coating could be fluid or solid.

Figure 118:
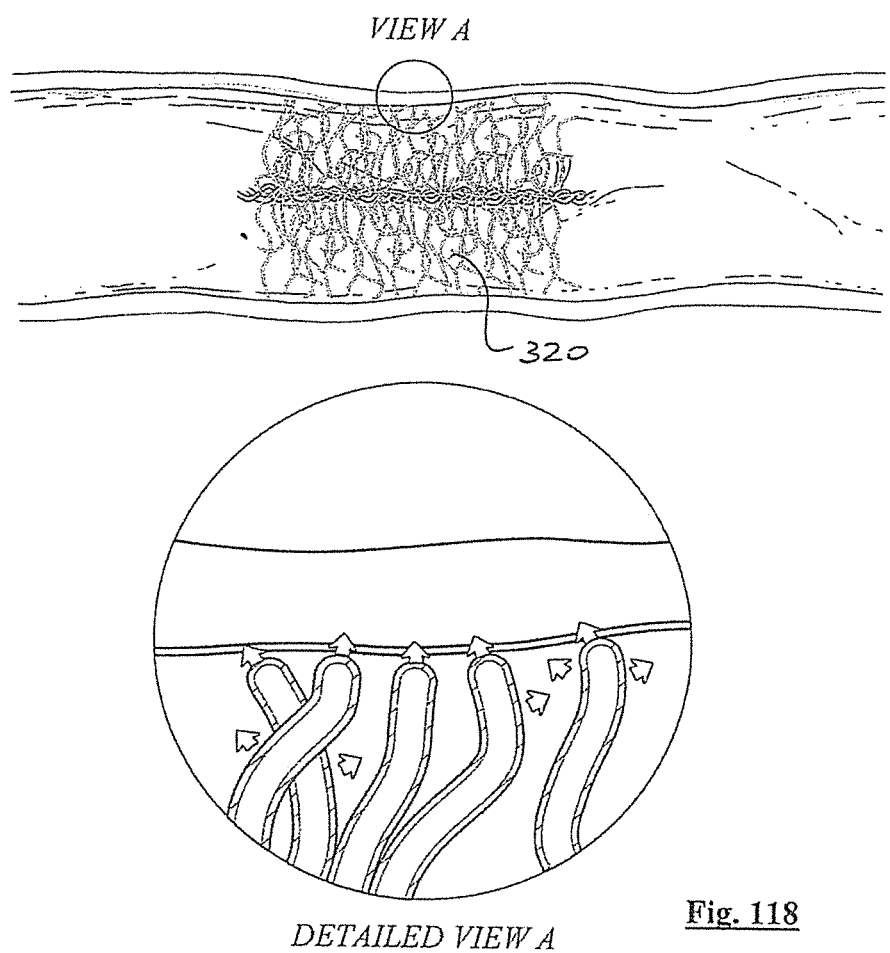
Figure 119:
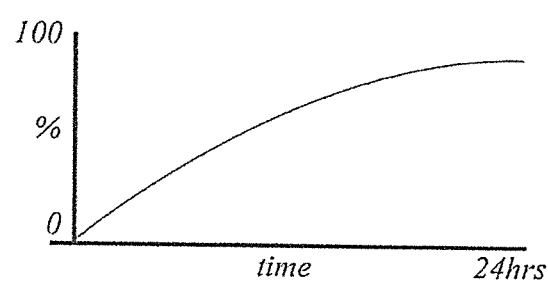

FIGS. 118-119 illustrate delivery of the drug to the vessel wall once a bristle device 320 is in place.

Figure 120:
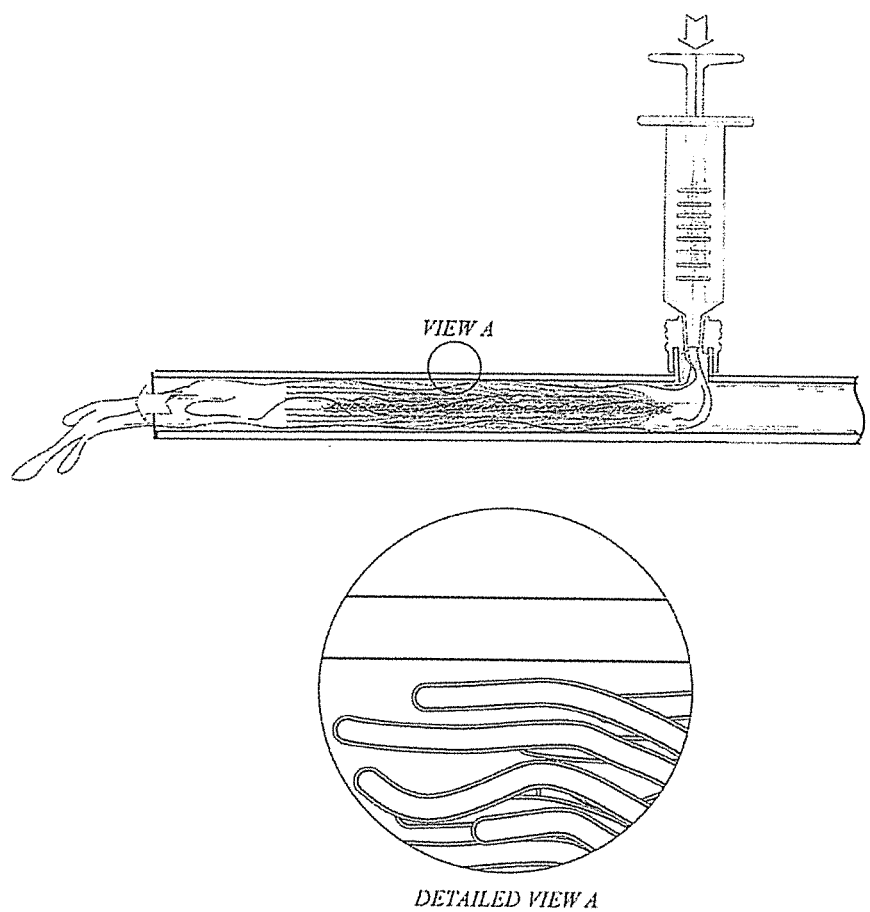

In one embodiment, the device is coated with a drug, or sclerosant, just before being pushed into the catheter (FIG. 120). This drug or sclerosant is then delivered to the vessel wall once it is deployed at the target site. This is shown schematically in FIG. 120. FIG. 120 illustrates flushing of bristle device with a therapeutic prior to being pushed to target vessel. The detailed view shows a coating of the drug on the device fibres following flushing.

The bristles of the bristle device could be further enhanced using striations or holes which can contain a therapeutic. This could increase the volume of therapeutic on the bristle, and to further control its elution over time by restricting the area from which the therapeutic can dissolve, elute.

FIGS. 121 to 123 illustrate bristles that are enhanced using pores, striations or holes to hold drug for elution over time.

The invention also provides a "perfusion bristle device". This bristle device 350 contains a channel 351 through the centre for flow. As the flow passes the bristles the therapeutic is transferred to the flow, allowing a distal therapy to be delivered. FIG. 124 illustrates the use of a perfusion bristle device for delivery of a drug.

To enable the physician to deliver the bristle device through tortuous anatomy it must be flexible. This also enables the bristle device to conform to tortuous anatomy once implanted. The flexibility of the prosthesis is defined, primarily, by properties of the core to which the bristles are attached. The flexibility of the core is a function not only of the amount of material in the core, but also its distribution, and material (lower modulus means greater flexibility).

There are certain clinical indications where the optimal clinical outcome would be to simultaneously embolise a vessel and an adjoining, diverging division.

Such a clinical situation is the prophylactic embolisation to prevent type II endoleak pre-endovascular aneurysm repair (EVAR). Type II endoleaks can be identified during angiography by the presence of contrast travelling from a peripherally catheterized vessel into the excluded aneurysm sac. The objective when embolising pre-EVAR is permanent occlusion of the internal iliac artery proximal to its bifurcation to ensure that there is complete occlusion before proceeding to EVAR, as any leak will cause reoccurrence of the issue. Using an angled, adjacent vessel to anchor a portion of the device while deploying the majority of the same device in the larger vessel would provide an anchor for the device, preventing future migration.

Additionally, the internal iliac vein bifurcates into anterior and posterior divisions, which supply pelvic organs as well as the gluteal muscles. It is frequently necessary to embolise one of the anterior or posterior divisions as well as the internal iliac vein. The same approach as described previously would be advantageous; embolising the adjacent tributary while retracting the remainder of the device to occlude the higher order vessel.

A bristle device, which has the flexibility to be deployed across bifurcating vessels, may be preferable in these instances.

FIG. 67 illustrates two device prostheses of the same length with different core wire diameters, $\varnothing_1$ and $\varnothing_2$, where $\varnothing_1 > \varnothing_2$. Note: it is assumed that the core is approximately of circular cross section. One end of the prostheses is fixed and a load, P, is applied to the opposite end causing deflection of the prosthesis. The deflection of the larger diameter device, U1, is much smaller than that of the lower diameter device (U2).

Considering a bristle device with a stainless steel core constructed from twisted wire, its diameter should preferably be constructed from twisted wires of diameter 0.02 inches or less. Otherwise it may not be possible to track the device to the target vessel for deployment.

In other embodiments, the flexibility of the device could be improved by having flexible sections 95 between device sections 96 as shown in FIG. 68. Bending within the device is taken up, primarily, by the flexible sections, which can articulate to enable it to pass through a catheter placed in tortuous anatomy, or to be deployed in a curved vessel, or across a bifurcation. In this case the bristle device has flexible sections for articulation.

Because the device is flexible it will not perforate a vessel or cause injury to the patient. A device which is not flexible may cause injury during deployment.

Furthermore, physicians may wish to place a portion of the device in a main vessel, and another portion of the device in a branch as illustrated in FIG. 68. Depending on the angle between the main vessel and the branch of the vessel, the implant is sufficiently flexible to accommodate the anatomy at the location in which it is deployed.

Many vessels in the body undergo significant deflections during normal movement such as when walking or sitting. The embolisation device of the invention has sufficient flexibility and durability such that it will not fracture, or perforate the vessel or neighbouring anatomy during such movements.

The embolisation device may be constructed such that it is extremely flexible. One way to achieve this is by connecting segments of brushes to one another via more flexible sections such as illustrated in FIG. 68. The flexible sections may be introduced as unique parts, or by connecting the segments with connections that provide articulation and/or regions to accommodate bending.

Figure 127:
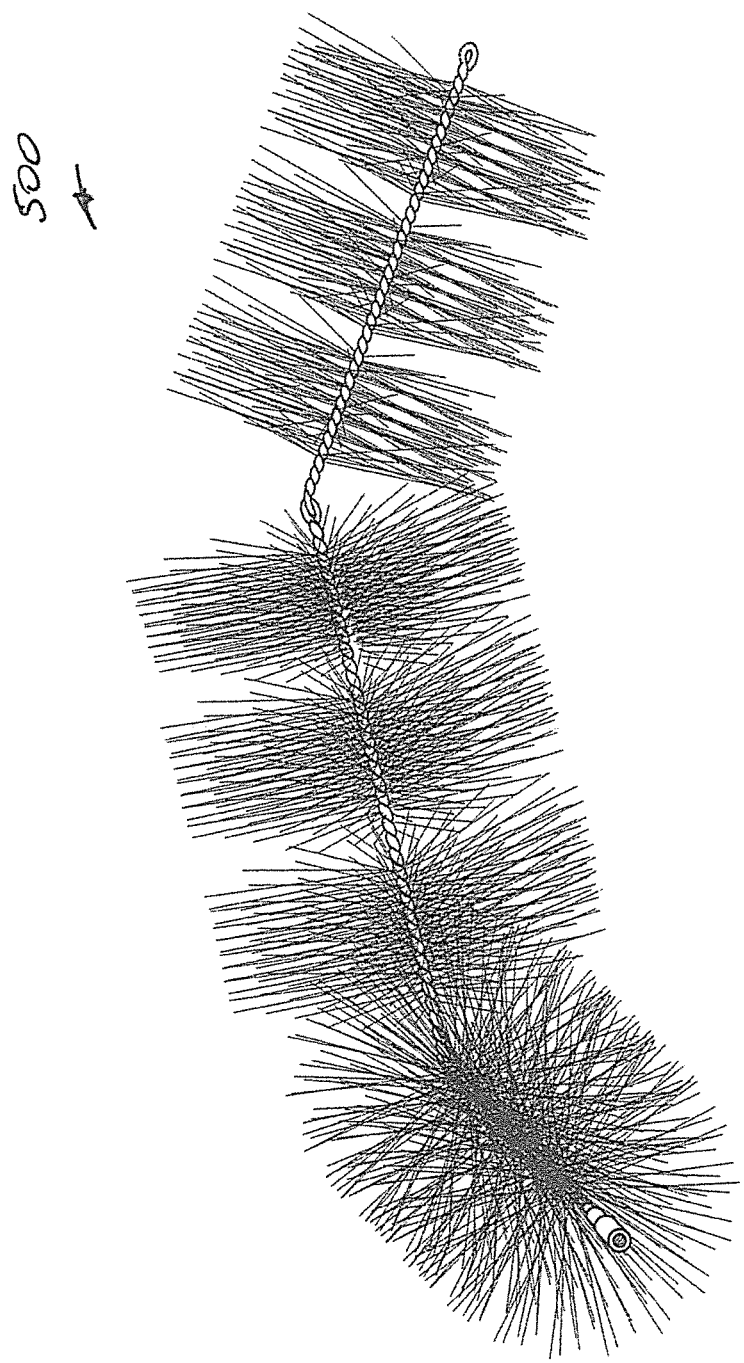
FIG. 127 is a perspective view of another embolisation device of the invention.
Figure 128:
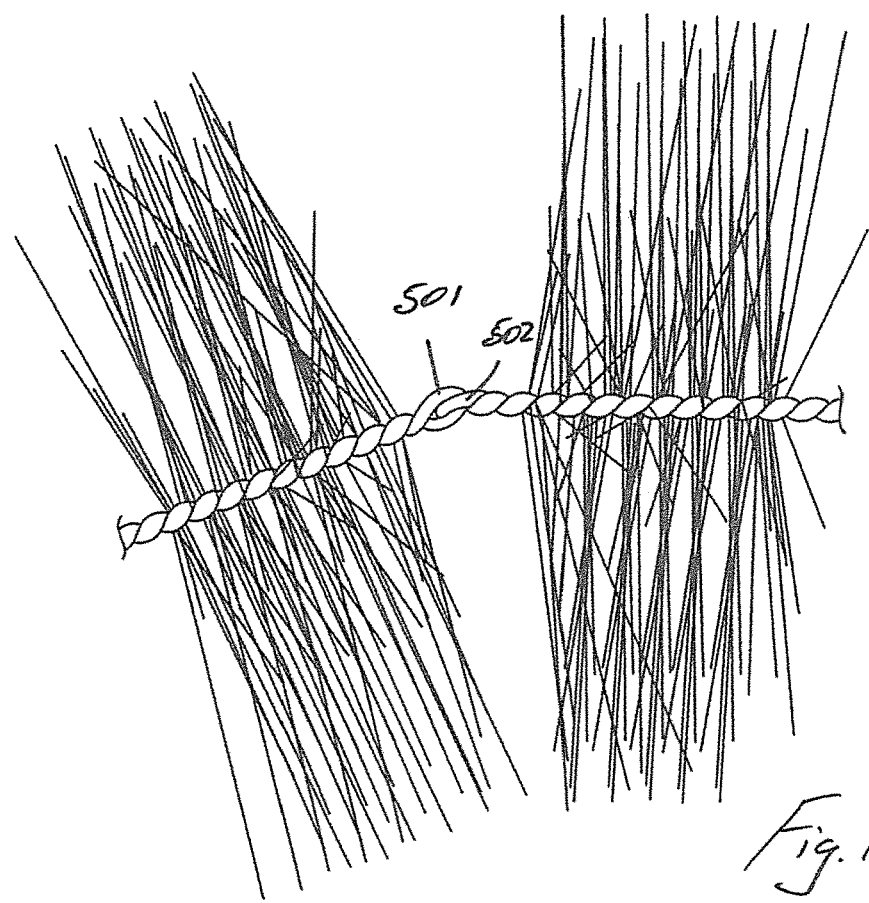
FIGS. 128 and 129 are views of details of the device of FIG. 127.
Figure 129:
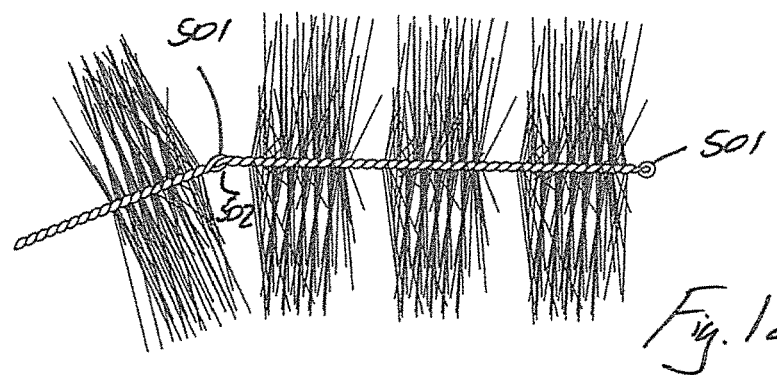
Figure 130:
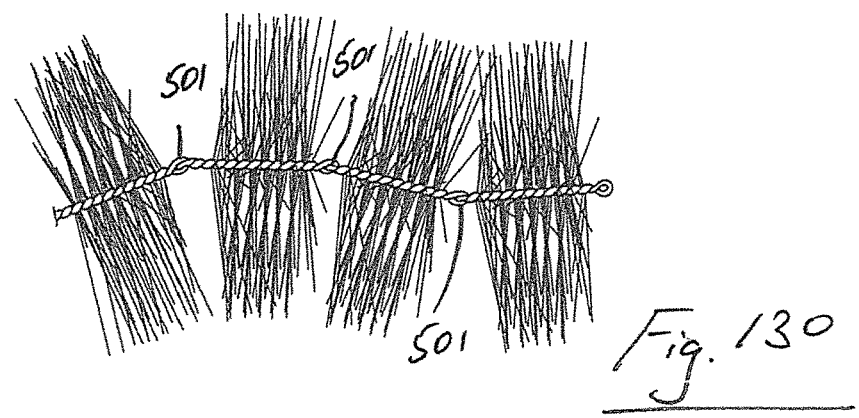
FIG. 130 is a perspective view of another embolisation device of the invention.
Figure 146:
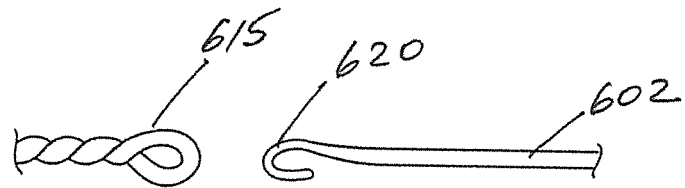
FIG. 146 is an enlarged view of the connection at the distal end of the device.
Figure 145:
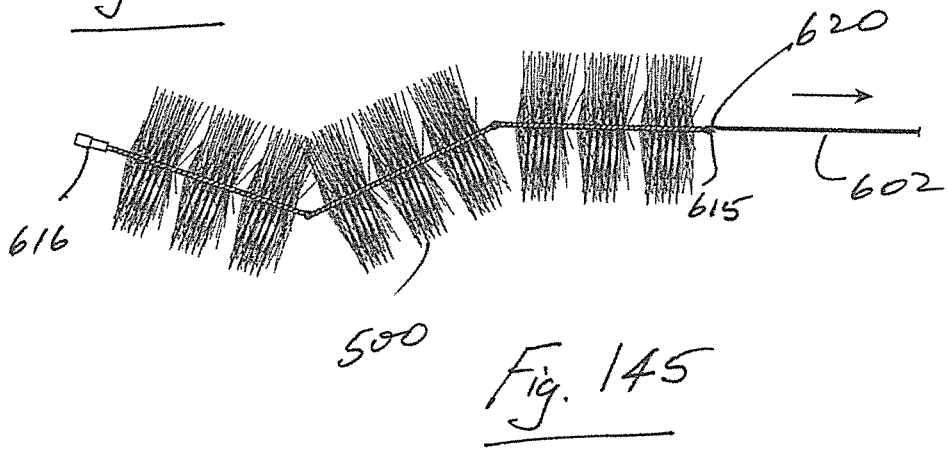
FIG. 145 illustrates the attachment of a loading wire to a distal end of an embolisation device of the invention.
Figure 147:
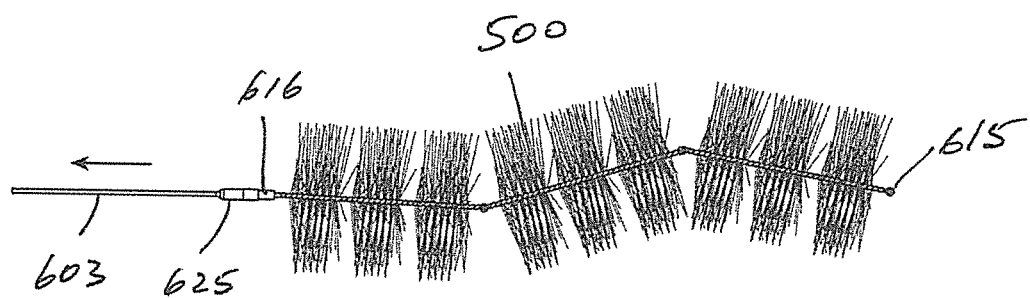
FIG. 147 illustrates the attachment of a delivery wire to a proximal end of the embolisation device.
Figure 148:
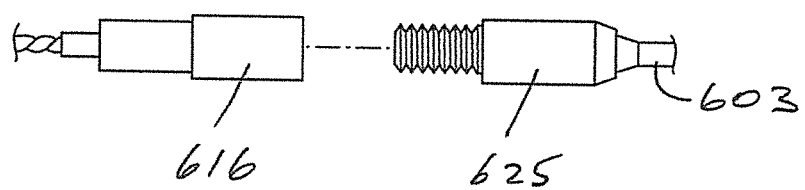
FIG. 148 is an enlarged exploded view of the connection at the proximal end of the device.

For example, as illustrated in FIGS. 127 to 129, an embolisation device 500 is shown which has loops 501, 502 on adjacent stem segments. The loops 501, 502 are interconnected, such that the device can flex at these connections easily. These connections act as articulating points, at which one bristle segment is hinged to the next. This ensures that bending during movement is easily accommodated without potential for device fracture. In addition such connections ensure that the device cannot substantially elongate or compress during delivery. Referring to FIG. 130, in this case there are flexible connections between shorter stem segments for enhanced bending movement.

FIGS. 127 to 130 illustrate bristle devices for delivery into a body lumen comprising a stem and a plurality of flexible bristles extending generally radially outwardly from the stem. The device comprises a plurality of segments, each of which comprises a plurality of bristles extending generally radially outwardly from the stem. At least some of the segments are spaced apart to define spaces therebetween to accommodate bending of the bristles. This bending of the bristles enables the device to be deformed into a collapsed condition, so that the diameter in the collapsed condition is smaller than would be the case if such spaces were not present between the segments.

Use of Single Wire of the Stem FIG. 131.

Often a bristle brush stem is constructed from two wires twisted together. A region of increased flexibility can be constructed by discontinuing one of the wires while continuing the other, thus decreasing the stiffness between adjacent brush sections.

Use of Single Wire of the Stem FIG. 132,

In another embodiment, a suture or monofilament material much less stiff than the bristle brush stem may be used to connect brush segments, providing improving flexibility and articulation points. This suture may be connected to the brush segments using a hypotube. This hypo tube may be attached to the bristle brush stem and suture by crimping.

Spring Connection—FIG. 133.

In another embodiment, a spring connection between individual brush segments may be used to improve the flexibility in the device. This spring may be configured such that in the unloaded configuration it cannot compress. This means that the device cannot substantially decrease while being pushed through the catheter.

Alternatively, the spring may be configured such that the spring can compress or elongate, enabling the physician to adjust the total device length as he deploys the device.

Spring with Tension Wire—FIG. 134.

In some instances, it may be desirable to limit the maximum length of the device. The maximum extension of the spring-like connection above could be limited by the inclusion of a tension wire, which is connected to each segment of the bristle brush. The spring enables bending of the flexible connection, while the tension wire prevents elongation of the device when under tensile loading.

In another instance the device the spring may be configured such that the spring can, enabling the physician to reduce, but not increase the total device length.

O-Ring—FIG. 135.

In another configuration a ring may be used to connect bristle brushes with looped ends. This ring may be constructed from a stiff material, enabling a hinge type joint, or a flexible material in which the ring also flexes during bending of the device.

Simple Wire—FIG. 136.

In another configuration, a wire or string connection, of a much lower stiffness than the bristle brush stem may be used. This wire, because of its lower material stiffness, and/or lower diameter will accommodate bending of the device. The wire or string may be connected to the ends of the bristle brush by an adhesive or weld or solder, or it may be crimped in place by the adjacent wires of the stem of the bristle brush segment.

Connector Element Between Loops FIG. 137.

In another embodiment, looped ends of the bristle brush stem may be connected via a connector element. This element is configured such that its arm or arms on one end, can be bent to a configuration enabling them to pass through the loop. These loops return to the unloaded configuration, meaning they cannot pass back through the loop. A similar configuration exists on the other end of the connector, connecting it to the adjacent bristle brush segment with a looped end.

Connector Element Between Loops—FIG. 138.

Another configuration utilises a wire/string element, woven between the twisted wire stem of the bristle brush segment. This wire/string element, which is more flexible than the stem, emerges from the end of the bristle brush segment, and connects to the next bristle brush segment. A gap between the two bristle brush segments enables the wire/string element to accommodate deformations easily.

Suture/Mono-Filament Connection Between Loops—FIG. 139.

A thread type connection may also be made between adjacent loops of bristle brush segments. This thread may be made from a wire, a polymer mono-filament or suture.

Elastomer/Polymer Tube Connections—FIG. 140.

An elastic tube, wherein the inner diameter of the tube is smaller than the outer diameter of the bristle brush stem. When the elastic tube is pushed onto the end of the bristle brush stem, an interference fit occurs, anchoring the elastic tube to the stem. This elastic tube is anchored to two adjacent bristle brush segments, enable articulation between them.

Alternatively, the elastic tube may be a heat shrinkable material, which when subject to heat reduces its diameter to adhere to the stem of the adjacent brush segments.

Braid Connection—FIG. 141.

In another embodiment, a braid may be used to connect the bristle brush segments.

Elastomer/Polymer Tube Connections—FIG. 142.

A slotted tube may also be used to connect the segments. When under a bending load, the slots can open to accommodate the articulation. The slotted tube may be connected to the stem by crimping or welding or soldering.

Migration may be defined as the movement of an implant from its target vessel location to another location in the vasculature. It is a known complication of embolisation procedures. Since the direction load on any device placed in the vasculature is dependent, at least in part, on the direction of blood flow, it is intuitive that a device may be optimised to prevent migration depending on flow direction.

Veins return the blood flow towards the heart, while arteries carry blood away from the heart. This means that a device implanted in a vein is most likely to migrate towards the heart, while a device implanted in an artery is most likely to migrate away from the heart to a more distal vessel.

A bristle brush embolisation device may be deployed such that its bristles are oriented to prevent, in so far as possible, migration in a given direction. For example the optimal bristle direction for a device deployed in a vein, to prevent migration, is such that the ends of the bristles are pointing towards the heart (FIG. 143). This is because each individual bristle ends will interact with the vessel wall, increasing friction, and preventing migration in that direction. The opposite is true for a bristle brush deployed in an artery. In that case, the bristles should point away from the heart (FIG. 144).

In another configuration, some, or a portion of the bristles may point in both directions such that the device is adapted for use in either a vein or artery.

To ensure that the bristles are pointing towards the heart for venous indications, the device can be pushed into a delivery catheter. As the bristle brush is pushed into the catheter, reducing its diameter to a collapsed configuration, the bristles will point proximally. However, manipulation of the device while pushing into a catheter, may cause damage to the device.

To enable the physician to orient the bristles to point towards or away from the heart, the following loading and delivery system may be provided.

The loading system comprises a loading tube 600 having a distal end which can be connected to a guide catheter 601. The loading tube 600 may be adapted to enable flushing of the device.

The loading system may also comprise a loading wire 602, which can be attached to a distal end 615 of the implant, in this case an embolisation device 500. The loading wire 602 has an end with an engagement 620 feature to engage the distal end 615 of the implant using any suitable mechanism such as via a threaded connection 605 or a hook/loop mechanism 610.

A delivery wire 603 having a distal end 60 which can attach to the proximal end 616 of an implant may be used to push the implant through the loading tube 600 into a guide catheter 601 and on to the target vessel site.

The bristle brush embolisation implant 500 may have a distal end 615 which can be connected to the loading wire 602 (for use in venous vessels) and a proximal end 616 which can be connected to a distal end 625 of the delivery wire 603.

Use in Arterial Vessels (FIGS. 149 to 153)

The device 500 may be used in an artery as follows:

The distal end 625 of the delivery wire 603 is attached to the proximal end 616 of the implant 500.

The proximal end of the delivery wire 603 is inserted through the distal end of the loading tube 600 (FIG. 149) and threaded through to the other end of the loading tube 600. The delivery wire 603 is further pulled until the implant 500 is completely within the loading tube 600 (FIG. 150).

The loading tube 600 is connected to the guide catheter 601.

The bristle brush implant 500 is pushed, using the delivery wire 603, into the guide catheter 601 and on to the target vessel 611 (FIG. 151). The implant 500 is deployed by continuing to push on the delivery wire 603 and/or drawing back the catheter 601 as illustrated in FIGS. 152 and 153.

Use in Venous Vessels (FIGS. 154 to 160)

The end 620 of the loading wire 602 is connected to the distal end 615 of bristle brush implant (with a hook on the end 620 of the loading wire, and a loop 615 on the distal end of the implant 500). The distal end 625 of the delivery wire 603 is connected to the proximal end 616 of the bristle brush implant 500.

The end of the loading wire 602 not connected to the bristle brush 500 is inserted through the proximal end of the loading tube 600 and threaded through to the other end of the loading tube 600.

The loading wire 602 is further pulled until the distal tip of the bristle brush implant 500 is just visible outside the distal end of the loading tube 600.

The loading wire 602 is detached from the implant 500 (FIG. 156).

The distal end of the loading tube 600 is connected to the proximal end of the guide catheter 601.

The implant 500 is pushed into guide catheter 601 and on to a target vessel 611 using the delivery wire 603. The implant 500 is deployed by continuing to push on the delivery wire 603 and/or draining back the catheter 601 as illustrated in FIGS. 157 and 158. After deployment the delivery wire 603 is disconnected from the implant 500.

In one embodiment, the distal end 615 of the implant has a loop configuration for connection to a hook on the end 620 of the loading wire 602, while the proximal end 616 has a threaded end. In another embodiment, both ends are threaded.

The loading wire 602 may be used to ensure that only some of the bristles point in one direction, while the others point in the opposing direction. This is achieved by pulling the bristle brush implant, using the loading wire 602, beyond the point wherein only the distal tip of the implant protrudes out of the distal tip of the loading tube 600. This allows a portion of the bristles to emerge from the loading tube 600. The delivery wire 603 is then used to pull the implant back into the loading tube 600, reversing the direction of this portion of the bristles.

For embolisation it is preferable that the device be oversized to ensure it is anchored safety in the vessel, preventing migration. For this reason all segments of the device should be of a greater diameter than the target vessel. This ensures that the entire vessel lumen is treated and forms a clot, and also that the device cannot migrate.

In order to further prevent migration of the device one or more fibre segments may be added to the device which have enhanced resistance to migration. In such a configuration, an individual segment, or segments may have different mechanical properties to other segments on the device. Preferably this segment, which will be referred to as an anchor segment, is configured so as to also occlude, although perhaps not as rapidly or efficiently as adjacent segments.

This anchor segment may be achieved via increased fibre diameter to increase stiffness, or by use of a stiffer material. Preferably a super-elastic material such as Nitinol is used due to its ability to accommodate large changes in vessel diameter post-implantation. Another advantage of a super-elastic material is that it will not become shape-set if left too long in the catheter, which can occur for many polymers. Furthermore although the anchor segments may utilise a metallic material the other segments may be constructed from a polymer material; thus reducing artefact under imaging such as MRI or CT.

In one configuration a segment 700 to help anchor the device with increased fibre diameter or material stiffness may be at the proximal end of the device (FIG. 159). In another configuration, the anchor segment 700 may be at the distal end of the device (FIG. 160). Alternatively the anchor segment 700 may be placed at both the distal and proximal end of the device (FIG. 161).

In yet another configuration the anchor may be configured such that the fibres in the anchor segment 700 are longer than other segments 701. These fibres may or may not have the same stiffness or diameter of adjacent segments. This is advantages particularly in veins which can be subject to large, temporary vessel distension (e.g. during Valsalva). The other segments 701, with a lower diameter, intended for occlusion are sized according to a lower diameter related to the more permanent vessel state (not distended due to Valsalva). This enables a more dense number of fibres to be delivered through the catheter in segments 701 with a lower diameter enhancing vessel embolisation. The anchor segments 700 will also induce clot formation, albeit potentially at slower rate. Such an anchor segment 700 could be placed at the proximal end of a device (FIG. 162), distal end (FIG. 163) or both proximal end of the device (FIG. 164).

Figure 165:
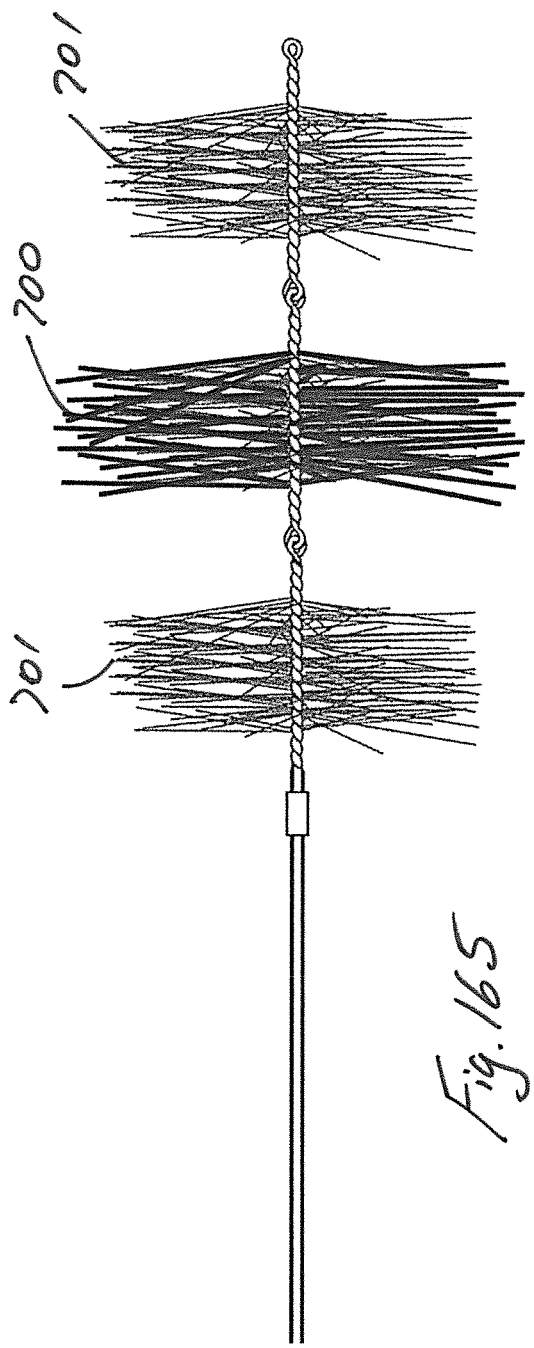

An anchor segment 700 could also be placed within the device mid-section, that is, neither the most proximal nor distal segment. FIG. 165 shows such a configuration with long fibres.

Figure 166:
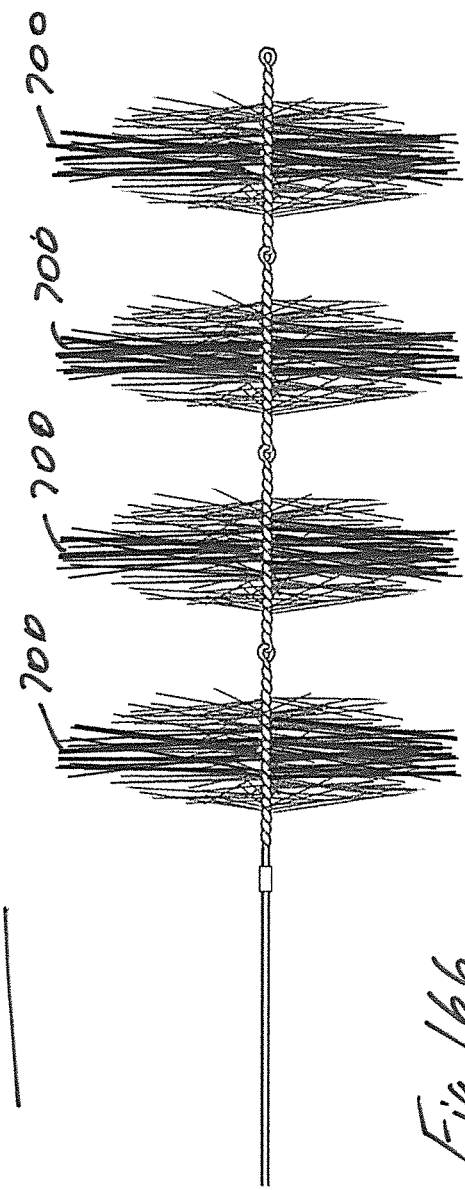

Individual segments with differing groups of bristles within the segment may also be utilised. Such segments will have fibres optimal for both anchoring and promotion of clot. These longer fibres could be configured such that they forma diamond or stepped geometry. In one configuration a series of segments are shown which have longer fibres 700 in the mid-section of the segment, and shorter fibres at the proximal and distal ends of the segment (FIG. 166). These longer anchoring fibres 700 may or may not be of the same stiffness or material as the adjacent fibres in the segment.

Figure 167:
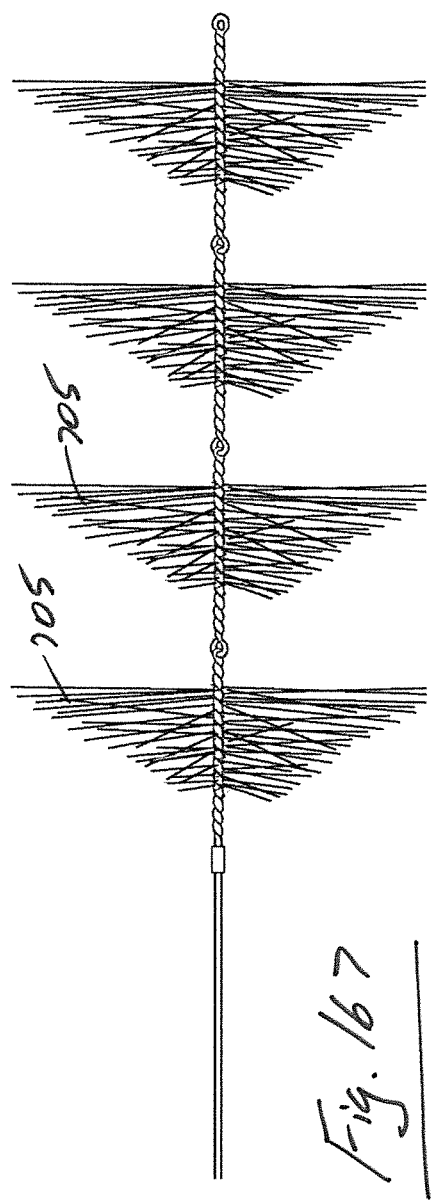
FIGS. 167 and 168 illustrate tapering of fibre length.
Figure 168:
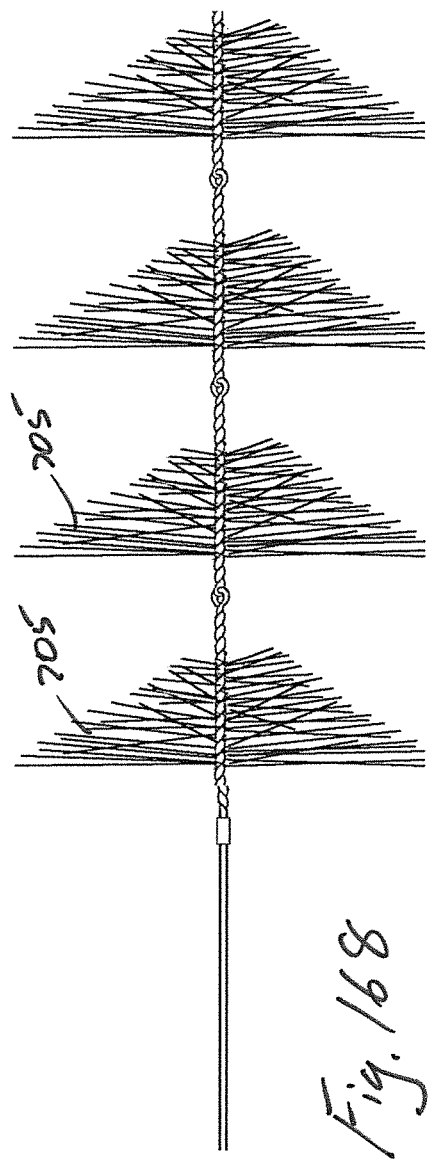

The fibre length in segments 705 may taper from the proximal to the distal end of individual segments, or from the distal to the proximal end (FIGS. 167 and 168).

In cases where the fibres in a segment are of Nitinol, the fibres may be shape-set (via a heating and annealing process) to achieve preferable geometries. In one embodiment, the fibres are shape-set such that they do not project at approximately 90° from the core of the device 710. In one embodiment the fibres are shape set that the ends of the fibres point distally, i.e. from the catheter tip (shown in FIG. 169). This enables easier loading of the device 710 into a loading tube or a catheter for delivery as the fibres are preferably oriented for entry into tubular component. In another embodiment the fibres are shape-set such that some fibres point proximally, while other fibres point distally. In another embodiment, the fibres are shape set such that a kriss-crossing pattern is achieved reducing the aperture between adjacent fibres tangentially and thus improving thrombogencity.

The invention may also be used for the treatment of aneurysms (neuro or peripheral). In one configuration, a single segment 715 may be deployed directly into the aneurysm sac (FIG. 170). In another two segments separated by a flexible, spring, or elastic element. In this case when deployed the elastic member will ensure interaction of the fibres with the vessel wall such as to help anchor the device in the aneurysm. This is shown in FIG. 171. This may be particularly advantageous in the case of wide-necked aneurysms.

In another approach a number of segments 715 could be delivered into the aneurysm sac such that they fill the entire space efficiently. In this type of scenario the individual fibres will interact with one another causing a dense scaffold which cannot straighten out or fall back into the parent vessel (FIG. 172).

Figure 173:
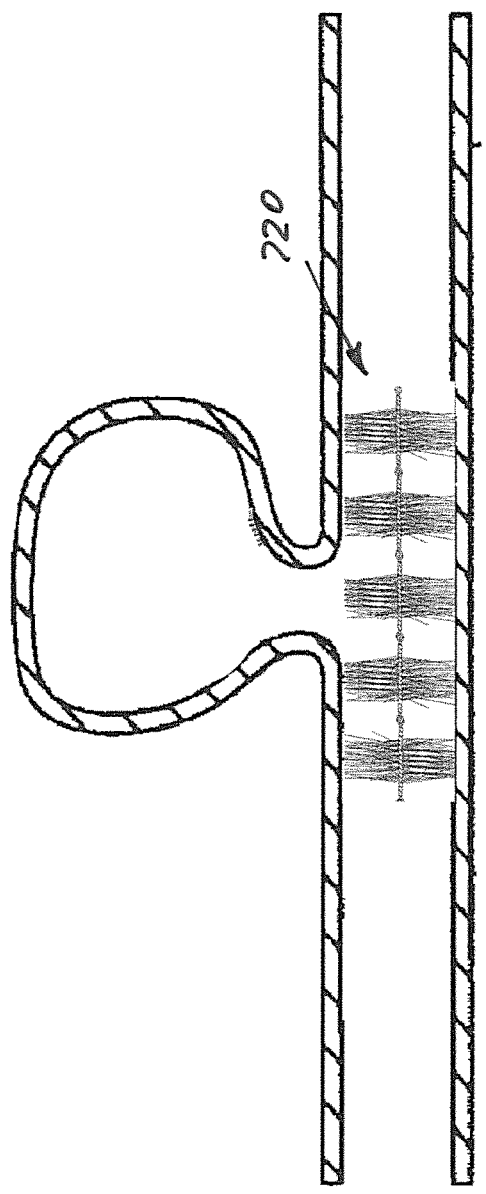
Figure 174:
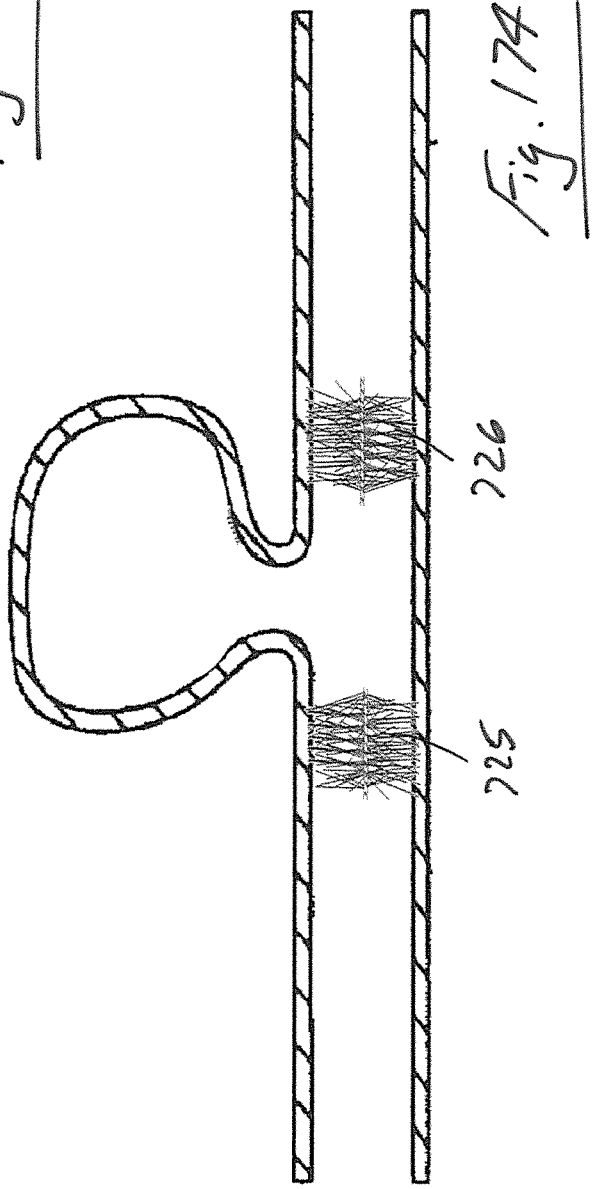
Figure 175:
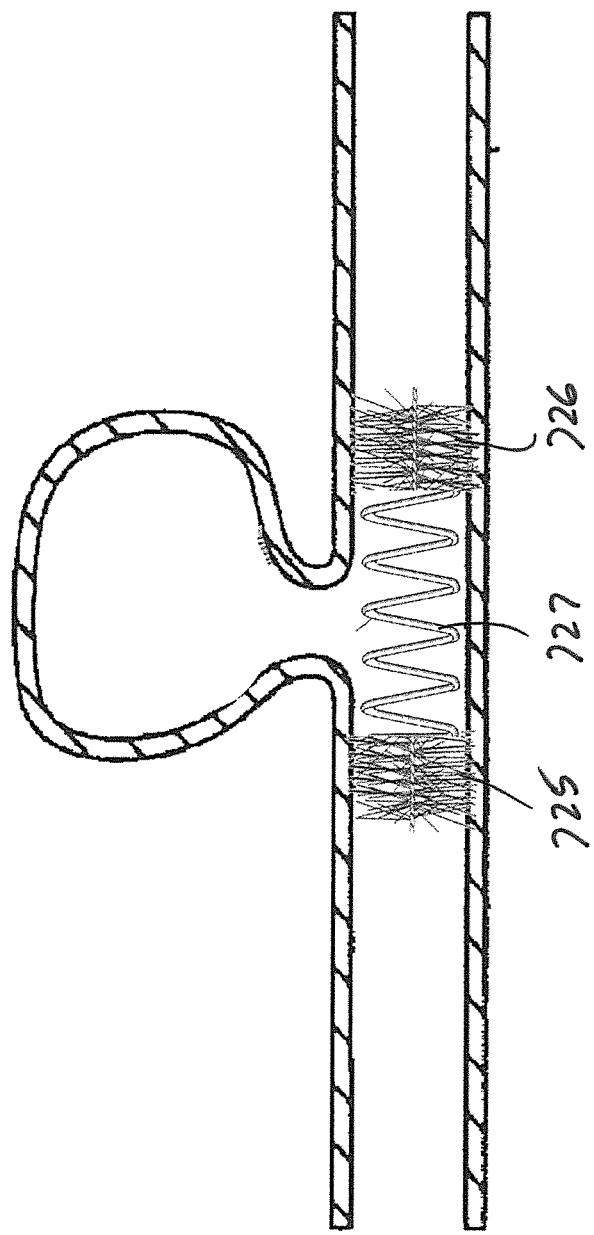

The invention may further be used for the treatment of aneurysms via the parent vessel. In this situation the objective may be to occlude the entire parent vessel (FIG. 173). Once a clot has formed in the device 720 supply to the aneurysm sac is cut off, preventing a rupture and causing clot formation within the aneurysm sac. In another approach the entire parent vessel may be treated with a number of segments 725, 726 which are not connected and placed in the parent vessel distal and proximal to the aneurysm (FIG. 174). In one embodiment the two segments 725, 726 could be connected by an element 727, enabling the physician deploy a single device which results in segments distal and proximal to the aneurysm. In one embodiment this connecting element may be adjustable in length allowing the physician to accommodate a range of distances between proximal and distal ends of the device (FIG. 175).

Figure 176:
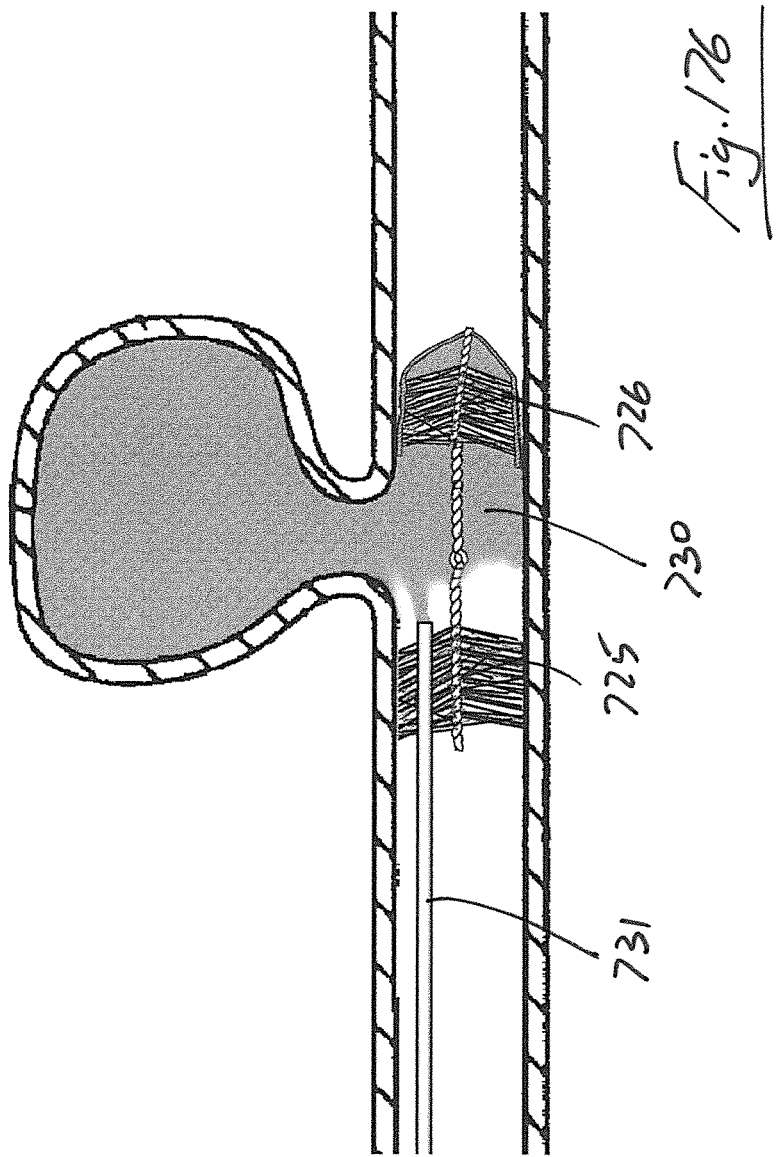

In one method a sclerosant, glue or other embolic 730 may be injected via a catheter 731 between the segments 725, 726 promoting rapid embolisation of the aneurysm (FIG. 176).

Figure 177:
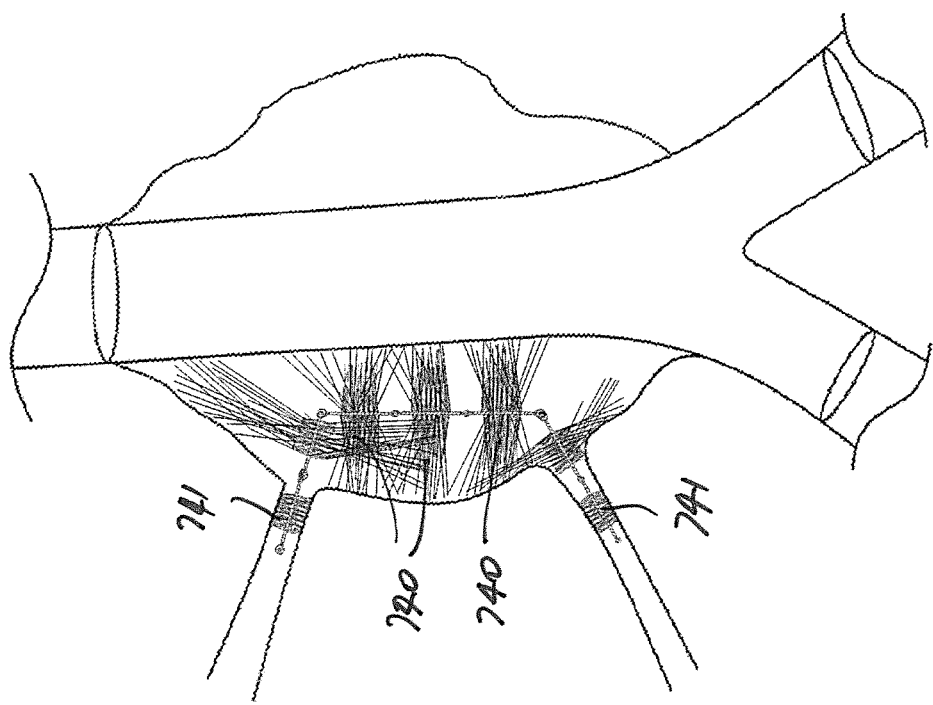

In another embodiment, the device may be used to treat an endoleak. An endoleak is a leak into an aneurysm which has been treated with a vascular graft. Type II endoleaks are of then of a form where there is a vessel flowing into and out of the aneurysm. In this case the physician may treat the aneurysm sac using many coils and the in-flow/outflow vessels. A device such as that shown schematically in FIG. 172 may be used to treat the aneurysm sac. Since the sac is typically large, the segments 740 to be placed within the sac will preferably incorporate much longer and softer fibres than would normally be used in adjacent vessels. Additional devices 741 may be placed in the inflow and outflow vessels. Alternatively a configuration in which the devices comprises segments specifically to fill and cause occlusion on the aneurysm sac may be used, and segments which anchor the device in the in-flow outflow vessels. This is shown schematically in FIG. 177.

In some cases the physician may wish to choose the number of segments which are implanted as the procedure progresses. In this case it may be advantageous to have a number of segments 750 available in the catheter 751 which can be delivered at will. This is shown schematically in (FIG. 178). In this figure all segments 750 are not connected, nor is a delivery wire attached. Instead a push-wire 752 is used to push the segments 750 through the catheter 752. This allows one-by-one deployment of the segments 750.

In one embodiment, there is a temporary interlocking connection between adjacent segments. The most proximal segment is connected the delivery wire by an interlocking connection. This enables the physician to push and pull the segments while they are still within the catheter. Once a segment is pushed out of the catheter its temporary interlocking connection is undone, enabling it to detach from the adjacent proximal segments. At any stage prior to the proximal interlocking portion of a segment exiting the catheter tip, it can be retracted by retracting the delivery wire.

It may be preferable to enhance the thrombogencity of the device by modifying the Nylon fibres by etching. This increases surface roughness increasing surface area and propensity for platelet adhesion. Nylon fibres are etched to increase the surface roughness thus increasing thrombogencity. This etching may be achieved using by immersing the fibres in a solution of 75 parts potassium dichromate, 1250 parts sulphuric acid and 120 parts water.

In some cases it may be preferable for the physician to be able to pass a catheter 760 through a device 761 once delivered. The ease of passing a catheter 760 through the device may be improved by offsetting the stem core 762 of the device towards the outer diameter of the device, such that the fibre length varies about the stem circumference as shown in FIG. 179. This is shown in cross section in FIG. 180. In one embodiment in some regions about the circumference there are no fibres present, or the fibres are trimmed to a length close to zero. In another configuration two parallel segments or devices of this type could be connected for enhanced occlusion (shown in cross section in FIG. 181).

A method may be used wherein a device is used to prevent backflow, known as reflux, of particles delivered during particle embolisation. These particles may be used to cause end-organ tissue neucrosis or for the delivery of radio-embolisation or chemo-embolisation. One example is the treatment of uterine fibroids using particles, in which the objective is to send as distally as possible until they become trapped in the microvasculature (see FIG. 182). These particles can damage other areas of the body if allowed to leave the target vessel or end organ. When used, the intent is to deliver the particles until stasis is achieved. Once this occurs it is a problem that particles can flow backwards and travel to non-target locations.

Placement of a bristle brush device will prevent these particles from travelling proximally once stasis occurs as the particles will become trapped in the fibres. To deliver the particles a catheter 760 is passed through the bristle brush 761, and particles then injected through the catheter 760 (FIG. 183).

Preferably this type of device 761 will be constructed so as to allow blood flow for a period of time (enabling the particles to travel distally to the target location), and eventually occlude once the particle delivery is complete. In one approach the bristle brush may be removed once the particle embolisation is complete.

The device disclosed may also be used for the treatment of saphenous veins for the treatment of lower limb varicose veins. It is well described that failure at the sapneous vein junction is important and that an implant or permanent ligation at this location would prevent recurrence. A permanent or biodegradable fibre device may be particularly advantageous for prevention of these failures.

Figure 184:
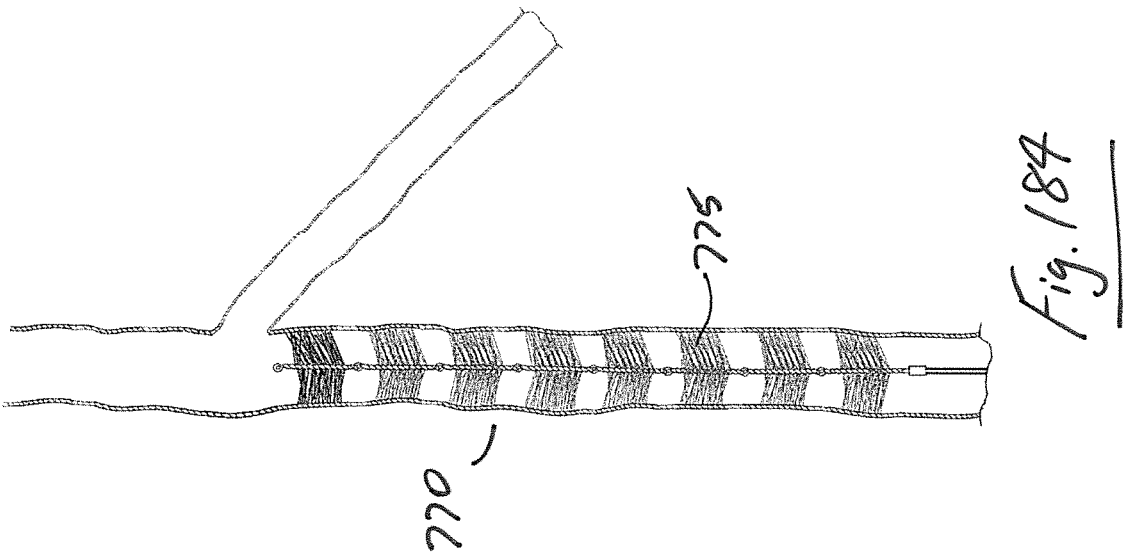
FIGS. 184 to 186 illustrate steps in one method for using the device.
Figure 185:
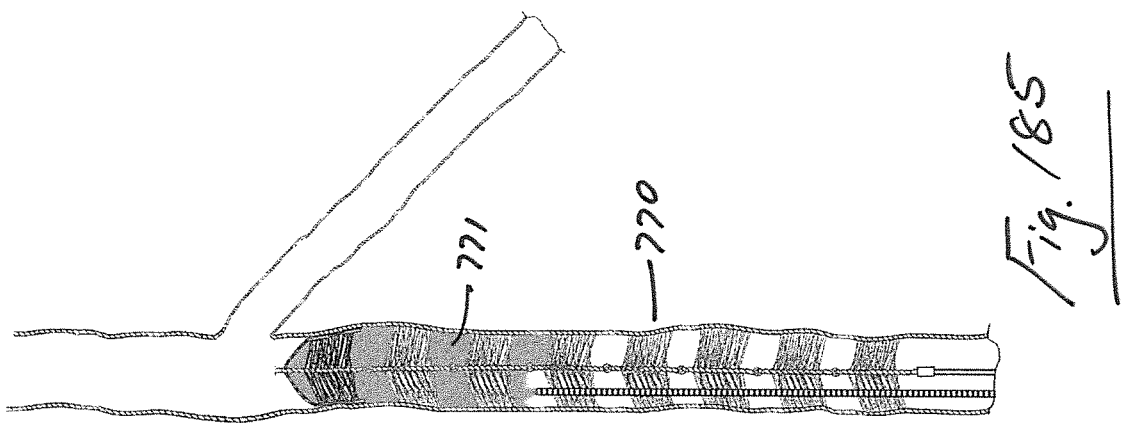

A method may be used in which an embolisation device 775 is first deployed into a saphenous vein 770 under ultrasound. The device may treat the entire length, or a significant portion of the length, of the saphenous vein. A sclerosant agent or other embolic or glue may then be injected by the physician along the length of the device, treating perforators and collaterals. This is shown schematically in FIG. 184, 185.

Figure 186:
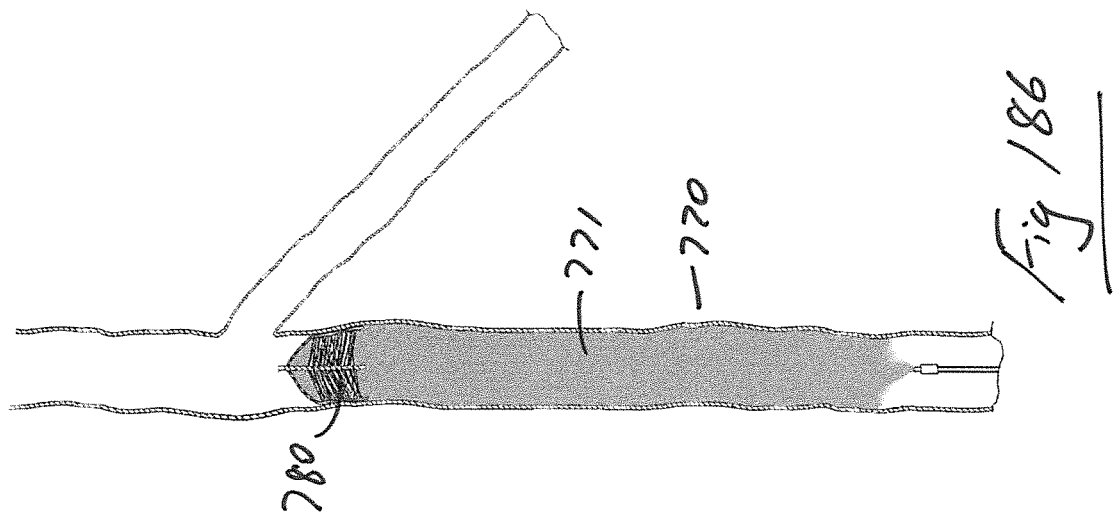

In another method (FIG. 186) a short device 780 may also be placed at the cranial end of the saphenous vein. A scloerosing agent may be injected in the caudal portion with the device preventing cranial migration of the embolic into non target vessels.

The device may be left permanently in the saphenous vein or retrieved into the catheter for removal once the procedure is complete.

Generally this is a procedure will be performed under ultrasound imaging. It is therefore preferable that the device be comprised of echogenic materials, or have an echogenic coating, to enable the physician the device during placement. In particularly the stem may be comprised of an echo-genic material. More preferably echogenic markers may be placed at the proximal and distal ends of the device.

In one embodiment the device is configured so as to control the embolic to remain between the device ends. In another embodiment the device is configured so as to allow caudal flow the sclerosant but not cranial flow.

Figure 188:
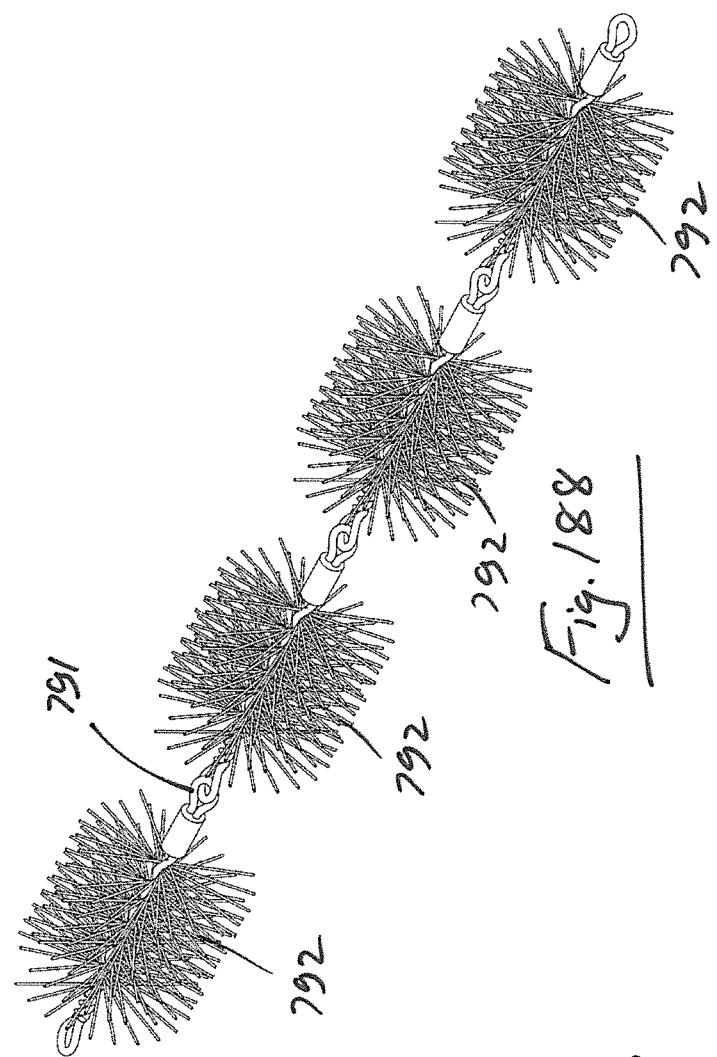
Figure 187:
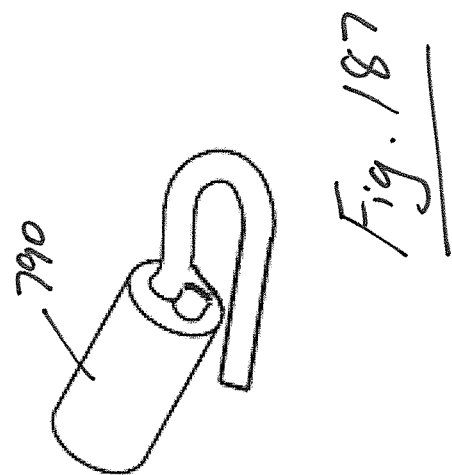

To enable efficiency in manufacture, the looped end of a segment may be connected to an adjacent segment by means of modular unit 790 as shown in FIG. 187. This modular unit 790 is configured so as to have an open configuration to enable it to be connected through the loop 791 of the adjacent segment. This is then closed by mean of a crimp or weld making a permanent flexible connection between adjacent segments 792 as shown in FIG. 188.

In another embodiment the segments 792 may be manufactured so as to not have loops at either end. A modular unit 795 of two interconnected loops may be used to connect the segments by means of crimping or welding or other (FIG. 189, 190).

In one embodiment the modular unit may be constructed from a wire and hypotube. In another embodiment the modular unit may be constructed from a single cut hypotube cut and formed into a suitable shape.

Although the bristle brush segments can embolise a vessel, a clot must build within the scaffold which takes time to occur. In one embodiment a flow restrictor such as a membrane 800 may be included on the proximal end of the device restricting blood flow into the device and causing stasis. The more distal fibre segments further promote embolisation, and anchor the device in the vessel along the target vessel. Although a focal occlusion may be sufficient at the proximal end due to the effect of the membrane 800, it is frequently the case that a physician wishes to embolise a vessel length due to the presence of collaterals or aneurysm.

The membrane 800 may be impermeable in order to constitute a complete flow blocker. This ensures rapid cessation of the in-flow causing stasis along the vessel length. This encourages more rapid generation of clot within the fibre scaffold along the target vessel length.

The membrane 800 may be comprised of self-expanding material to ensure that it expands to fill the vessel lumen upon deployment. In another embodiment the adjacent fibres of the most proximal fibre segment move the membrane form the collapsed to the expanded state upon deployment. The membrane may be of a disc shape and placed at the proximal end of the device (as shown in FIGS. 191 to 193), or at the distal end of a device, or at both ends of the device.

Figure 197:
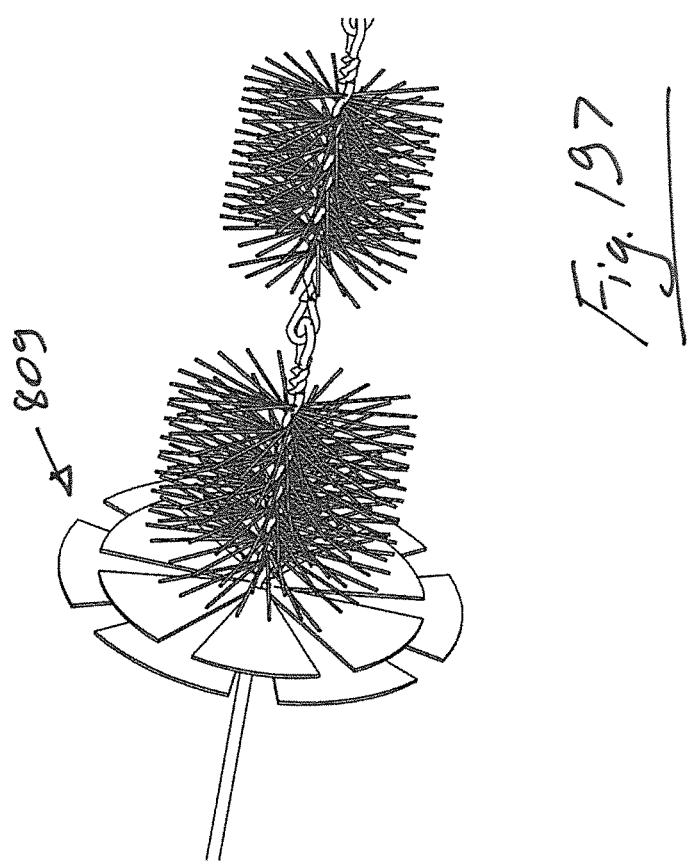

In some cases a membrane 805 may have a number of slots 806 to facilitate folding of the device for when collapsed in a delivery catheter, and to ensure a more uniform expansion (FIG. 194). In another case a membrane 809 may comprise a number of layers, with (FIG. 197) or without slots. The layers may have the same or different diameter. In one embodiment the more distal layer has a lower diameter than the more proximal layer. In another embodiment a membrane 810 may be comprised of a number of overlapping leaflets or petals 811 (FIG. 195). This overlapping construction further improves folding and prevents formation of gaps when deployed in the vessel due to non-uniform expansion of the membrane.

A membrane such as a disc may be treated so as to have predefined folds to aid collapse for delivery, and provision of a seal against the vessel wall upon deployment.

In one embodiment, if placed at the proximal end of the device, the membrane is collapsed by the catheter or loading tube tip during retraction into the catheter or loading tube. Upon deployment the fibres distal the membrane expand the membrane out to meet the vessel wall restricting flow.

Figure 198:
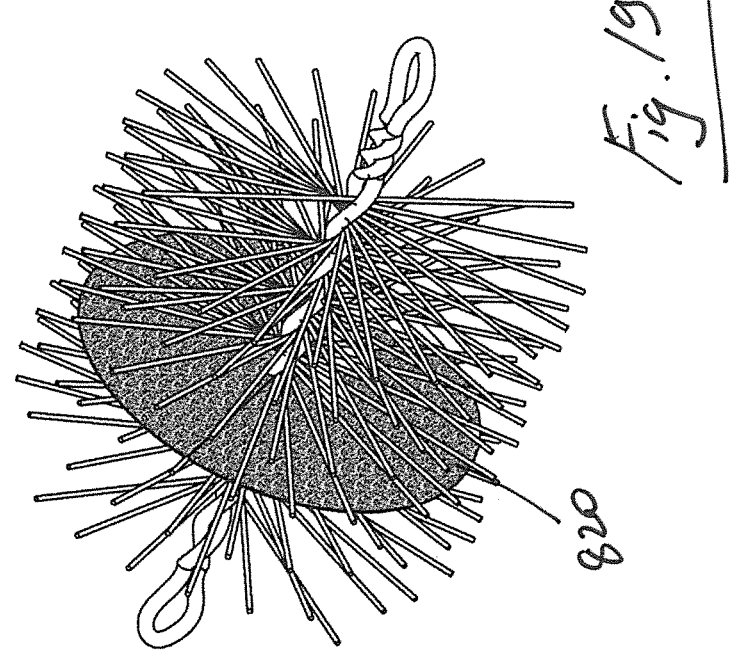

In one configuration a membrane 815 may be placed within the fibre segment such that there are fibres both immediately distal and proximal to the segment (FIG. 196). These fibres serve to support the membrane during loading and deployment ensuring that it is collapsed and expanded in a controlled way In some cases membrane may have a diameter which is greater than or less than the segment diameter. FIG. 198 shows a membrane 820 with a diameter lower than the segment diameter. In this situation, the membrane diameter must be at least that of the target vessel. In another configuration the membrane may be comprised of a number of layers of different diameters which may be greater than the segment diameter (FIG. 197) or less than the segment diameter.

Figure 199:
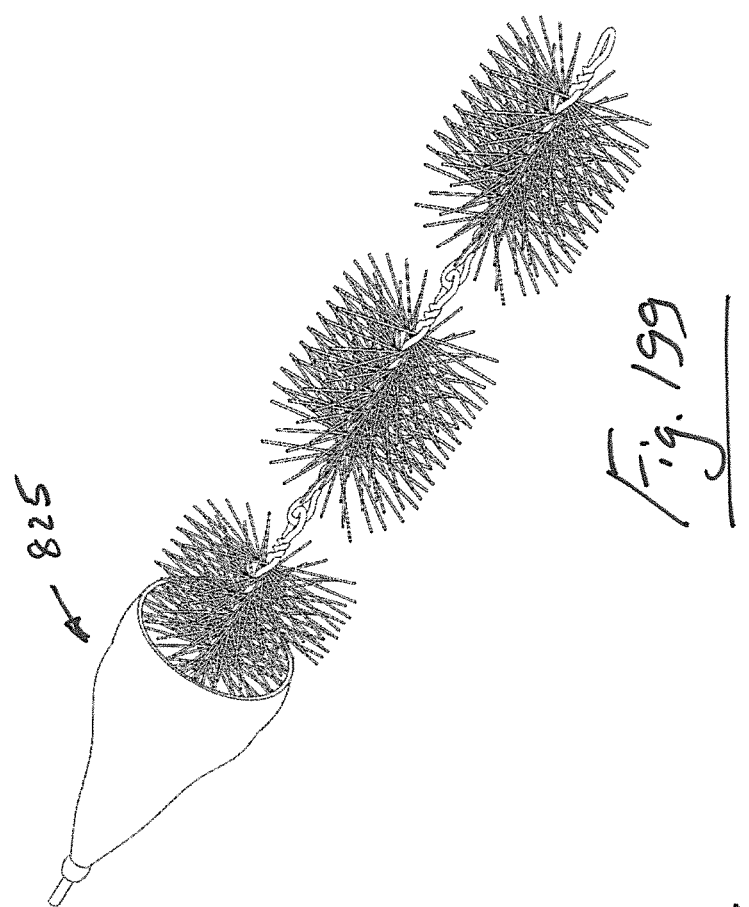

In another configuration, a membrane 825 may constitute a wind-sock type geometry which surrounds some or all of the fibres of a segment (as shown in FIG. 199). To ensure sufficient flow restriction the wind-sock diameter should be at least that of the target vessel. In another embodiment, a balloon type geometry may be incorporated. In this case a fibre segment may reside within the balloon. Upon deployment from the catheter, the expansion of the fibres from a collapsed condition cause opens the balloon up to fill the vessel lumen causing a flow restriction.

Figure 200:
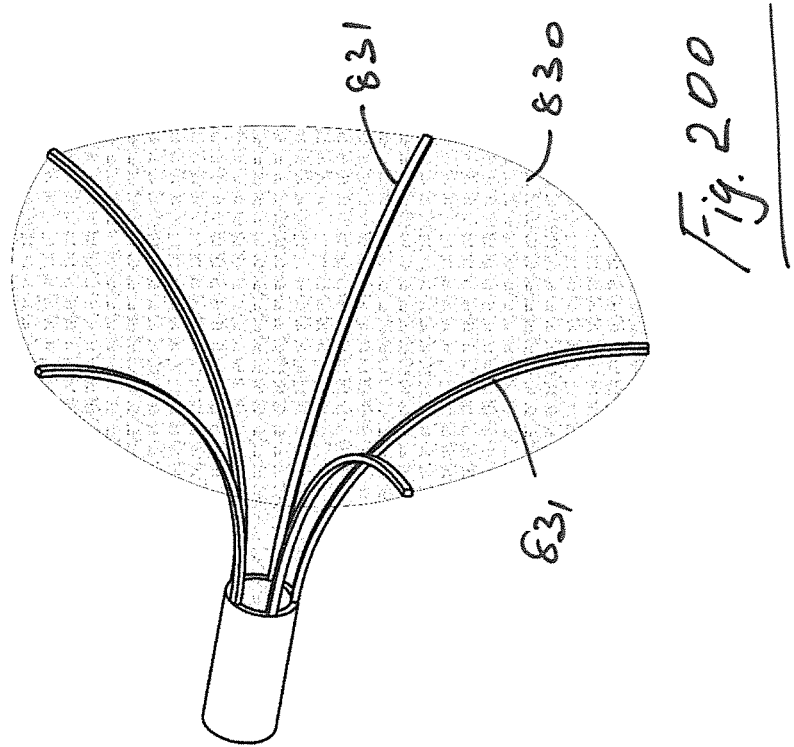

In yet another configuration, a membrane 830 may be supported by a number of struts 831 to control expansion and contraction during deployment and loading, further aiding a reliable flow restriction of the lumen. This is shown schematically in FIG. 200. These struts may be made from Nitinol.

In one embodiment the edges of the membrane incorporate frayed edges to help ensure a seal against the vessel lumen.

The membrane may be comprised of a film, weave, braid or fabric construction. Suitable materials include PTFE, Nylon, PET, PEEK, Polyurethane, Polypropylene and Silicon. A fine Dacron mesh may also be used.

A membrane may be manufactured in-situ on a fibre segment by dipping of some or a portion of the device in silicone or another elastomer. When cured the webbed effect and membrane will be formed between the fibres, acting as a membrane to aid flow restriction.

In one embodiment the fibres are interconnected with an array of micro fibres 'a web'. These microfibers increase the blood contact surface area and reduce aperture size to facilitate rapid occlusion The 'web' may be manufactured by extruding the microfibers onto the brush, weaving the microfibers through the brush fibres and/or using an adhesive to attach the microfibers to the brush fibres.

A process known as electrospinning may also be used to position the microfibers on the brush.

Figure 201:
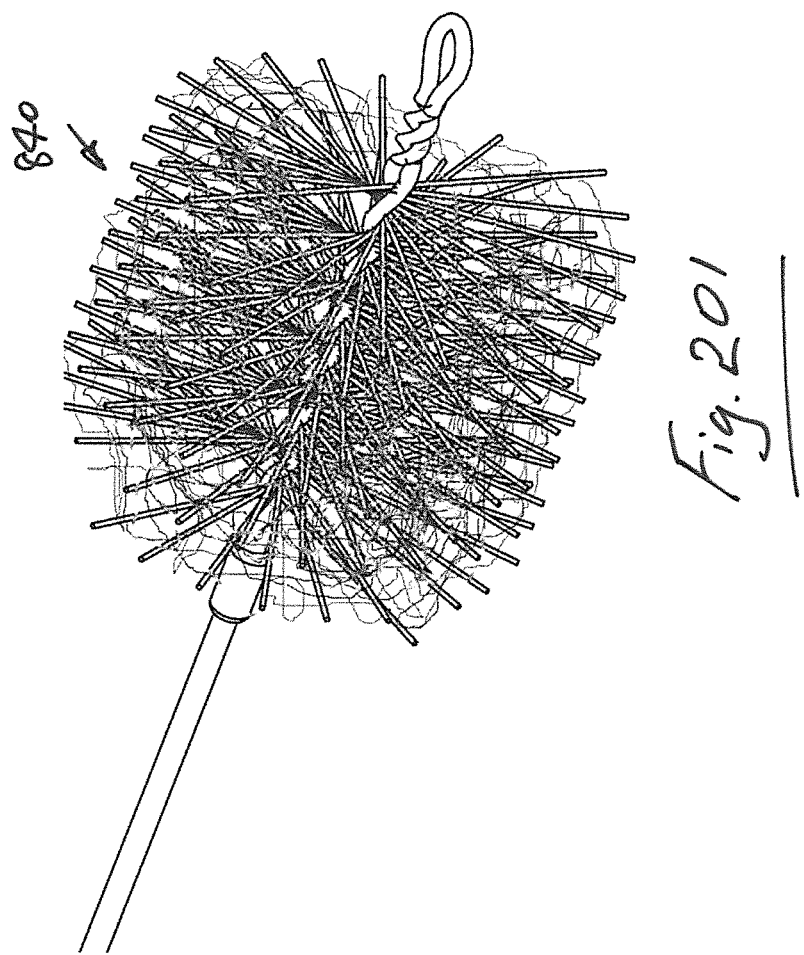
FIG. 201 schematically illustrates electrospinning to position the microfibers.

The occlusion performance of a fibre segment 840 may be further enhanced by the addition of fibres to cross the existing fibres (FIG. 201). In one embodiment a uniform distribution of fibres is added. In another embodiment the density of the added fibres increases towards the outer diameter of the segment. This is preferable since as the distance from the stem increase, so too dos the distance between the fibres, reducing the efficiency of blood clot formation. This could be achieved by electro spinning. In one embodiment the added fibres are of a lower diameter than the other fibres in the segment. In another embodiment they are of the same or a larger diameter. The fibres may only be added to the distal and proximal ends.

As the objective of the invention to promote a blood clot, the number of fibres which can be fitted into a catheter must be maximised to ensure embolisation. Depending on the fibre diameter, more fibres can be fitted into the delivery catheter. This is shown schematically in FIGS. 202, 203. More fibres mean a greater surface area for platelet and clot adhesion, and a smaller gap between adjacent fibres. A smaller gap between adjacent fibres means that the distance or thickness of thrombus which must form is lower in order for adjacent thrombus to meet.

Typically catheters have an internal diameter of 0.038, 0.056, and 0.068 inches for guide catheters 4, 5, 6 French respectively. Smaller micro-catheters 0.022 to 0.028 also exist. The length of the fibre segment, gap between fibre segments and fibre density must be tuned to ensure that a device can be pushed through the catheter without becoming stuck.

The stem of the device is typically constructed from a two wires (as shown in FIG. 113) or from a single continuous wire bent so as to achieve two parallel wire sections. A series of fibres is placed between the wires. One end of the wire(s) is fixed while the other is twisted to achieve a cylindrical brush segment. This twisting action results in a stem, the diameter of which is related to the diameter of the wire used. The stem diameter chosen must have enough strength to securely hold the fibres in place once twisted without causing a major increase in the profile particularly when loaded in a catheter. Preferred stem wire diameters are outlined in the table below.

Figure 204:
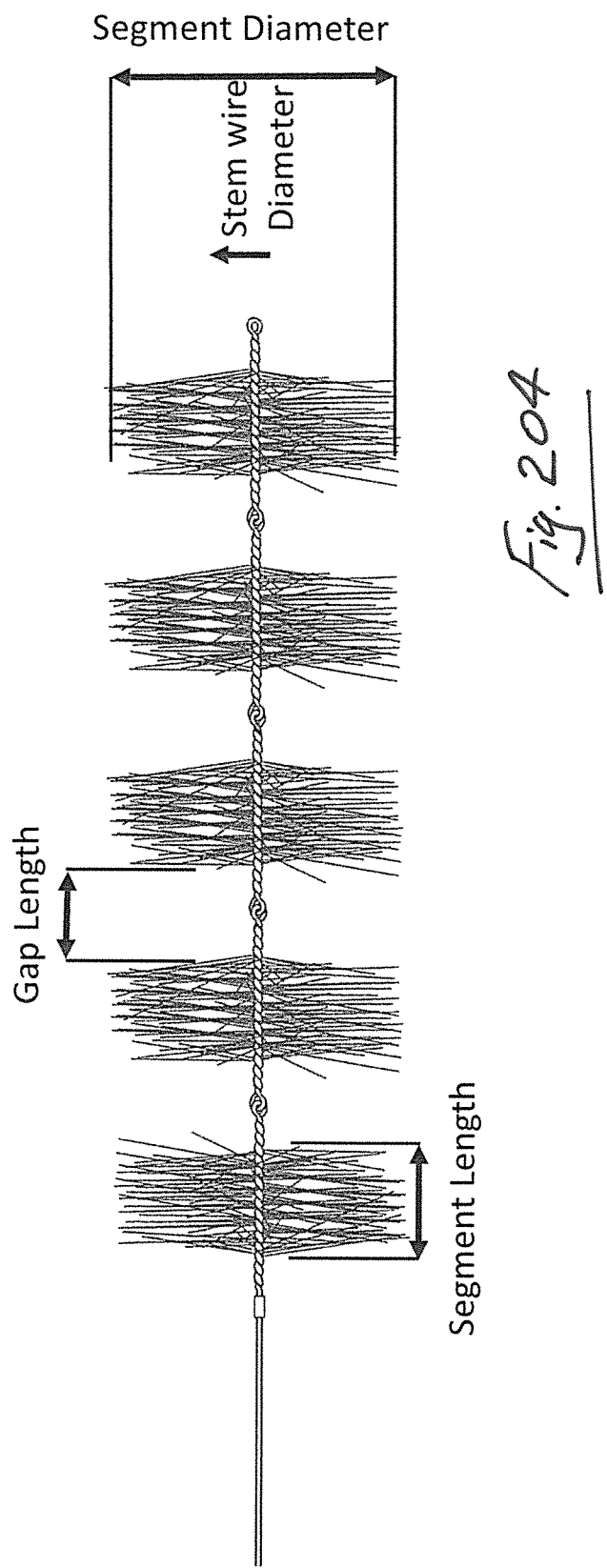
FIG. 204 is an illustration of an embolisation device of the invention.

The table below outlines ranges of fibre density, diameter, stem diameter, segment length and gap length according to FIG. 204 which may be used in the invention. Devices with a lower density of fibres than this will not be efficient in promoting clot formation, particularly in larger diameter vessels.

The density of the fibres is the number of fibres present per cm of segment length. For example in a segment of 6 mm in length, with a density of 100, there will be 60 fibres.

| Approximate Gather ID (inches) | Stem Wire Diameter | Segment Diameter (mm) | Gap Length (mm) | Fibre Diameter (in) | Maximum Segment Length (mm) | Fibre Density (number per cm of segment length) |
| --- | --- | --- | --- | --- | --- | --- |
| 0.023 | 0.003-0.006 | 3-6 | 1-3 | 0.001-0.002 | 3-4 | 100-200 |
| 0.038 | 0.003-0.008 | 6-8 | ≥2 | 0.002-0.003 | 3-7 | 100-300 |
| 0.056 | 0.004-0.012 | 8-10 | ≥2 | 0.002-0.003 | 3-7 | 100-800 |
| 0.056 | 0.004-0.012 | 10-12 | ≥2 | 0.002-0.003 | 3-7 | 100-800 |
| 0.056 | 0.004-0.012 | 12-16 | ≥2 | 0.002-0.004 | 3-6 | 100-800 |
| 0.068 | 0.004-0.012 | 10-18 | ≥2 | 0.002-0.004 | 3-6 | 100-400 |
| 0.078 | 0.004-0.012 | 10-24 | ≥2 | 0.002-0.005 | 3-6 | 100-400 |

In some particular embodiments the following are deliverable through a catheter, but are also efficient in promoting clot formation. Devices with a lower density of fibres than this will not be efficient in promoting clot formation, particularly in larger diameter vessels. Specific details are outlined in the table below.

| Approximate Cather ID (inches) | Stem Wire Diameter | Segment Diameter, Occluder (mm) | Segment Diameter, Anchor (mm) | Gap Length (mm) | Fibre Diameter (in) | Maximum Segment Length (mm) | Fibre Density (number per cm of segment length) |
| --- | --- | --- | --- | --- | --- | --- | --- |
| 0.023 | 0.004 | 4-5 | 4-6 | 1-3 | 0.001-0.002 | 3-4 | 100-300 |
| 0.038 | 0.006-0.008 | 6 | 8 | ≥2 | 0.002-0.003 | 3-6 | 100-300 |
| 0.056 | 0.008-0.010 | 12 | 15 | ≥3 | 0.002-0.003 | 4-5 | 300-800 |

-continued

| Approximate Cather ID (inches) | Stem Wire Diameter | Segment Diameter, Occluder (mm) | Segment Diameter, Anchor (mm) | Gap Length (mm) | Fibre Diameter (in) | Maximum Segment Length (mm) | Fibre Density (number per cm of segment length) |
|---|---|---|---|---|---|---|---|
| 0.068 | 0.008-0.012 | 15 | 17 | ≥3 | 0.002-0.004 | 3-6 | 200-800 |
| 0.078 | 0.008-0.012 | 18 | 22 | ≥3 | 0.002-0.004 | 3-6 | 200-1000 |

Where segments are longer than 6 mm, for the densities and segment diameters required, it will not be possible to deliver the segments through the catheter inner diameters outlined.

The device may be comprised of one type of segment whereby each segment is of equal efficiency in terms of both anchoring and occlusion.

In one configuration two different segments types may be used, both intended to both anchor the device and cause occlusion, but one which is more optimal for anchoring while the other is more optimal for occlusion.

In one configuration the device may comprise only one segment. The segment may be configured so as to have a variable diameter along its length with increased fibre length at the distal or proximal end, or both. In another embodiment a single segment has a denser fill at the proximal end and/or distal end than at the mid-section. In yet another embodiment more than one diameter is used for the fibres such that some fibres serve to anchor the device while other fibres better promote occlusion.

In another embodiment, the device may be configured so the segment or segments contain different fibre types wherein one type is more optimal for anchoring while one type is more optimal for occlusion.

In another embodiment a membrane enhance immediate flow restriction may be placed towards or at the proximal or distal, or both ends of the device.

The invention provides various embolisation devices for promoting clot formation in a lumen comprising a stem and a plurality of flexible bristles extending outwardly from the stem, the bristles having a contracted delivery configuration and a deployed configuration in which the bristles extend outwardly from the stem to permanently anchor the device in a lumen. Referring for example to FIGS. 205 to 208 the embolisation devices 900 are first loaded into a delivery catheter which is inserted into a target vessel 902. The device 900 is deployed. In some cases the device 900 is mounted on a delivery wire 903 which is detached from the device 900 after deployment. The bristles of the device 900 are anchored in the lumen 902 and promote clot formation (FIG. 207) until the vessel is completely occluded (FIG. 208).

Modifications and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

The invention is not limited to the embodiments hereinbefore described, with reference to the accompanying drawings, which may be varied in construction and detail.

REFERENCES

1. The Technology of Expansion. Terumo Interventional Systems. Downloaded on Feb. 21, 2013 from http://www.terumois.com/products/embolics/AZUR.aspx
2. Ekeh et al., Complications arising from splenic artery embolisation: a review of an 11-year experience. The American Journal of Surgery, 205, 250-254, 2013
3. Ryer et al. 2013, Comparison of outcomes with coils versus vascular plug embolisation of the internal iliac artery for endovascular aortoiliac aneurysm repair. Journal of Vascular Surgery, Volume 56, Issue 5, November 2012, Pages 1239-1245.
4. Rastogi et al., Unintended coil migration into the right ventricle during the right ovarian vein coil embolisation. Vascular and Endovascular Surgery, 2011 October; 45(7).
5. Marsh et al., Coil Protruding into the Common Femoral Vein Following Pelvic Venous Embolisation. Cardiovascular Interventional Radiology (2008) 31:435-438
6. Beddy et al., Testicular varicoceles. Clinical Radiology (2005) 60, 1248-1255
7. Beecroft et al., Percutaneous varicocele embolisation. Canadian Urological Association Journal. September 2007, Volume 1, Issue 3
8. Kessel et al., Transcatheter Embolisation and Therapy. Springer ISBN 978-1-84800-896-0. Published 2010
9. Balian et al. Pelviperineal venous insufficiency and varicose veins of the lower limbs. Phlebolymphology. 2008; 15(1):17-26.
10. Messé et al., Atrial septal abnormalities (PFO, ASD, and ASA) and risk of cerebral emboli in adults. Downloaded on Feb. 22, 2013 from www.uptodate.com
11. St. John Sutton et al., Devices for percutaneous closure of a secundum atrial septal defect. Downloaded on Feb. 22, 2013 from www.uptodate.com
12. Letourneau-Guillon et al., Embolisation of Pulmonary Arteriovenous Malformations with Amplatzer Vascular Plugs: Safety and Midterm Effectiveness. Journal of Vascular and Interventional Radiology, Volume 21, Issue 5, Pages 649-656, May 2010.
13. Wang et al., The Amplatzer Vascular Plug: A Review of the Device and its Clinical Applications, CardioVascular and Interventional Radiology, August 2012, Volume 35, Issue 4, pp 725-740.
14. Yoo et al., Preoperative portal vein embolisation using an amplatzer vascular plug. European Radiology (2009) 19: 1054-1061.
15. Pelage et al. What is Azur Hydrocoil and How Does it Work? Presented at Society of Interventional Radiology, 2011.
16. Van Der Vleuten et al., Embolisation to treat pelvic congestion syndrome and vulval varicose veins. International Journal of Gynecology and Obstetrics 118 (2012) 227-230

17. Bleday et al., Treatment of haemorrhoids, Sep. 24 2012. Downloaded on Feb. 22, 2013 from www.uptodate.com
18. Nyström et al., Randomized clinical trial of symptom control after stapled anopexy or diathermy excision for haemorrhoid prolapse. Br J Surg. 2010; 97(2):167.
19. A M Gardner, Inferior vena caval interruption in the prevention of fatal pulmonary embolism, American Heart Journal (impact factor: 4.65). 07/1978; 95(6):679-82.
20. Kazmier F J; Shaggy aorta syndrome and disseminated atheromatous embolisation. In: Bergan J J, Yao J S T, editors Aortic surgery Philadelphia: W B Saunders; 1989. p. 189-94.
21. Chung E M, Hague J P, Evans D H, Revealing the mechanisms underlying embolic stroke using computational modelling, Phys Med Biol. 2007 Dec. 7; 52(23): 7153-66. Epub 2007 Nov. 19.
22. Pyung et al., Successful percutaneous endovascular retrieval of a coil in the left ventricle which migrated during embolisation for pulmonary arteriovenous malformation. International Journal of Cardiology 163 (2013) e33-e35

The invention claimed is:

1. An embolization device loading system, the loading system comprising:
   (a) a bristle device, the bristle device comprising:
      (i) a stem, the stem comprising a proximal segment and a distal segment, the proximal segment comprising a first plurality of bristles extending outwardly from the stem of the proximal segment, and the distal segment comprising a second plurality of bristles extending outwardly from the stem of the distal segment, wherein the second plurality of bristles are longitudinally spaced from the first plurality of bristles; and
      (ii) a flow restrictor comprising a membrane, the flow restrictor extending outwardly from the stem, wherein the flow restrictor is coupled to the stem at a position located longitudinally within one of the first plurality of bristles and the second plurality of bristles such that there are bristles of the one of the first plurality of bristles and the second plurality of bristles both immediately distal and proximal to the flow restrictor;
   (b) a loading tube; and
   (c) a loading wire for loading the bristle device into the loading tube.

2. The embolization device loading system of claim 1, wherein the flow restrictor has a contracted configuration and an expanded configuration.

3. The embolization device loading system of claim 1, wherein the flow restrictor is located longitudinally within the first plurality of bristles of the proximal segment of the stem.

4. The embolization device loading system of claim 1, wherein the flow restrictor is located longitudinally within the second plurality of bristles of the distal segment of the stem.

5. The embolization device loading system of claim 1, wherein the flow restrictor membrane comprises a flexible material.

6. The embolization device loading system of claim 1, wherein the flow restrictor membrane comprises a polymeric material.

7. The embolization device loading system of claim 6, wherein the flow restrictor membrane comprises an elastomeric material.

8. The embolization device loading system of claim 1, wherein the flow restrictor membrane comprises a film.

9. The embolization device loading system of claim 1, wherein the flow restrictor membrane is impermeable.

10. The embolization device loading system of claim 1, wherein the flow restrictor membrane has a disk shape.

11. The embolization device loading system of claim 1, wherein the flow restrictor membrane has a conical shape in the expanded configuration.

12. The embolization device loading system of claim 1, wherein the first plurality of bristles extend circumferentially from the proximal segment of the stem and the second plurality of bristles extend circumferentially from the distal segment of the stem.

13. The embolization device loading system of claim 1, wherein the first plurality of bristles have a collapsed configuration in which each of the bristles of the first plurality of bristles point proximally, and the second plurality of bristles have a collapsed configuration in which each of the bristles of the second plurality of bristles point distally.

14. The embolization device loading system of claim 1, wherein the first plurality of bristles have an expanded configuration in which the bristles extend generally radially outwardly from the proximal segment of the stem, and the second plurality of bristles have an expanded configuration in which the bristles extend generally radially outwardly from the distal segment of the stem.

15. The embolization device loading system of claim 1, wherein the first plurality of bristles have an expanded configuration wherein the bristles extend partially in a first longitudinal direction and the second plurality of bristles have an expanded configuration wherein the bristles extend partially in a second longitudinal direction which is opposite to the first longitudinal direction.

16. The embolization device loading system of claim 1, wherein the first and second plurality of bristles comprise flexible bristles.

17. The embolization device loading system of claim 1, wherein the stem further comprises a connector coupling the proximal segment of the stem to the distal segment of the stem.

18. The embolization device loading system of claim 17, wherein the connector is flexible.

19. The embolization device loading system of claim 17 wherein the connector is a tube coupled to a distal end of the proximal segment such that the distal end of the proximal segment is positioned within the tube and a proximal end of the distal segment such that the proximal end of the distal segment is positioned within the tube.

20. The embolization device loading system of claim 17, wherein the connector is extendable.

21. The embolization device loading system of claim 1, wherein a spacing between the first plurality of bristles and the second plurality of bristles defines a gap distance and wherein a spacing between each of the longitudinally adjacent bristles within the first and second plurality of bristles is less than the gap distance.

22. The embolisation device loading system of claim 1, wherein the bristle device is configured to cause denudation to an endothelium of a lumen wall.

23. The embolisation device loading system of claim 1, wherein the membrane comprises an expanded diameter, which is smaller than an expanded diameter of the one or more the first plurality of bristles and the second plurality of bristles.

* * * * *